(12) United States Patent
Ching et al.

(10) Patent No.: US 9,624,531 B2
(45) Date of Patent: Apr. 18, 2017

(54) CASSETTE FOR SAMPLE PREPARATION

(71) Applicant: LUMINEX CORPORATION, Austin, TX (US)

(72) Inventors: Jesus Ching, San Jose, CA (US); David Hsiang Hu, Palo Alto, CA (US); Steve Jia Chang Yu, San Jose, CA (US); Phillip You Fai Lee, San Francisco, CA (US)

(73) Assignee: LUMINEX CORPORATION, Austin, TX (US)

( * ) Notice: Subject to any disclaimer, the term of this patent is extended or adjusted under 35 U.S.C. 154(b) by 111 days.

(21) Appl. No.: 14/666,573

(22) Filed: Mar. 24, 2015

(65) Prior Publication Data

US 2015/0191776 A1 Jul. 9, 2015

Related U.S. Application Data

(60) Continuation of application No. 13/910,953, filed on Jun. 5, 2013, now Pat. No. 9,017,617, which is a
(Continued)

(51) Int. Cl.
*B01J 19/08* (2006.01)
*C12Q 1/68* (2006.01)
(Continued)

(52) U.S. Cl.
CPC ........ *C12Q 1/6806* (2013.01); *B01F 11/0071* (2013.01); *B01F 15/0203* (2013.01);
(Continued)

(58) Field of Classification Search
CPC .......... B01F 2015/0221; B01F 15/0203; B01F 11/0071; B01F 15/0237; B01L 2300/0867; B01L 2400/0644; B01L 2200/16; B01L 2300/0672; B01L 7/00; B01L 2300/042; B01L 2400/0622; B01L 2200/026; B01L 2400/0478; B01L 2200/10; B01L 2400/0481; B01L 3/502; C12Q 1/6806; G01N 1/38; Y10T 436/25375;
(Continued)

(56) References Cited

U.S. PATENT DOCUMENTS 2,940,448 A 6/1960 Furlong .................. 600/579
3,607,094 A 9/1971 Beer ....................... 422/63
(Continued)

FOREIGN PATENT DOCUMENTS

CA 2626808 4/2007
DE 10319045 12/2004
(Continued)

OTHER PUBLICATIONS

Extended Search Report and Opinion, issued in European Application No. 06817150.3, dated May 28, 2014.
(Continued)

*Primary Examiner* — Dennis M White
(74) *Attorney, Agent, or Firm* — Parker Highlander PLLC

(57) ABSTRACT

Apparatuses for preparing a sample are disclosed herein. The apparatuses include a chamber, a first valve at least partially disposed in the first chamber, a second valve at least partially disposed in the first chamber, and a pump comprising an actuator and nozzle.

15 Claims, 40 Drawing Sheets

Related U.S. Application Data division of application No. 13/357,947, filed on Jan. 25, 2012, now Pat. No. 8,476,078, which is a continuation of application No. 12/789,831, filed on May 28, 2010, now Pat. No. 8,124,024, which is a continuation of application No. 11/582,651, filed on Oct. 17, 2006, now Pat. No. 7,727,473.

(60) Provisional application No. 60/753,622, filed on Dec. 22, 2005, provisional application No. 60/753,618, filed on Dec. 22, 2005, provisional application No. 60/728,569, filed on Oct. 19, 2005.

(51) Int. Cl.
  *B01F 11/00* (2006.01)
  *B01F 15/02* (2006.01)
  *B01L 3/00* (2006.01)
  *G01N 1/38* (2006.01)
  *B01L 7/00* (2006.01)

(52) U.S. Cl.
  CPC .......... *B01F 15/0237* (2013.01); *B01L 3/502* (2013.01); *G01N 1/38* (2013.01); *B01F 2015/0221* (2013.01); *B01L 7/00* (2013.01); *B01L 2200/026* (2013.01); *B01L 2200/0647* (2013.01); *B01L 2200/10* (2013.01); *B01L 2200/16* (2013.01); *B01L 2300/042* (2013.01); *B01L 2300/0672* (2013.01); *B01L 2300/0867* (2013.01); *B01L 2400/0478* (2013.01); *B01L 2400/0481* (2013.01); *B01L 2400/0622* (2013.01); *B01L 2400/0644* (2013.01); *B01L 2400/0683* (2013.01); *Y10T 137/0402* (2015.04); *Y10T 137/0407* (2015.04); *Y10T 137/0413* (2015.04); *Y10T 137/0419* (2015.04); *Y10T 137/0424* (2015.04); *Y10T 436/10* (2015.01); *Y10T 436/11* (2015.01); *Y10T 436/115831* (2015.01); *Y10T 436/118339* (2015.01); *Y10T 436/25* (2015.01); *Y10T 436/255* (2015.01); *Y10T 436/2575* (2015.01); *Y10T 436/25375* (2015.01)

(58) Field of Classification Search
  CPC .......... Y10T 436/255; Y10T 137/0419; Y10T 137/0407; Y10T 137/0402; Y10T 137/0424; Y10T 137/0413; Y10T 436/11; Y10T 436/10; Y10T 436/2575; Y10T 436/118339; Y10T 436/25; Y10T 436/115
  See application file for complete search history.

(56) References Cited

U.S. PATENT DOCUMENTS

| | | | |
|---|---|---|---|
| 3,802,782 A | 4/1974 | Natelson | 356/409 |
| 4,004,150 A | 1/1977 | Natelson | 250/328 |
| 4,201,578 A | 5/1980 | Abbott | 430/222 |
| 4,439,039 A | 3/1984 | Suovaniemi | 356/416 |
| 4,448,534 A | 5/1984 | Wertz et al. | 356/435 |
| 4,495,149 A | 1/1985 | Iwata et al. | 422/65 |
| 4,626,684 A | 12/1986 | Landa | 250/328 |
| 4,762,420 A | 8/1988 | Bowley | 356/436 |
| 5,035,505 A | 7/1991 | Tsukada et al. | 356/319 |
| 5,073,029 A | 12/1991 | Eberly et al. | 356/432 |
| 5,139,745 A | 8/1992 | Barr et al. | 422/82.05 |
| 5,188,455 A | 2/1993 | Hammerstedt | 366/177.1 |
| 5,229,297 A | 7/1993 | Schnipelsky et al. | 436/94 |
| 5,234,665 A | 8/1993 | Ohta et al. | 422/73 |
| 5,242,660 A | 9/1993 | Hsei | 422/548 |
| 5,242,837 A | 9/1993 | Slovacek et al. | 436/536 |
| 5,283,624 A | 2/1994 | Tsukada et al. | 356/319 |
| 5,290,513 A | 3/1994 | Berthold et al. | 422/52 |
| 5,307,144 A | 4/1994 | Hiroshi et al. | 356/244 |
| 5,333,675 A | 8/1994 | Mullis et al. | 165/268 |
| 5,348,853 A | 9/1994 | Wang et al. | 435/6.12 |
| 5,389,524 A | 2/1995 | Larsen et al. | 435/29 |
| 5,397,709 A | 3/1995 | Berndt | 436/34 |
| 5,411,876 A | 5/1995 | Bloch et al. | 435/91.2 |
| 5,415,839 A | 5/1995 | Zaun et al. | 422/64 |
| 5,436,718 A | 7/1995 | Fernandes et al. | 356/73 |
| 5,475,610 A | 12/1995 | Atwood et al. | 700/269 |
| 5,494,646 A | 2/1996 | Seymour | 422/401 |
| 5,500,188 A | 3/1996 | Hafeman et al. | 204/403.01 |
| 5,508,197 A | 4/1996 | Hansen et al. | 435/285.1 |
| 5,511,558 A | 4/1996 | Shepard et al. | 600/573 |
| 5,525,300 A | 6/1996 | Danssaert et al. | 422/552 |
| 5,525,466 A | 6/1996 | Slovacek et al. | 435/6.11 |
| 5,538,849 A | 7/1996 | Uematsu et al. | 435/6.19 |
| 5,541,072 A | 7/1996 | Wang et al. | 435/7.21 |
| 5,576,197 A | 11/1996 | Arnold | 435/91.2 |
| 5,578,818 A | 11/1996 | Kain et al. | 250/234 |
| 5,580,523 A | 12/1996 | Bard | 422/50 |
| 5,585,242 A | 12/1996 | Bouma et al. | 435/6.12 |
| 5,589,136 A | 12/1996 | Northrup et al. | 422/129 |
| 5,616,301 A | 4/1997 | Moser et al. | 422/64 |
| 5,627,041 A | 5/1997 | Shartle | 435/7.24 |
| 5,639,423 A | 6/1997 | Northrup et al. | 422/50 |
| 5,645,801 A | 7/1997 | Bouma et al. | 422/68.1 |
| 5,656,493 A | 8/1997 | Mullis et al. | 435/286.1 |
| 5,657,118 A | 8/1997 | Lee | 356/246 |
| 5,661,301 A | 8/1997 | Weiss | 850/26 |
| 5,665,975 A | 9/1997 | Kedar | 250/573 |
| 5,674,743 A | 10/1997 | Ulmer | 435/287.2 |
| 5,686,300 A | 11/1997 | Berndt | 435/287.5 |
| 5,705,628 A | 1/1998 | Hawkins | 536/25.4 |
| 5,738,825 A | 4/1998 | Rudigier et al. | 422/82.11 |
| 5,746,978 A | 5/1998 | Bienhaus et al. | 422/68.1 |
| 5,759,784 A | 6/1998 | Asp et al. | 435/6.12 |
| 5,811,312 A | 9/1998 | Hasegawa et al. | 436/527 |
| 5,825,478 A | 10/1998 | Wilcox et al. | 356/73 |
| 5,827,480 A | 10/1998 | Haff et al. | 422/68.1 |
| 5,837,144 A | 11/1998 | Bienhaus et al. | 210/695 |
| 5,861,124 A | 1/1999 | Hosoi et al. | 422/82.08 |
| 5,863,801 A | 1/1999 | Southgate et al. | 436/63 |
| 5,882,903 A | 3/1999 | Andrevski et al. | 435/91.2 |
| 5,897,783 A | 4/1999 | Howe et al. | 210/695 |
| 5,904,899 A | 5/1999 | Hayashi | 422/65 |
| 5,935,522 A | 8/1999 | Swerdlow et al. | 422/70 |
| 5,989,499 A | 11/1999 | Catanzariti et al. | 422/63 |
| 6,004,512 A | 12/1999 | Titcomb et al. | 422/63 |
| 6,015,674 A | 1/2000 | Woudenber et al. | 435/6.12 |
| 6,027,945 A | 2/2000 | Smith et al. | 436/526 |
| 6,043,506 A | 3/2000 | Heffelfinger et al. | 250/584 |
| 6,050,719 A | 4/2000 | Winkler et al. | 366/144 |
| 6,057,163 A | 5/2000 | McMillian | 436/172 |
| 6,061,128 A | 5/2000 | Zweig et al. | 356/243.4 |
| 6,071,748 A | 6/2000 | Modlin et al. | 436/174 |
| 6,096,272 A | 8/2000 | Clark et al. | 422/64 |
| 6,211,989 B1 | 4/2001 | Wulf et al. | 359/210.1 |
| 6,222,619 B1 | 4/2001 | Herron et al. | 356/39 |
| 6,228,634 B1 | 5/2001 | Blumenfeld et al. | 435/286.1 |
| 6,232,608 B1 | 5/2001 | Giebeler et al. | 250/458.1 |
| 6,281,008 B1 | 8/2001 | Komai et al. | 435/306.1 |
| 6,296,810 B1 | 10/2001 | Ulmer | 422/82.07 |
| 6,297,018 B1 | 10/2001 | French et al. | 435/5 |
| 6,353,475 B1 | 3/2002 | Jensen et al. | 356/244 |
| 6,358,387 B1 | 3/2002 | Kopf-Sill et al. | 204/603 |
| 6,369,893 B1 | 4/2002 | Christel et al. | 356/417 |
| 6,429,007 B1 | 8/2002 | Kluttz et al. | 435/286.5 |
| 6,431,476 B1 | 8/2002 | Taylor et al. | 241/1 |
| 6,440,725 B1 | 8/2002 | Pourahmadi et al. | 435/288.5 |
| 6,451,258 B1 | 9/2002 | Malmqvist | 422/417 |
| 6,468,810 B1 | 10/2002 | Korpela | 436/526 |
| 6,492,162 B1 | 12/2002 | Sakurai et al. | 435/285.1 |
| 6,517,778 B1 | 2/2003 | Kumar et al. | 422/82.05 |
| 6,520,197 B2 | 2/2003 | Deshmukh et al. | 137/3 |
| 6,545,758 B1 | 4/2003 | Sandstrom | 356/317 |
| 6,565,815 B1 | 5/2003 | Chang et al. | 422/198 |
| 6,569,631 B1 | 5/2003 | Pantoliano et al. | 506/9 |
| 6,576,459 B2 | 6/2003 | Miles et al. | 435/286.5 |
| 6,597,450 B1 | 7/2003 | Andrews et al. | 356/317 |

(56) References Cited

U.S. PATENT DOCUMENTS

| | | | |
|---|---|---|---|
| 6,645,758 B1 | 11/2003 | Schnipelsky et al. | 435/287.2 |
| 6,657,169 B2 | 12/2003 | Brown | 219/476 |
| 6,672,458 B2 | 1/2004 | Hansen et al. | 209/224 |
| 6,699,713 B2 | 3/2004 | Benett et al. | 435/287.2 |
| 6,730,501 B2 | 5/2004 | Eyre et al. | 435/91.2 |
| 6,730,883 B2 | 5/2004 | Brown et al. | 219/428 |
| 6,739,531 B2 | 5/2004 | Taylor | 241/1 |
| 6,764,859 B1 | 7/2004 | Kreuwel et al. | 436/178 |
| 6,783,934 B1 | 8/2004 | McMillan et al. | 435/6.11 |
| 6,787,338 B2 | 9/2004 | Wittwer et al. | 435/91.2 |
| 6,814,934 B1 | 11/2004 | Higuchi | 422/82.08 |
| 6,818,185 B1 | 11/2004 | Petersen et al. | 422/547 |
| 6,838,680 B2 | 1/2005 | Maher et al. | 250/458.1 |
| 6,852,284 B1 | 2/2005 | Holl et al. | 422/68.1 |
| 6,875,602 B2 | 4/2005 | Gutierrez | 435/286.2 |
| 6,890,742 B2 | 5/2005 | Ammann et al. | 435/91.2 |
| 6,893,879 B2 | 5/2005 | Petersen et al. | 436/178 |
| 6,908,759 B2 | 6/2005 | Jang | 435/285.1 |
| 6,927,852 B2 | 8/2005 | Reel | 356/317 |
| 6,955,589 B2 | 10/2005 | Kordonski et al. | 451/60 |
| 6,982,431 B2 | 1/2006 | Modlin et al. | 250/573 |
| 6,986,848 B2 | 1/2006 | Ikeda et al. | 210/695 |
| 7,008,789 B2 | 3/2006 | Gambini et al. | 435/287.2 |
| 7,027,683 B2 | 4/2006 | O'Connor et al. | 385/19 |
| 7,078,224 B1 | 7/2006 | Bitner et al. | 435/270 |
| 7,108,472 B2 | 9/2006 | Norris et al. | 414/222.07 |
| 7,148,043 B2 | 12/2006 | Kordunsky et al. | 435/6.12 |
| 7,171,863 B2 | 2/2007 | Tamura et al. | 73/864.14 |
| 7,223,949 B2 | 5/2007 | Deka et al. | 219/548 |
| 7,236,237 B2 | 6/2007 | Schmilovitch et al. | 356/73 |
| 7,284,900 B2 | 10/2007 | Mayer | 366/197 |
| 7,294,466 B2 | 11/2007 | McMillan | 435/6.12 |
| 7,301,628 B2 | 11/2007 | Cunningham et al. | 356/326 |
| 7,329,488 B2 | 2/2008 | Roh et al. | 435/6.19 |
| 7,341,691 B2 | 3/2008 | Tamura et al. | 422/64 |
| 7,344,894 B2 | 3/2008 | Greenstein et al. | 436/518 |
| 7,358,078 B2 | 4/2008 | Chen et al. | 435/286.5 |
| 7,373,253 B2 | 5/2008 | Eyre | 702/19 |
| 7,387,891 B2 | 6/2008 | Boege et al. | 435/288.7 |
| 7,394,547 B2 | 7/2008 | Tan et al. | 356/480 |
| 7,423,750 B2 | 9/2008 | Hoshizaki et al. | 356/317 |
| 7,459,302 B2 | 12/2008 | Reid et al. | 435/286.1 |
| 7,498,164 B2 | 3/2009 | Oldham et al. | 435/288.7 |
| 7,507,575 B2 | 3/2009 | Bedingham et al. | 435/287.2 |
| 7,521,179 B2 | 4/2009 | Bachi | 435/6.11 |
| 7,584,019 B2 | 9/2009 | Feingold et al. | 700/245 |
| 7,585,663 B2 | 9/2009 | Shigeura et al. | 435/287.2 |
| 7,682,565 B2 | 3/2010 | Linton et al. | 422/68.1 |
| 7,699,979 B2 | 4/2010 | Li et al. | 210/138 |
| 7,718,072 B2 | 5/2010 | Safar et al. | 210/695 |
| 7,718,421 B2 | 5/2010 | Chen et al. | 435/288.5 |
| 7,727,473 B2 | 6/2010 | Ching et al. | 422/68.1 |
| 7,754,148 B2 | 7/2010 | Yu et al. | 422/65 |
| 7,910,062 B2 | 3/2011 | Yu et al. | 472/65 |
| 8,029,746 B2 | 10/2011 | Yu et al. | 422/537 |
| 8,048,386 B2 | 11/2011 | Dority et al. | 422/500 |
| 8,124,024 B2 | 2/2012 | Ching et al. | 422/417 |
| 8,133,703 B2 | 3/2012 | Ching et al. | 435/91.2 |
| 8,168,443 B2 | 5/2012 | Yu et al. | 436/174 |
| 8,372,340 B2 | 2/2013 | Bird et al. | 422/63 |
| 8,476,078 B2 | 7/2013 | Ching et al. | 436/174 |
| 8,900,877 B2 | 12/2014 | Yu et al. | 436/174 |
| 9,017,617 B2 | 4/2015 | Ching et al. | 422/186.1 |
| 2001/0036472 A1 | 11/2001 | Anderson et al. | 436/180 |
| 2003/0016352 A1 | 1/2003 | Goldman et al. | 356/317 |
| 2003/0073110 A1 | 4/2003 | Aritomi et al. | 435/6.12 |
| 2003/0129739 A1 | 7/2003 | Jones | 435/287.2 |
| 2003/0170686 A1 | 9/2003 | Hoet et al. | 435/6.12 |
| 2003/0203491 A1 | 10/2003 | Andrevski et al. | 436/46 |
| 2003/0224436 A1 | 12/2003 | Nelson et al. | 435/6.12 |
| 2004/0126783 A1 | 7/2004 | Bortolin et al. | 435/6.12 |
| 2004/0161788 A1 | 8/2004 | Chen et al. | 435/6.11 |
| 2004/0200909 A1 | 10/2004 | McMillan et al. | 241/1 |
| 2004/0209266 A1 | 10/2004 | Squirrell | 435/6.11 |
| 2004/0222395 A1 | 11/2004 | Yee | 251/65 |
| 2004/0259237 A1 | 12/2004 | Kellogg et al. | 435/287.1 |
| 2005/0194316 A1 | 9/2005 | Pourahmadi et al. | 210/638 |
| 2005/0244837 A1 | 11/2005 | McMillan et al. | 435/6.12 |
| 2006/0011539 A1 | 1/2006 | Lee et al. | 210/613 |
| 2006/0013725 A1 | 1/2006 | Larsen | 422/400 |
| 2006/0019379 A1 | 1/2006 | Taylor et al. | 435/306.1 |
| 2006/0030038 A1 | 2/2006 | Taylor et al. | 435/306.1 |
| 2006/0094108 A1 | 5/2006 | Yoder et al. | 210/638 |
| 2006/0165558 A1 | 7/2006 | Witty et al. | 422/400 |
| 2006/0194264 A1 | 8/2006 | Sheppard et al. | 435/7.9 |
| 2006/0205085 A1 | 9/2006 | Handique et al. | 436/177 |
| 2006/0222569 A1 | 10/2006 | Barten et al. | 422/400 |
| 2006/0246490 A1 | 11/2006 | Anderson et al. | 435/6.11 |
| 2006/0257991 A1 | 11/2006 | McDevitt et al. | 435/287.2 |
| 2006/0269922 A1 | 11/2006 | Sagner et al. | 435/6.18 |
| 2006/0276972 A1 | 12/2006 | Light et al. | 702/19 |
| 2006/0292032 A1 | 12/2006 | Hataoka et al. | 422/552 |
| 2007/0036026 A1 | 2/2007 | Laibinis et al. | 366/273 |
| 2007/0054293 A1 | 3/2007 | Liu et al. | 435/287.2 |
| 2007/0054349 A1 | 3/2007 | Hickey | 435/32 |
| 2007/0077646 A1 | 4/2007 | Okamoto | 435/288.4 |
| 2007/0087431 A1 | 4/2007 | Ching et al. | 435/287.2 |
| 2007/0099289 A1 | 5/2007 | Irimia et al. | 435/287.2 |
| 2007/0125942 A1 | 6/2007 | Kido | 250/284 |
| 2007/0212698 A1 | 9/2007 | Bendele et al. | 435/6.16 |
| 2007/0248958 A1 | 10/2007 | Jovanovich et al. | 435/6.19 |
| 2007/0281288 A1 | 12/2007 | Belkin et al. | 435/4 |
| 2007/0292858 A1 | 12/2007 | Chen et al. | 435/6.18 |
| 2008/0003649 A1 | 1/2008 | Maltezos et al. | 435/91.2 |
| 2008/0050781 A1 | 2/2008 | Oldham et al. | 435/91.2 |
| 2008/0153096 A1 | 6/2008 | Witty et al. | 435/6.12 |
| 2008/0159915 A1 | 7/2008 | Yu et al. | 422/68.1 |
| 2008/0262213 A1 | 10/2008 | Wu et al. | 536/25.4 |
| 2008/0280285 A1 | 11/2008 | Chen et al. | 435/5 |
| 2008/0316482 A1 | 12/2008 | Hoshizaki et al. | 356/317 |
| 2009/0023201 A1 | 1/2009 | Hongo et al. | 435/287.2 |
| 2009/0030038 A1 | 1/2009 | Chu et al. | 514/312 |
| 2009/0130766 A1 | 5/2009 | Weekamp | 436/63 |
| 2009/0142745 A1 | 6/2009 | Breidenthal et al. | 435/3 |
| 2009/0155838 A1 | 6/2009 | Hale | 435/29 |
| 2009/0186344 A1 | 7/2009 | Farinas | 435/6.11 |
| 2009/0186357 A1 | 7/2009 | Mauk et al. | 435/6.15 |
| 2009/0215124 A1 | 8/2009 | Cao et al. | 435/91.2 |
| 2009/0269841 A1 | 10/2009 | Wojciechowski et al. | 435/325 |
| 2009/0291507 A1 | 11/2009 | Clemmens et al. | 436/501 |
| 2010/0112567 A1 | 5/2010 | Adolfsen et al. | 435/6.16 |
| 2010/0239471 A1 | 9/2010 | Ching et al. | 422/186.01 |
| 2010/0262303 A1 | 10/2010 | Yu et al. | 700/282 |
| 2010/0303687 A1 | 12/2010 | Blaga et al. | 422/504 |
| 2011/0008907 A1 | 1/2011 | Patno et al. | 436/174 |
| 2011/0158849 A1 | 6/2011 | Yu et al. | 422/63 |
| 2011/0236960 A1 | 9/2011 | Bird et al. | 435/283.1 |
| 2012/0003631 A1 | 1/2012 | Yu et al. | 435/6.1 |
| 2012/0122232 A1 | 5/2012 | Ching et al. | 436/180 |
| 2012/0288897 A1 | 11/2012 | Ching et al. | 435/91.2 |
| 2013/0115712 A1 | 5/2013 | Yu et al. | 436/174 |
| 2013/0266948 A1 | 10/2013 | Bird et al. | 435/6.12 |
| 2013/0337555 A1 | 12/2013 | Ching et al. | 435/309.1 |
| 2015/0050726 A1 | 2/2015 | Yu et al. | 435/309.1 |

FOREIGN PATENT DOCUMENTS

| | | |
|---|---|---|
| JP | 11-271227 | 5/1999 |
| JP | 2001-108684 | 4/2001 |
| JP | 2009-512447 | 3/2009 |
| JP | 2010-505108 | 2/2010 |
| WO | WO 01/13096 | 2/2001 |
| WO | WO 2004/005553 | 1/2004 |
| WO | WO 2004/080597 | 9/2004 |
| WO | WO 2006/071770 | 7/2006 |
| WO | WO 2008/037995 | 4/2008 |
| WO | WO 2009/105711 | 8/2009 |
| WO | WO 2010/132834 | 11/2010 |

OTHER PUBLICATIONS

Extended Search Report and Opinion, issued in European Application No. 11747970.9, dated May 28, 2014.

(56) References Cited

OTHER PUBLICATIONS

Extended Search Report and Opinion, issued in European Application No. 12779471.7, dated May 28, 2014.
International Search Report and Written Opinion issued in PCT Application No. PCT/US2006/40835, mailed Dec. 4, 2007.
International Search Report and Written Opinion issued in PCT Application No. PCT/US2011/25871, mailed May 5, 2011.
International Search Report and Written Opinion issued in PCT Application No. PCT/US2012/036491, mailed Oct. 5, 2012.
Office Action, issued in Australian Application No. 2006304623, dated Apr. 21, 2011.
Office Action, issued in Australian Application No. 2006304623, dated Sep. 9, 2013.
Office Action, issued in Canadian Application No. 2,626,808, dated Apr. 12, 2013.
Office Action, issued in Canadian Application No. 2,626,808, dated Jan. 10, 2014.
Office Action, issued in Canadian Application No. 2,626,808, dated Sep. 11, 2014.
Office Action, issued in Chinese Application No. 200680043554.3, dated Mar. 30, 2011 (English Translation).
Office Action, issued in Chinese Application No. 201310061818.X, dated Jun. 16, 2014 (English Translation).
Office Action issued in Japanese Patent Application No. 2008-536791, mailed Oct. 3, 2011.
Office Action, issued in Japanese Application No. 2008-536791, dated Jul. 17, 2012 (English Translation).
Office Action, issued in Korean Application No. 10-2008-7011947, dated May 22, 2013 (English Translation).
Office Action, issued in Korean Application No. 10-2013-7019433, dated Oct. 21, 2013 (English Translation).
Office Action, issued in Mexican Application No. MX/a/2008/005115, dated Sep. 7, 2010 (English Translation).
Office Action, issued in U.S. Appl. No. 12/789,831, dated Nov. 23, 2010.
Office Action, issued in U.S. Appl. No. 12/789,831, dated May 27, 2011.
Office Action, issued in U.S. Appl. No. 13/357,947, dated Oct. 5, 2012.
Office Action, issued in U.S. Appl. No. 13/910,953, dated Dec. 5, 2013.
Office Action, issued in U.S. Appl. No. 13/910,953, dated Mar. 28, 2014.
Office Action, issued in U.S. Appl. No. 12/005,860, dated Nov. 3, 2009.
Office Action, issued in U.S. Appl. No. 12/821,446, dated Sep. 1, 2010.
Office Action, issued in U.S. Appl. No. 13/459,469, dated May 15, 2013.
Office Action, issued in U.S. Appl. No. 13/459,469, dated Oct. 25, 2013.
Office Action, issued in U.S. Appl. No. 13/459,469, dated Mar. 28, 2014.
Office Action, issued in Australian Application No. 2011220873, dated Aug. 12, 2013.
Office Action, issued in Chinese Application No. 201180018623.6, dated Dec. 26, 2013.
Office Action, issued in Chinese Application No. 201180018623.6, dated Jul. 15, 2014.
Office Action, issued in Chinese Application No. 201180018623.6, dated Oct. 30, 2014.
Office Action, issued in Japanese Application No. 2012-555102, dated Feb. 24, 2015.
Office Action, issued in U.S. Appl. No. 13/759,557, dated May 29, 2014.
Office Action, issued in U.S. Appl. No. 13/759,557, dated Sep. 3, 2014.
Office Action, issued in U.S. Appl. No. 13/464,240, dated Nov. 20, 2014.
Office Action, issued in Canadian Application No. 2,796,586, dated Mar. 31, 2015.
Office Action, issued in Australian Application No. 2014201790, dated Apr. 23, 2015.
Office Action, issued in European Application No. 12 779 471.7, dated Apr. 9, 2015.
Pilosof and Nieman, "Microporous membrance flow cell with nonimmobilized enzyme for chemiluminescent determination of glucose," *Anal. Chem.*, 54:1698-1701, 1982.

CASSETTE FOR SAMPLE PREPARATION

CROSS-REFERENCE TO RELATED APPLICATIONS

This application is a continuation of U.S. application Ser. No. 13/910,953, filed Jun. 5, 2013, entitled "CASSETTE FOR SAMPLE PREPARATION," which is a divisional of U.S. application Ser. No. 13/357,947, now U.S. Pat. No. 8,476,078, filed Jan. 25, 2012, entitled "CASSETTE FOR SAMPLE PREPARATION," which is a continuation of U.S. application Ser. No. 12/789,831, now U.S. Pat. No. 8,124,024, filed May 28, 2010, entitled "CASSETTE FOR SAMPLE PREPARATION," which is a continuation of U.S. application Ser. No. 11/582,651, now U.S. Pat. No. 7,727,473, filed Oct. 17, 2006, entitled "CASSETTE FOR SAMPLE PREPARATION," which claims the benefit of U.S. Provisional Application No. 60/728,569, filed Oct. 19, 2005, entitled "CASSETTE FOR SAMPLE PREPARATION," U.S. Provisional Application No. 60/753,622, filed Dec. 22, 2005, entitled "CASSETTE FOR SAMPLE PREPARATION," and U.S. Provisional Application No. 60/753,618, filed Dec. 22, 2005, entitled "CASSETTE FOR SAMPLE PREPARATION," each of which is hereby incorporated by reference.

BACKGROUND

1). Field of the Invention

The present invention relates to the field of biotechnology devices and, in particular, to devices and methods for preparing samples.

2). Discussion of Related Art

DNA can be used to develop new drugs or to link someone to a crime. However, before this can be done, the DNA must be isolated from a sample. These samples include, for example, blood, urine, human cells, hair, bacteria, yeast and tissue. Each of these samples include cells, which include nucleic acid. Nucleic acid is a nucleotide chain, which conveys genetic information. The most common forms of nucleic acid are DNA and RNA.

In order to isolate the nucleic acid from the samples, prior art devices use a tray having several exposed cavities. The sample is placed into one of the cavities and conventional processing steps are used to isolate the DNA from the sample.

This prior art system has several disadvantages, including contamination. Since the cavities are exposed, contaminants can easily affect the DNA. In addition, the prior art system requires the preparation of several samples at one time. It is difficult to prepare one or two samples at a time using the prior art devices.

SUMMARY

A cassette for preparing a sample is disclosed herein. The cassette includes at least one mixing chamber for receiving a sample of cells; a first holding chamber; an enzyme in the first holding chamber, the enzyme being transferable into the at least one mixing chamber to break the cells and release nucleic acid from the cells to create bulk material and the nucleic acid in the bulk material; a second holding chamber; magnetic particles in the second holding chamber, the magnetic particles being transferable to the at least one mixing chamber to bind with the nucleic acid; and at least one magnet, positionable to attract the magnetic particles together with the nucleic acid and at least partially separate the nucleic acid from the bulk material in the at least one mixing chamber.

The mixing chamber has a top surface, the top surface having an opening therein. A removable lid for accessing the opening of the mixing chamber is also provided. The enzyme may be proteinase K. First and second plungers in the first holding chamber and second holding chamber may also be provided, each plunger being movable to transfer the enzyme and magnetic particles, respectively, into the mixing chamber. A thin film that is breakable to transfer the enzyme and magnetic particles through respective ruptures in the thin film into the mixing chamber may also be provided. First and second plungers in the first holding chamber and second holding chamber, each plunger being movable to break the thin film and transfer the enzyme and magnetic particles, respectively, into the mixing chamber, may also be provided. A third holding chamber and a lysis solution in the third holding chamber may also be provided, the lysis solution being transferable into the mixing chamber to solubilize the bulk material. A fourth holding chamber and a binding solution in the fourth holding chamber may also be provided, the binding solution being transferable into the mixing chamber to bind the nucleic acid to the magnetic particles. A heating element for heating the mixing chamber may also be provided.

The cassette may also include a first separation piece having a surface; a first transfer piece having a surface with a cavity therein, the at least one magnet transferring the magnetic particles together with the nucleic acid into the cavity in the surface of the first transfer piece, the first transfer piece being movable relative to the first separation piece so that the magnetic particles together with the nucleic acid move out of the mixing chamber and past the surface of the first separation piece; and a first receiving chamber which receives the magnetic particles and nucleic acid after moving past the surface of the first separation piece. The cassette may further include a second separation piece having a surface; a second transfer piece having a surface with a cavity therein, the second transfer piece being movable relative to the second separation piece so that the magnetic particles together with the nucleic acid move out of the first receiving chamber and past the surface of the second separation piece; and a second receiving chamber which receives the magnetic particles and nucleic acid after moving past the surface of the second separation piece. The cassette may yet further include a third separation piece having a surface; a third transfer piece having a surface with a cavity therein, the third transfer piece being movable relative to the third separation piece so that the magnetic particles together with the nucleic acid move out of the second receiving chamber and past the surface of the third separation piece; and a third receiving chamber which receives the magnetic particles and nucleic acid after moving past the surface of the third separation piece.

The first receiving chamber may be a washing chamber, and the cassette may further include a washing solution in the washing chamber. The second receiving chamber may be a washing chamber, and the cassette may further include a washing solution in the washing chamber. The third receiving chamber may be an elution chamber, and the cassette may further include an elution buffer in the elution chamber for separating the magnetic particles and the nucleic acid.

A cassette for preparing a sample is disclosed herein. The cassette includes at least one mixing chamber for receiving a sample of cells, an enzyme being added in the mixing chamber to break the cells and release nucleic acid from the cells to create bulk material and nucleic acid in the bulk material, magnetic particles being added to the mixing chamber to bind with the nucleic acid; a first separation piece having a surface; a first transfer piece having a surface with a cavity therein; a magnet, positionable to attract the magnetic particles together with the nucleic acid and at least partially separate the nucleic acid from the bulk material in the at least one mixing chamber and to transfer the magnetic particles together with the nucleic acid into the cavity in the surface of the first transfer piece, the first transfer piece being movable relative to the first separation piece so that the magnetic particles together with the nucleic acid move out of the mixing chamber and past the surface of the first separation piece; and a first receiving chamber which receives the magnetic particles and nucleic acid after moving past the surface of the first separation piece.

The second piece may be rotatable relative to the first piece. The first receiving chamber may be a washing chamber, and the cassette may further include a washing solution in the washing chamber. The cassette may also include an elution chamber, and an elution buffer in the elution chamber for separating the magnetic particles and the nucleic acid. The cassette may also include a second separation piece having a surface, a second transfer piece having a surface with a cavity therein, the second transfer piece being movable relative to the second separation piece so that the magnetic particles together with the nucleic acid move out of the first receiving chamber and past the surface of the second separation piece, the elution chamber receiving the magnetic particles and nucleic acid after moving past the surface of the first separation piece. The second transfer piece may be moveable relative to the second separation piece so that the magnetic particles move out of the elution chamber, leaving the nucleic acid in the elution chamber.

The secondary chamber may be an elution chamber and the cassette may further include an elution buffer in the elution chamber for separating the magnetic particles and the nucleic acid. The cassette may also include a second separation piece having a surface, a second transfer piece having a surface with a cavity therein, the second transfer piece being movable relative to the second separation piece so that the magnetic particles together with the nucleic acid move out of the first receiving chamber and past the surface of the second separation piece, and a second receiving chamber which receives the magnetic particles and nucleic acid after moving past the surface of the second separation piece. The cassette may further include a third separation piece having a surface, a third transfer piece having a surface with a cavity therein, the third transfer piece being movable relative to the third separation piece so that the magnetic particles together with the nucleic acid move out of the second receiving chamber and past the surface of the third separation piece, and a third receiving chamber which receives the magnetic particles and nucleic acid after moving past the surface of the third separation piece. The second receiving chamber may be a washing chamber, and the cassette may further include a washing solution in the washing chamber. The third receiving chamber may be an elution chamber, and the cassette may further include an elution buffer in the elution chamber for separating the magnetic particles and the nucleic acid.

A cassette for preparing samples is disclosed herein. The cassette includes an enclosure, the enclosure comprising a mixing chamber, the mixing chamber including an opening for receiving a sample of cells having nucleic acid; a plurality of holding chambers having contents, the contents of one of the plurality of holding chambers comprising magnetic particles, and the contents of one of the plurality of holding chambers comprising a proteinase K solution; a plurality of plungers, each of the plurality of plungers corresponding to one of the plurality of holding chambers, for transferring the contents of the plurality of holding chambers into the mixing chamber, the proteinase K solution breaking up the cells to release the nucleic acid and the nucleic acid binding to the magnetic particles in the mixing chamber; a first valve, coupled to the mixing chamber, the first valve including a positionable magnet for attracting the magnetic particles; a washing chamber, coupled to the first valve; a second valve, coupled to the first washing chamber, the second valve including a positionable magnet for attracting the magnetic particles; and an elution chamber, coupled to the second valve, the elution chamber including an opening for removing the nucleic acid from the elution chamber.

One of the plurality of holding chambers may include a binding solution and one of the plurality of holding chambers may include a lysis solution, and wherein one of the plurality of plungers may transfer the binding solution into the mixing chamber and wherein one of the plurality of plungers may transfer the lysis solution into the mixing chamber.

A cassette for preparing a sample is disclosed herein. The cassette includes a reaction chamber for receiving a sample of cells; a first holding chamber; an enzyme in the first holding chamber, the enzyme being transferable into the reaction chamber to break the cells and release nucleic acid from the cells to create bulk material and the nucleic acid in the bulk material; a particle chamber; particles to bind with the nucleic acid in the particle chamber; a second holding chamber; an elution buffer in the second holding chamber to release the nucleic acid from the particles; and an elution chamber for receiving the elution buffer and the released nucleic acid, wherein the elution buffer is transferable from the holding chamber to the reaction chamber, through the particle chamber, and into the elution chamber.

The cassette may include a third holding chamber and a lysis solution in the third holding chamber, the lysis solution being transferable into the reaction chamber to solubilize the bulk material.

The cassette may include a fourth holding chamber and a binding solution in the fourth holding chamber, the binding solution being transferable into the reaction chamber to bind the nucleic acid to the particles.

The reaction chamber may be aligned with the particle chamber and the elution chamber may be alignable with the particle chamber.

The cassette may include a waste chamber for receiving the enzyme and bulk material.

The cassette may include a plunger to transfer the contents of the reaction chamber through the particle chamber and into the waste chamber.

The cassette may include a plunger to transfer the contents of the reaction chamber through the particle chamber and into the elution chamber.

The cassette may include a valve in each of the first and second holding chambers to transfer the contents of each of the first and second holding chambers into the reaction chamber.

The valve may include a plunger to transfer the contents from the valve into the reaction chamber.

Another cassette for preparing samples is also disclosed herein. The cassette includes an enclosure, the enclosure including a reaction chamber, the reaction chamber including an opening for receiving a sample of cells having nucleic acid; a plurality of holding chambers; an enzyme in one of the plurality of holding chambers; a lysis buffer in one of the plurality of holding chambers; a binding buffer in one of the plurality of holding chambers; an elution buffer in one of the plurality of holding chambers; a particle chamber; particles in the particle chamber, the particles to releasably bind with the nucleic acid; and an elution chamber to receive the released nucleic acid, the elution chamber including an opening for removing the nucleic acid from the enclosure.

The enclosure may include a waste chamber.

Each of the plurality of holding chambers may include a plunger for transferring contents of the plurality of holding chambers to the reaction chamber.

The cassette may include one or more washing buffers in one or more of the plurality of holding chambers.

The reaction chamber may be aligned with the particle chamber and wherein the elution chamber may be alignable with the particle chamber.

A further cassette for preparing a sample is also disclosed herein. The cassette includes a reaction chamber for receiving a sample of cells; a first holding chamber; an enzyme in the first holding chamber, the enzyme being transferable into the reaction chamber to break the cells and release nucleic acid from the cells to create bulk material and the nucleic acid in the bulk material; a particle chamber; particles to bind with the nucleic acid in the particle chamber; a second holding chamber; an elution buffer in the second holding chamber to release the nucleic acid from the particles; and an elution chamber for receiving the elution buffer and the released nucleic acid, wherein each of the holding chambers comprises an outer housing having a first chamber therein and at least one opening, the first chamber receiving a valve, the valve comprising: an inner housing having a second chamber therein and at least one opening, the inner housing rotatable relative to the outer housing/the at least one opening of the inner housing alignable with the at least one opening of the outer housing, the second chamber having contents; and a plunger in the second chamber to transfer the contents of the second chamber through the at least one opening of the inner housing and the at least one opening of the outer housing when the at least one opening of the inner housing and the at least one opening of the outer housing are aligned.

The cassette may include a third holding chamber and a lysis solution in the third holding chamber, the lysis solution being transferable into the reaction chamber to solubilize the bulk material.

The cassette may include a fourth holding chamber and a binding solution in the fourth holding chamber, the binding solution being transferable into the reaction chamber to bind the nucleic acid to the particles.

The cassette may include a waste chamber for receiving the enzyme and bulk material.

The cassette may include a plunger to transfer the contents of the reaction chamber through the particle chamber and into the waste chamber.

The cassette may include a plunger to transfer the contents of the reaction chamber through the particle chamber and into the elution chamber.

The reaction chamber may be aligned with the particle chamber and wherein the elution chamber may be alignable with the particle chamber.

BRIEF DESCRIPTION OF THE DRAWINGS

The invention is described by way of example with reference to the accompanying drawings, wherein.

DETAILED DESCRIPTION

Figure 1:
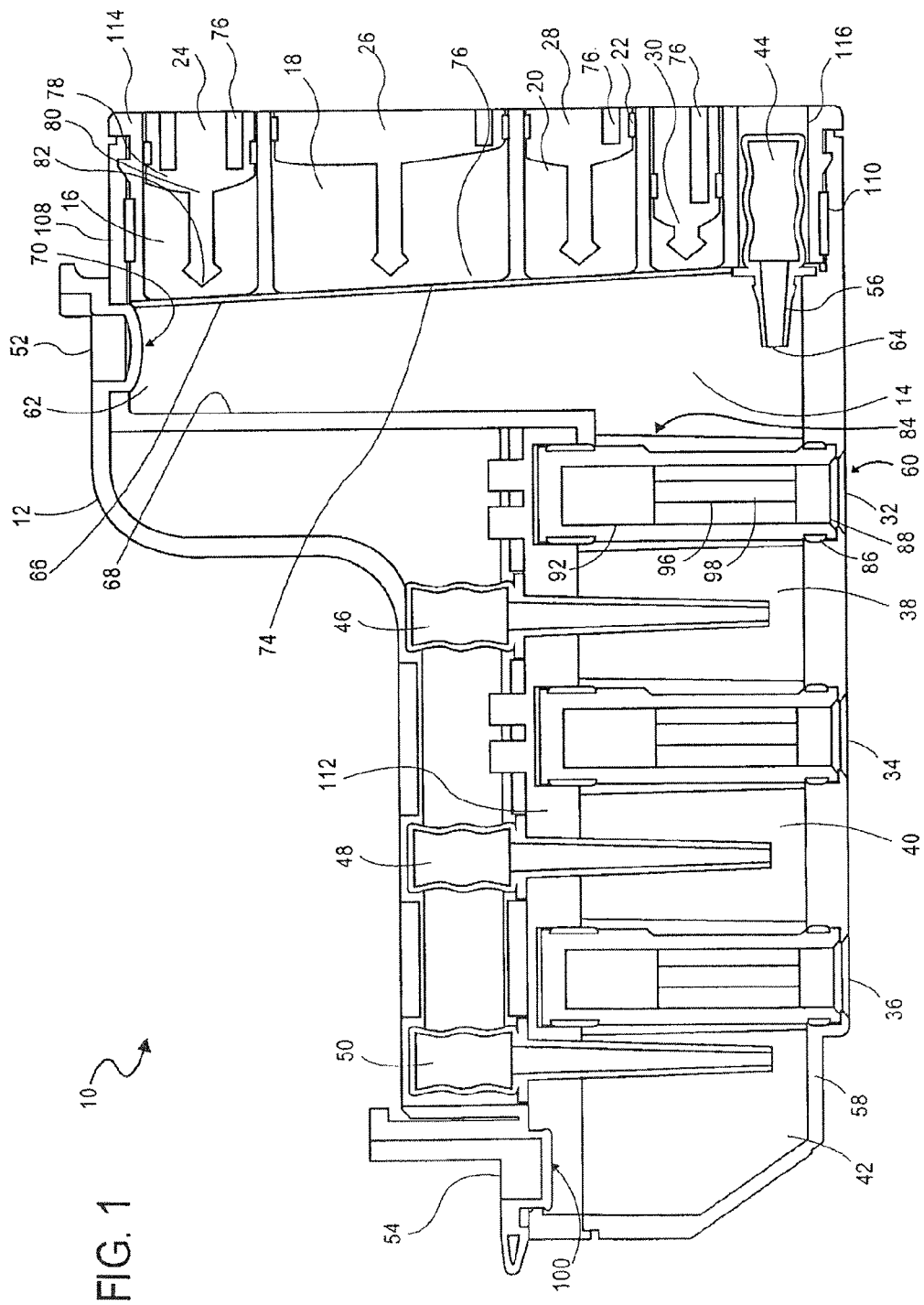
FIG. 1 is a cross-sectional side view of a cassette for preparing samples according to an embodiment of the invention.

FIG. 1 illustrates a cassette 10, which can be used to prepare cell samples. The cassette 10 includes a housing 12, a mixing chamber 14, first, second third and fourth holding chambers 16, 18,20 and 22, first, second, third and fourth plungers 24,26,28 and 30, first, second and third valves 32, 34 and 36, first and second washing chambers 38 and 40, an elution chamber 42, first, second, third and fourth pumps 44, 46, 48 and 50, first and second lids 52 and 54, first and second heating elements 56 and 58 and a magnet 60.

Each of the chambers 14, 16, 18, 20, 22, 38, 40 and 42, plungers 24, 26, 28 and 30, valves 32, 34 and 36, pumps 44, 46, 48 and 50, and heating elements 56 and 58 are enclosed within the housing. The lids 52 and 54 are movably attached to the housing 12. The magnet 60 is removably positionable in the first valve 32, second valve 34 and third valve 36.

The mixing chamber 14 has a top surface 62, a bottom surface 64 and opposing side surfaces 66, 68. The top surface 62 of the mixing chamber includes an opening 70 therein.

The first lid 52 is configured to provide access to the opening 70 in the top surface 62 of the mixing chamber. The first lid 52 and the opening 70 are coaxial. The first lid 52 is shown being movably attached to the housing 12, such that when the lid 52 is open or off, the opening 70 is accessible and if the lid 52 is closed or on, the opening 70 is not accessible.

A thin film 74 forms one wall of the mixing chamber 14. The thin film 74 is breakable, such that the mixing chamber 14 is accessible when the thin film 74 has been broken or ruptured.

The first holding chamber 16, second holding chamber 18, third holding chamber 20 and fourth holding chamber 22 are shown located next to the mixing chamber 14 and aligned vertically with one another. Each of the holding chambers 16, 18,20, 22 has an opening 76 next to the thin film 74 of the mixing chamber 14.

The cassette 10 further includes magnetic iron particles in the form of magnetic iron beads in the first holding chamber 16. The cassette 10 further includes a binding solution in the second holding chamber 18. The cassette 10 further includes a lysis solution in the third holding chamber 20. The cassette 10 further includes a proteinase K (PK) solution in the fourth holding chamber 22.

The first, second, third and fourth plungers 24, 26, 28 and 30 are located in the first, second, third and fourth holding chambers 16, 18, 20 and 22, respectively.

Each of the plungers 16, 18,20,22 includes a base 78, a shaft 80 and a piercing element 82. The shaft 80 extends from the base 78. The piercing element 82 is at the end of the shaft 80 opposing the base 78 and is pointed. The piercing element 82 is configured to break or rupture the thin film 74 of the mixing chamber 14.

The first pump 44 is a bellows pump having a pumping portion and a nozzle portion. The nozzle portion of the first pump 44 is located inside the mixing chamber 14. The pumping portion of the first pump 44 is located outside the mixing chamber, such that the pumping portion is actuatable.

A heating element 56 is provided at the bottom surface 64 of the mixing chamber 14 for heating the contents of the mixing chamber 14. The heating element 56 may be a variable heating element.

The opposing side surface 68 of the mixing chamber 14 also includes an opening 84. A first valve 32 is provided between the opening 84 in the side 68 of the mixing chamber 14 and the first washing chamber 38.

The first valve 32 has a first stationary piece 86 and a second moveable piece 88, the second piece 88 being moveable relative to the first piece 86. The first stationary piece 86 includes a first opening 90 and a second opening 92 and has a surface 94. The second piece 88 has an opening 94 therein for receiving the magnet 60. The second piece 88 has a surface 96 with a cavity 98 therein. The magnet 60 is shaped to correspond to the opening 94 in the second piece 88. The magnet 60 is moveable in the opening 94 of the second piece 88, and is removable from the second piece 88.

The cassette 10 includes a washing solution in the first washing chamber 38. The second pump 46 is also a bellows pump, and the nozzle portion of the second pump 46 is located in the first washing chamber 38.

The second valve 34 is provided between the first washing chamber 38 and the second washing chamber 40. The second valve 34 is structurally and functionally the same as the first valve 43, and also includes a first stationary piece 86 and a second moveable piece 88. The first stationary piece 86 includes a first opening 90 and a second opening 92 and has a surface 94. The second moveable piece 88 has a surface 96 with a cavity 98 therein.

The cassette 10 includes a washing solution in the second washing chamber 40. The third pump 48 is also a bellows pump, and the nozzle portion of the third pump 48 is located in the second washing chamber 40.

The third valve 36 is provided between the second washing chamber 40 and the elution chamber 42. The third valve 36 is structurally and functionally the same as the first valve 32 and the second valve 34, and also includes a first stationary piece 86 and a second moveable piece 88. The first stationary piece 86 includes a first opening 90 and a second opening 92 and has a surface 94. The second moveable piece 88 has a surface 96 with a cavity 98 therein.

The cassette 10 includes a washing solution in the elution chamber 42. The fourth pump 50 is also a bellows pump, and the nozzle portion of the fourth pump 50 is located in the elution chamber 42.

A heating element 58 is provided at the bottom surface of the elution chamber 42 for heating the contents of the elution chamber 42. The heating element 58 may be a variable heating element.

The elution chamber 42 includes an opening 100 at its top surface for accessing the contents of the elution chamber 42.

The second lid 54 is configured to provide access to the opening 100 in the top surface of the elution chamber 42. The second lid 54 is coaxial with the opening 100. The second lid 54 is shown being movably attached to the housing 12, such that when the lid 54 is open or off, the opening 100 is accessible and if the lid 54 is closed or on, the opening 100 is not accessible.

Figure 2:
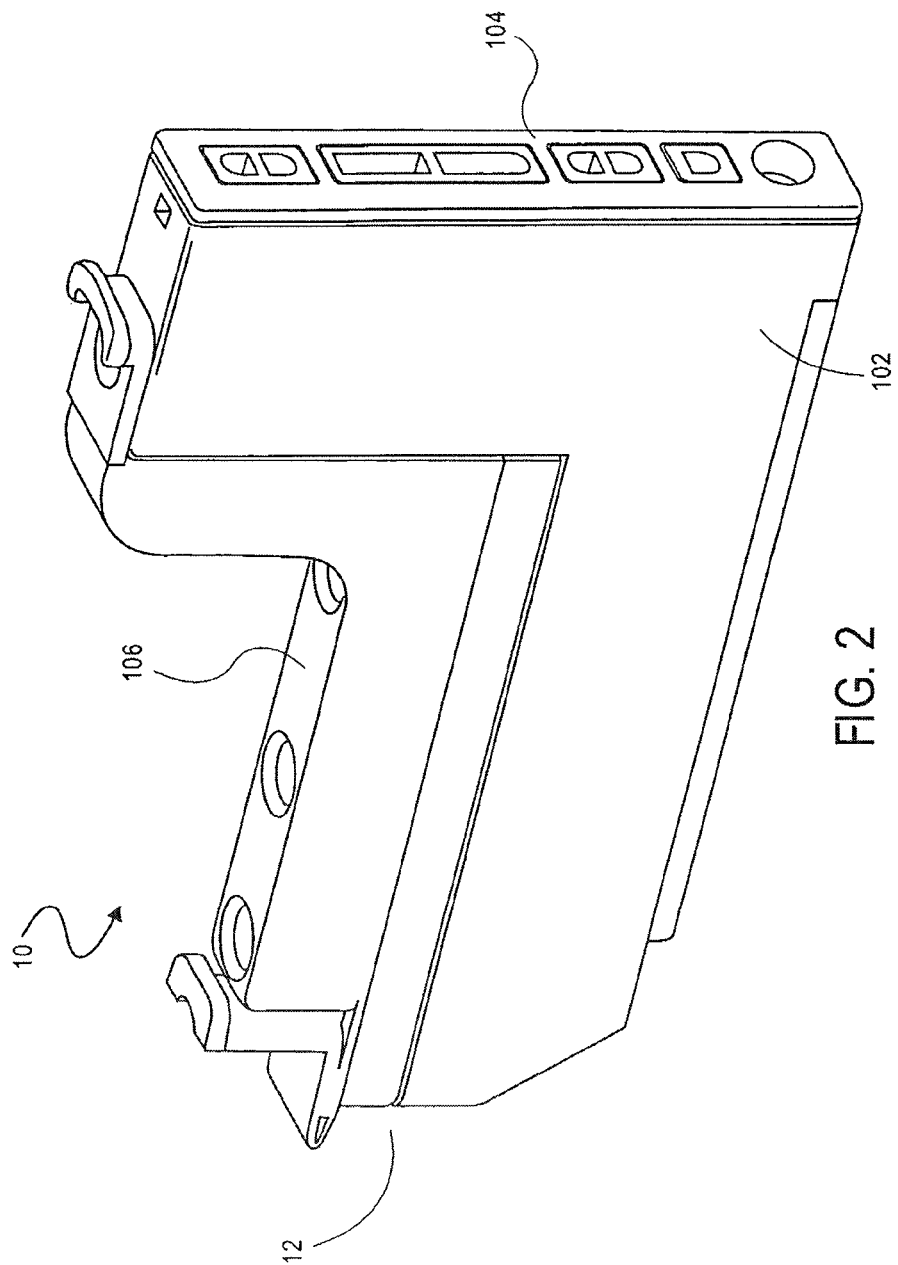
FIG. 2 is a perspective view of a cassette for preparing samples according to an embodiment of the invention.

With reference to FIG. 2, as described above, the cassette 10 includes a housing 12. The housing 12 includes a first assembly component 102, a second assembly component 104 and a third assembly component 106.

The first assembly component 102 includes the mixing chamber 14, the washing chambers 38 and 40, the elution chamber 42 and the first stationary piece 86 of each of the valves 32, 34 and 36. The first assembly component 102 also includes attachment parts 108, 110 (see FIG. 1) at one of its ends and an attachment piece 112 (see FIG. 1).

The second assembly component 104 includes the holding chambers 16, 18, 20 and 22 and an opening for receiving the first pump 44. The second assembly component 104 also includes attachment receiving parts 114, 116 (see FIG. 1).

The third assembly component 106 includes openings for receiving the second, third and fourth pumps 46, 48 and 50, respectively, and includes lids 52 and 54.

The cassette 10 is assembled by inserting the attachment components 108, 110 of the first assembly component 102 into the attachment receiving components 114, 116 of the second assembly component 104, respectively. The third assembly component 106 is then secured to the first assembly component using the attachment piece 112, thereby forming the assembled cassette 10, as illustrated in FIG. 2. The plungers 24, 26, 28 and 30, pumps 44, 46, 48 and 50, and the second moveable piece 88 of each of the valves 32, 34 and 36, are inserted into the cassette 10.

Figure 3:
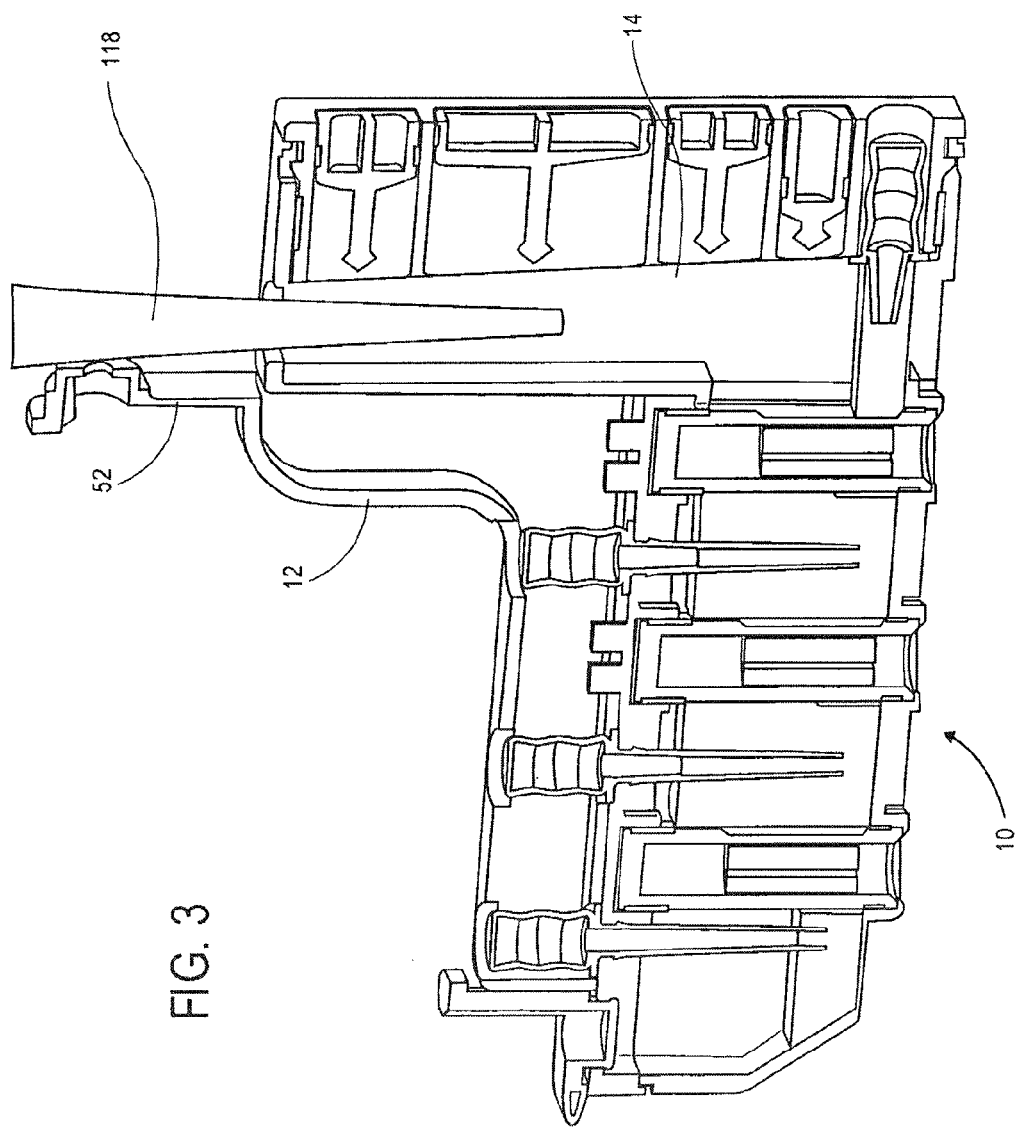
FIG. 3 is a cross-sectional side view showing a sample being placed into the cassette using a pipette, according to an embodiment of the invention.

In use, as shown in FIG. 3, the first lid 52 is removed to provide access to the opening 70 of the mixing chamber 14. A sample of cells is placed into an assembled cassette 10 using a pipette 118. The cells in the sample include nucleic acid. The pipette 118 having the sample therein is placed in the mixing chamber 14. The sample is released from the pipette 118.

Figure 4:
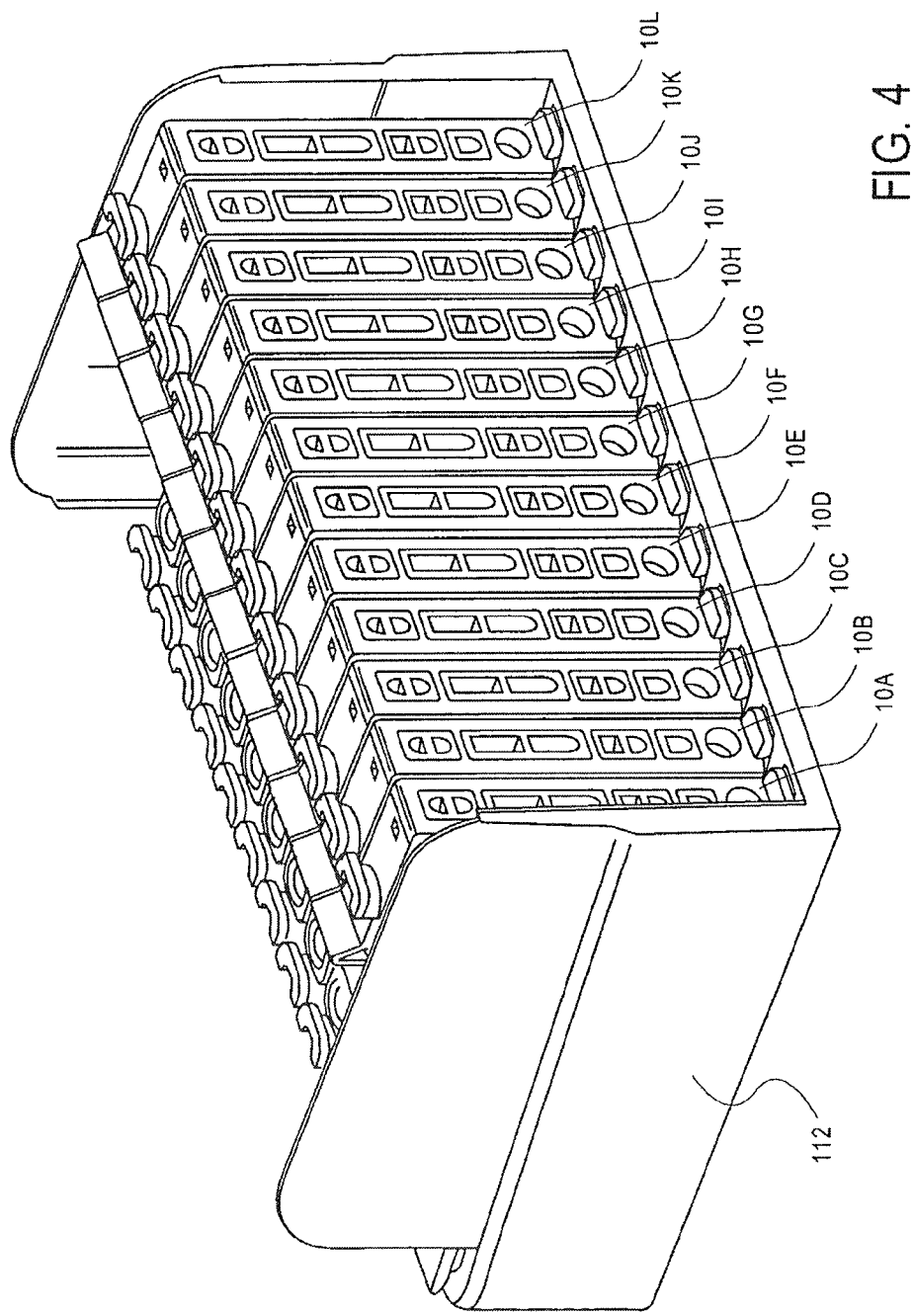
FIG. 4 is a perspective view of a magazine, in which the cassette of FIG. 1 is used, according to an embodiment of the invention.

As shown in FIG. 4, the cassette 10 is closed by closing the first lid 52. The cassette 10 is then placed together with similar cassettes 10 into a magazine 120, or rack, for containing a series of cassettes 10.

Figure 5:
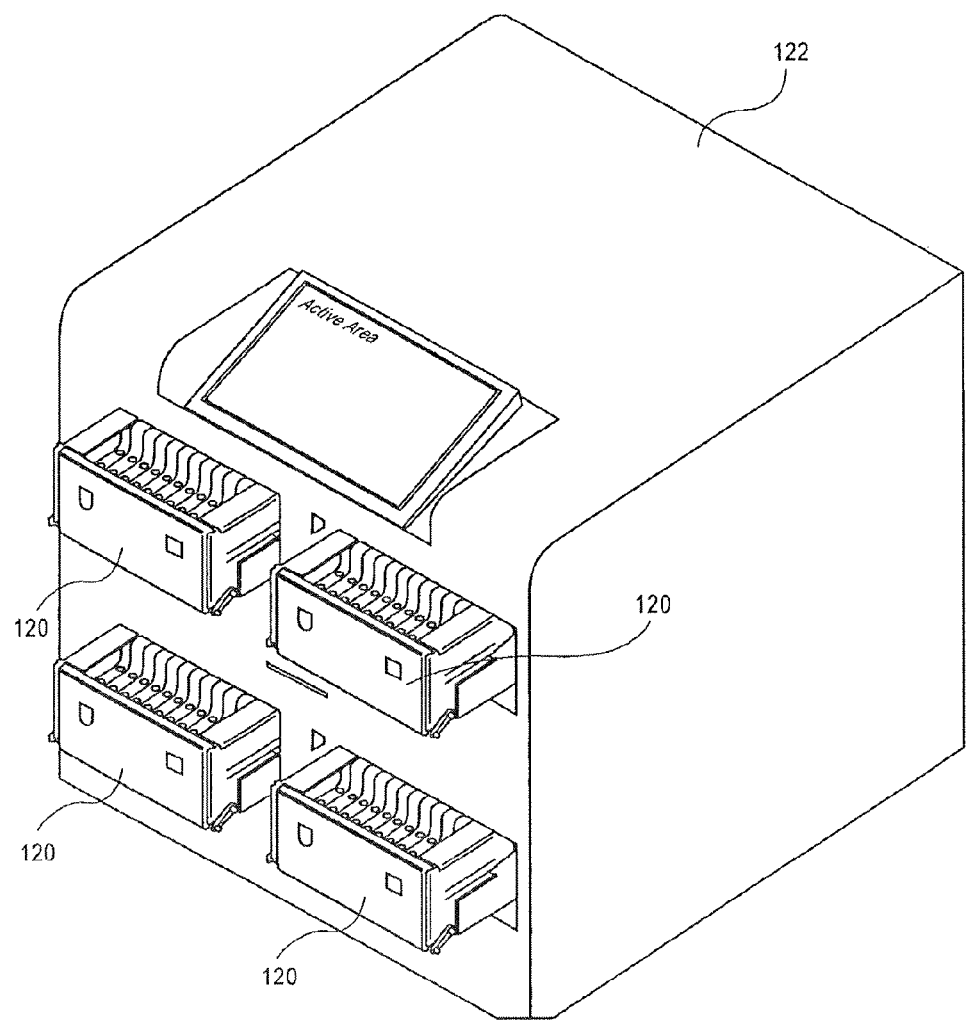
FIG. 5 is a perspective view of an instrument, in which the magazine of FIG. 4 is used, according to an embodiment of the invention.

As shown in FIG. 5, the magazine 120 is placed into an instrument 122. A protocol may be selected for preparing the sample in the cassette 10 in the instrument 122.

Figure 6:
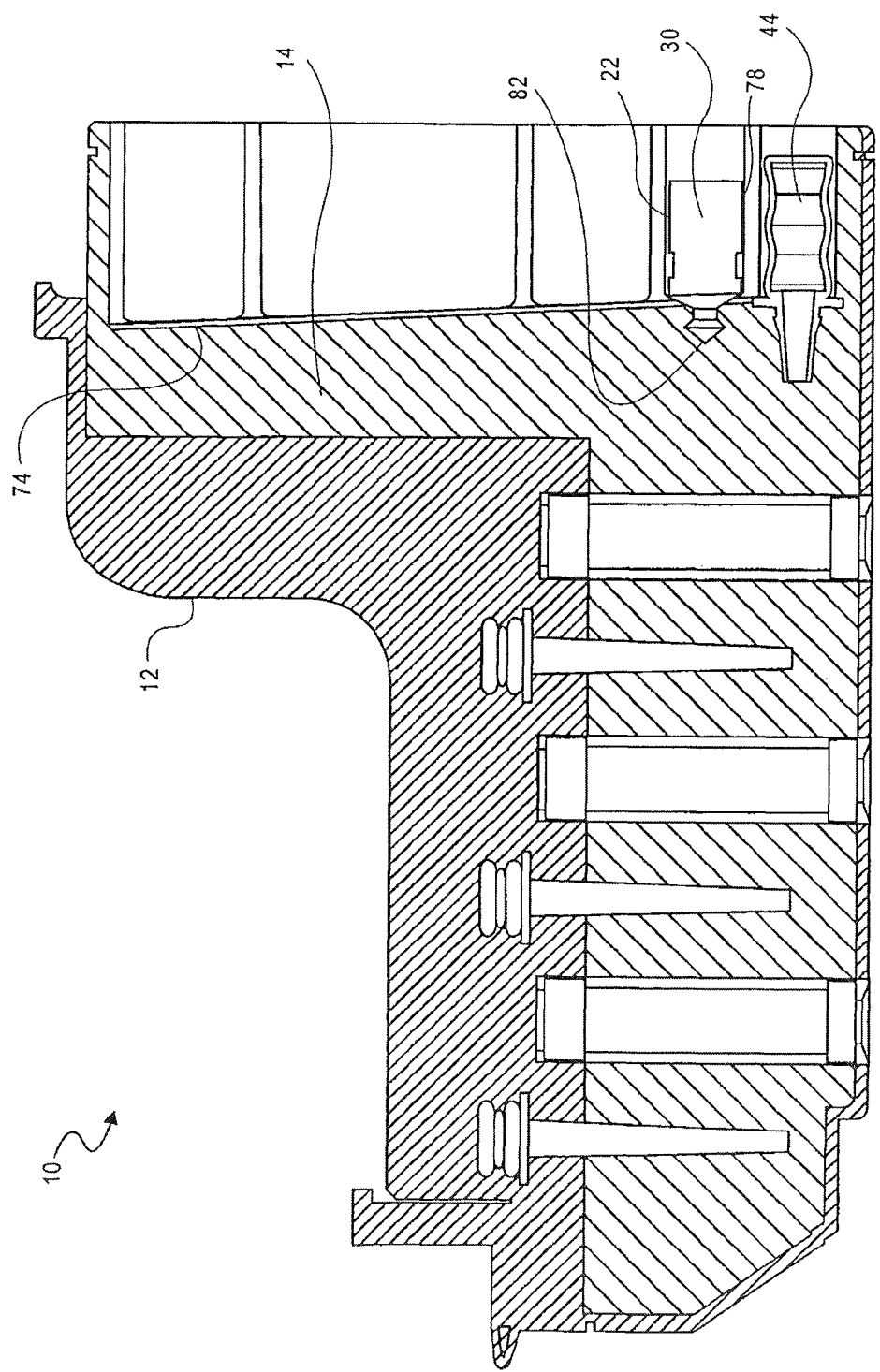
FIG. 6 is a cross-sectional side view of the cassette of FIG. 1, showing the transfer of a PK solution into a mixing chamber, according to an embodiment of the invention.

As shown in FIG. 6, the PK solution is added to the sample. The PK solution is added by moving the plunger 30 in the fourth holding chamber 22. A force is applied to the base 78 of the plunger 30 to move the plunger 30. As the piercing element 82 of the plunger 30 advances toward the mixing chamber 14, the piercing element 82 punctures and ruptures the thin film 74. The break in the thin film 74 provides access to the mixing chamber 14. Continued motion of the plunger 30 transfers the contents (e.g., PK solution) of the first holding chamber 22 into the mixing chamber 14.

The PK solution is mixed with the sample by pumping the mixture with the first pump 44. The PK solution destroys the walls of the cells of the sample, creating bulk material and nucleic acid in the bulk material.

Figure 7:
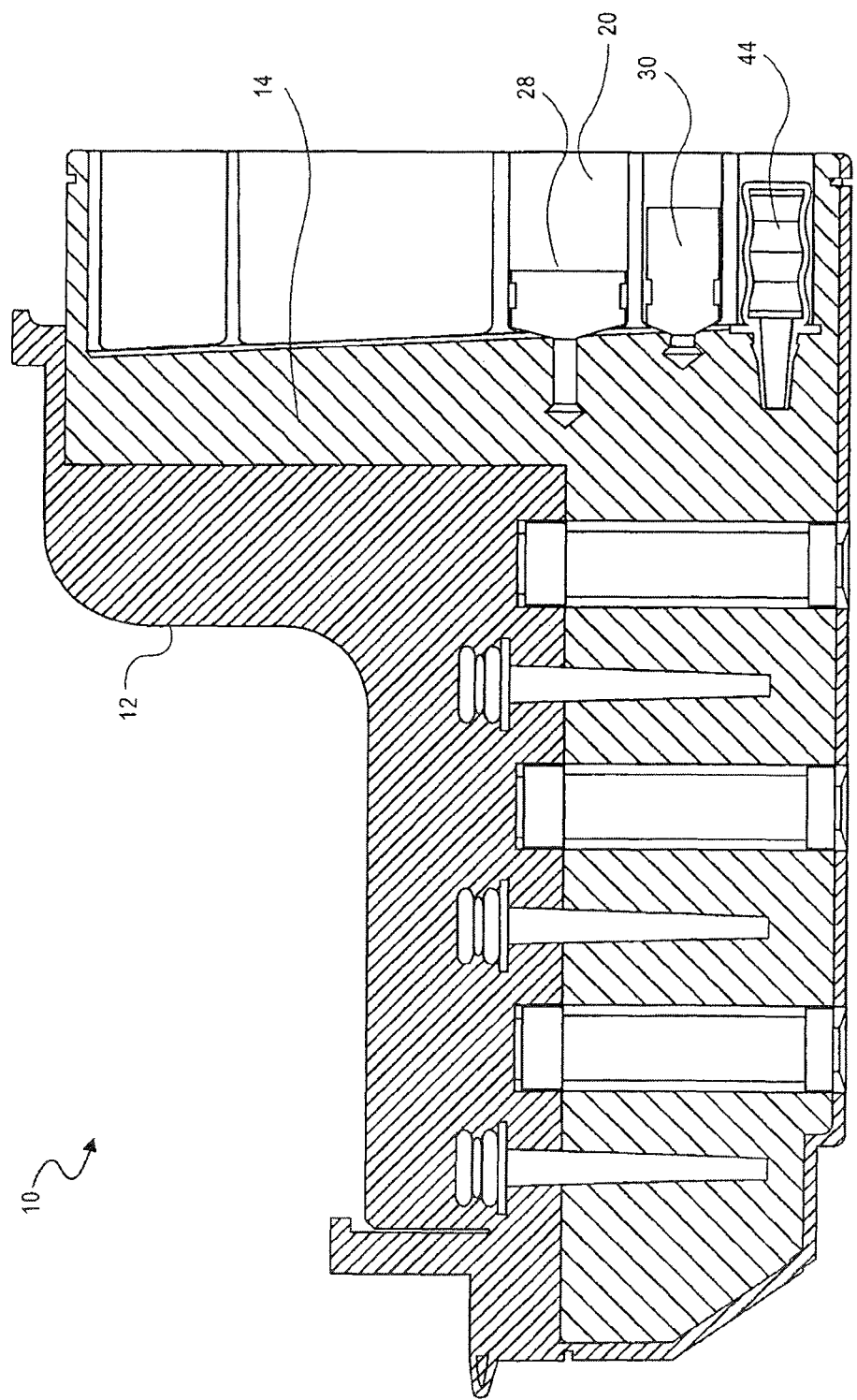
FIG. 7 is a cross-sectional side view of the cassette of FIG. 1, showing the transfer of a lysis solution into a mixing chamber, according to an embodiment of the invention.

As shown in FIG. 7, the lysis solution is added to the sample. Plunger 28 operates in the same manner as plunger 30 to transfer the lysis solution in the third holding chamber 20 into the mixing chamber 14. The sample is pumped to mix the lysis buffer with the PK solution and sample of cells. The lysis solution is typically a salt or detergent. The lysis solution is used to solulibize the bulk material. The lysis solution typically does not solulibize proteins.

The heating element 56 may be used to heat the lysis solution and sample. The heating element 56 may be controlled by the instrument 122. As described hereinabove, the temperature of the heating element 56 may be variable, and is selected to optimize the effectiveness of the lysis solution.

Figure 8:
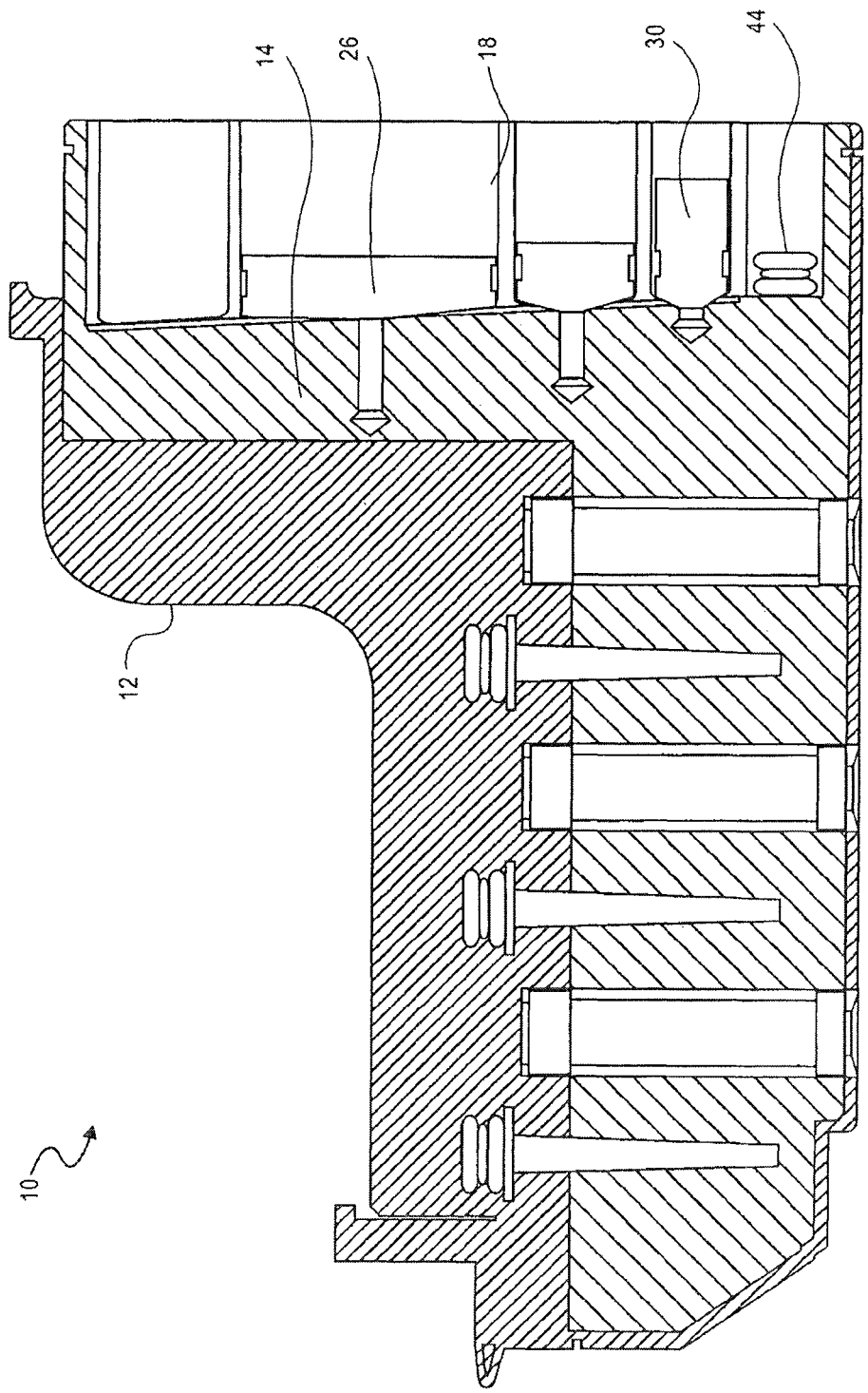
FIG. 8 is a cross-sectional side view of the cassette of FIG. 1, showing the transfer of a binding solution into a mixing chamber, according to an embodiment of the invention.

As shown in FIG. 8, the binding solution is added to the sample, PK solution and lysis buffer solution. Plunger 26 operates in the same manner as plunger 30 to transfer the binding solution in the second holding chamber 18 into the mixing chamber 14. The solution is pumped to mix the binding solution with the PK solution, lysis solution and sample. The binding solution is typically hydrophobic and increases salt in the solution. The binding solution causes the nucleic acid to be magnetically charged.

Figure 9:
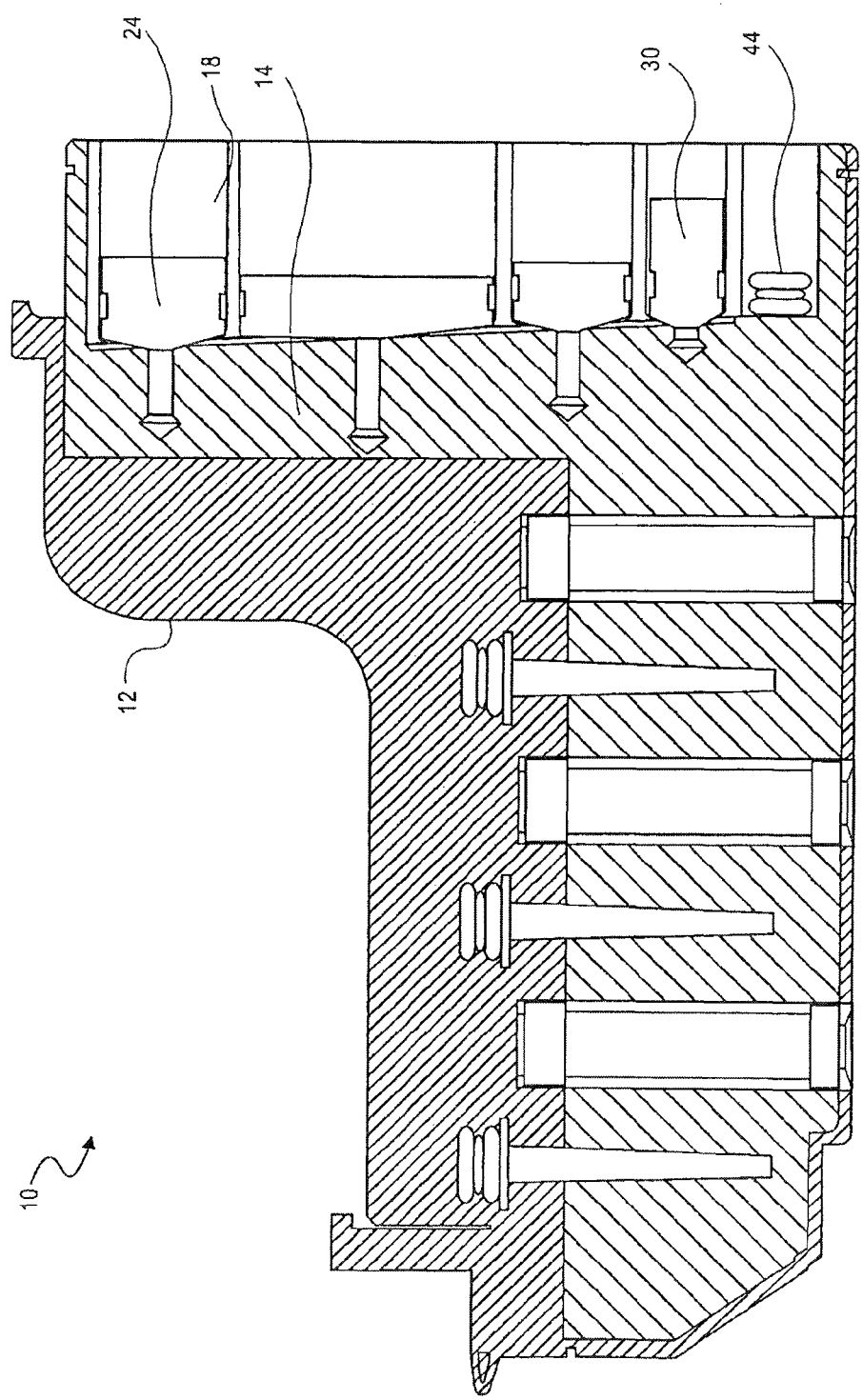
FIG. 9 is a cross-sectional side view of the cassette of FIG. 1, showing the transfer of metallic beads into the mixing chamber, according to an embodiment of the invention.

As shown in FIG. 9, the magnetic beads are added to the solution and pumped for about two minutes. Plunger 24 operates in the same manner as plunger 30 to transfer the lysis solution in the first holding chamber 18 into the mixing chamber 14. The magnetic beads bind to the magnetically charged nucleic acid.

Figure 10:
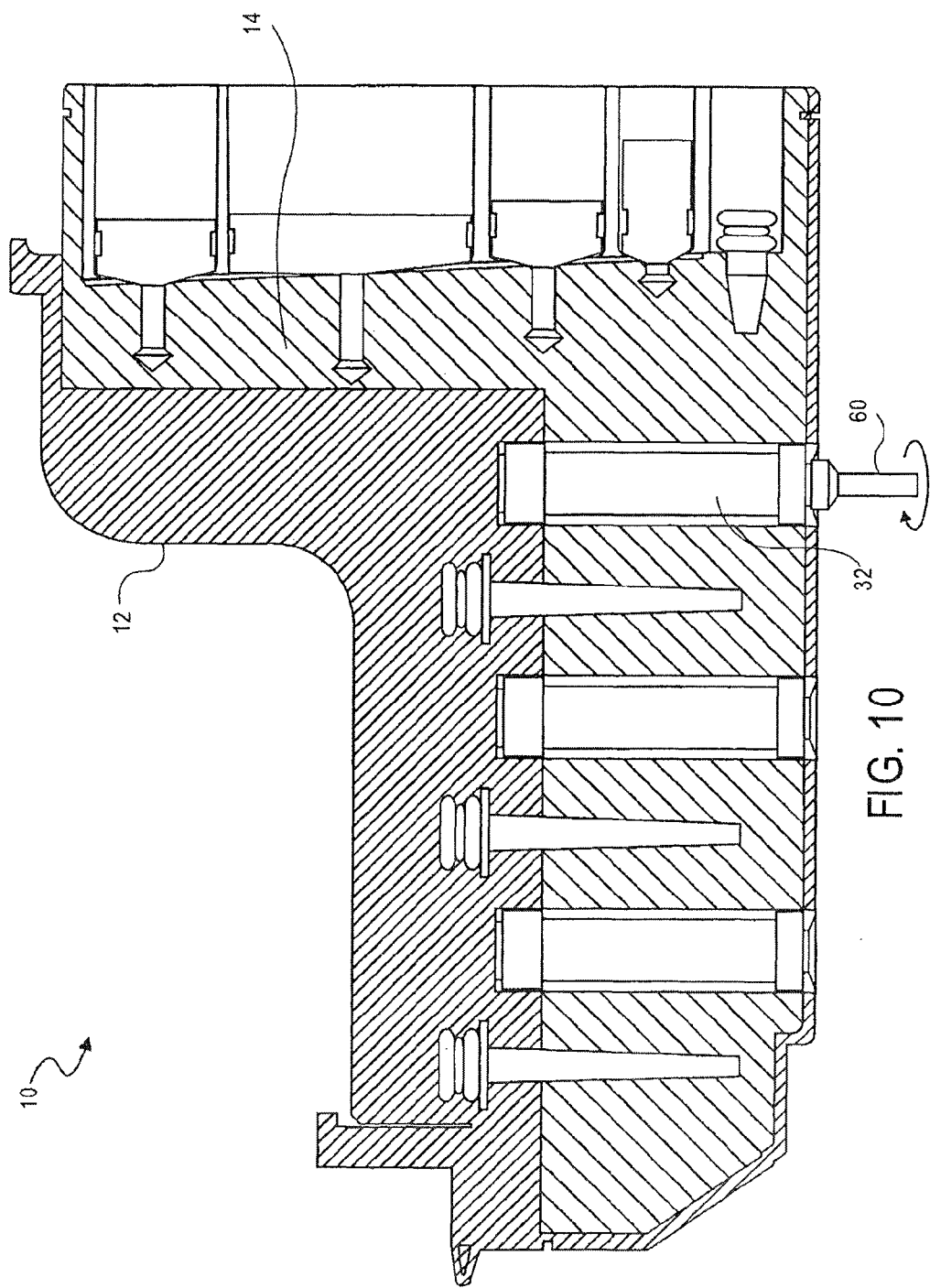
FIG. 10 is a cross-sectional side view of the cassette of FIG. 1, showing metallic beads bound to a first valve, according to an embodiment of the invention.

As shown in FIG. 10, the magnetic beads, together with the nucleic acid, are bound to the first valve 32. The removable positionable magnet 60 is placed in the first valve 32 and slid to a position in the first valve 32 to attract the magnetic beads, which are bound to the nucleic acid, from the mixing chamber 14 to the first valve 32.

Figure 11:
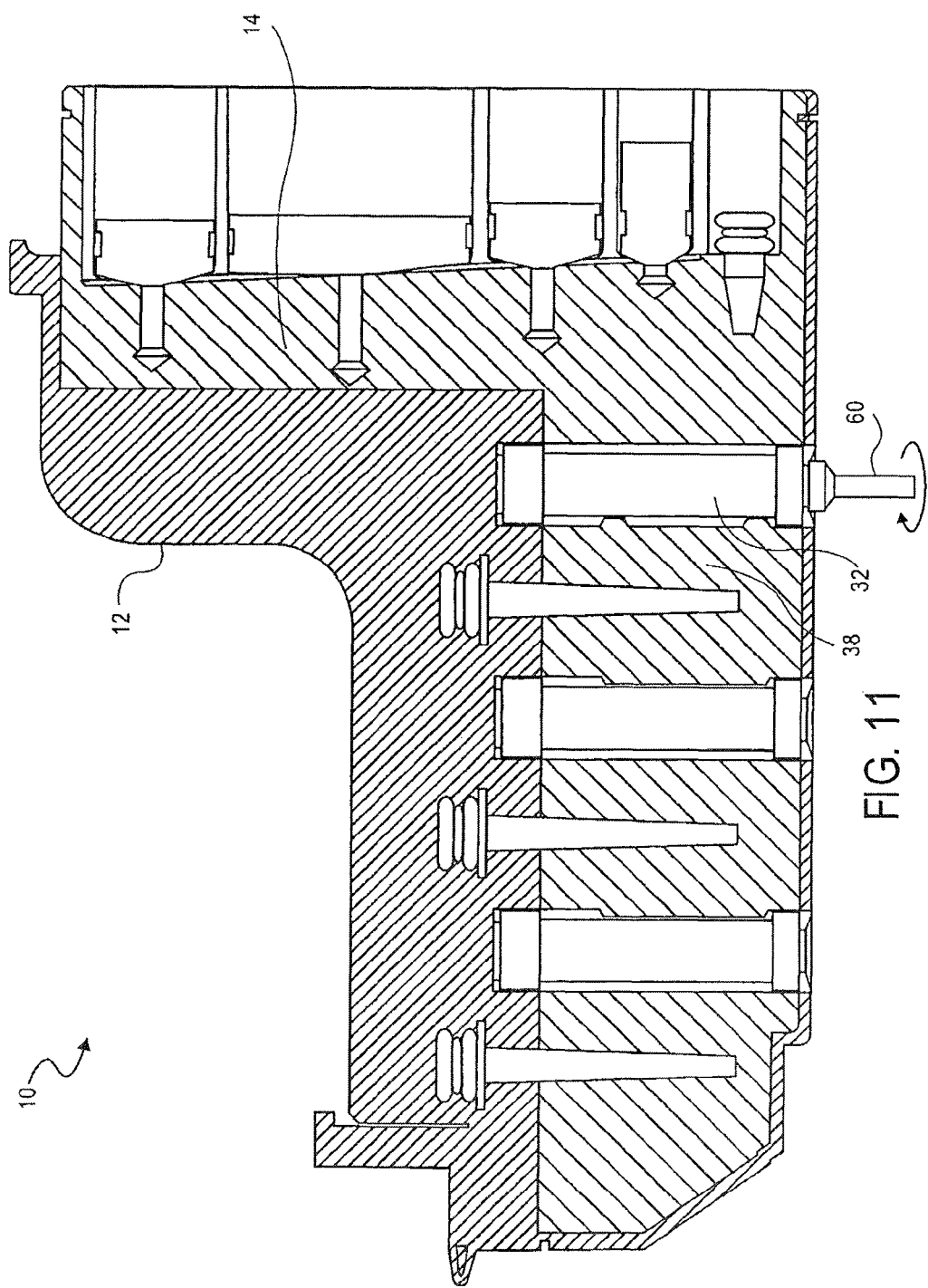
FIG. 11 is a cross-sectional side view of the cassette of FIG. 1, showing the transfer of metallic beads from a mixing chamber to a washing chamber, according to an embodiment of the invention.

As shown in FIG. 11, the magnetic beads, together with the nucleic acid, are then moved from the mixing chamber 14 and received in the first washing chamber 38.

Figure 12:
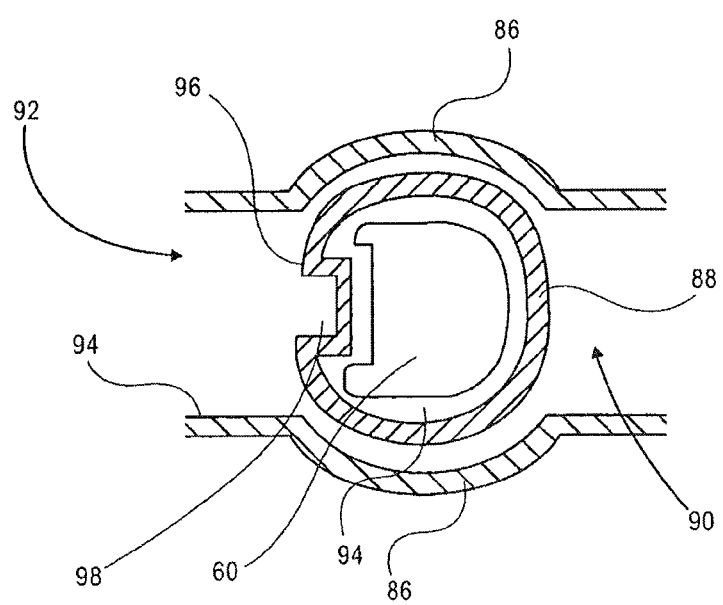
FIG. 12 is a perspective end view of a valve for use in the cassette of FIG. 1 according to an embodiment of the invention.

FIG. 12 is a detailed view of the valves 32, 34, 36 illustrating the movement of the magnetic beads from the mixing chamber 14 to the first washing chamber 38. As discussed above each of the valves 32, 34 and 36 include a first stationary piece 86 and a second moveable piece 88, the second piece 88 being moveable relative to the first piece 86.

The magnet 60 is inserted into the opening 94 of the second piece 88. The magnet 60 is inserted to a position corresponding to the openings 90 and 92 of the first piece 86. The magnet 60 attracts the magnetic beads from the mixing chamber 14 through the opening 90 in the first piece 86 and into the cavity 98 in the second piece 88. The second piece 88 is rotated such that the magnetic beads are sealed in the cavity 98 of the second piece 88, between surfaces of the second piece 88 and the first piece 86. The second piece 88 is rotated past the surface 94 of the first piece 86, such that the cavity 98 is accessible in the opening 92 of the first piece 86. The magnet 60 is then removed from the opening 94 in the second piece 88 to release the magnetic beads from the cavity 98 in the second piece 88.

Figure 13:
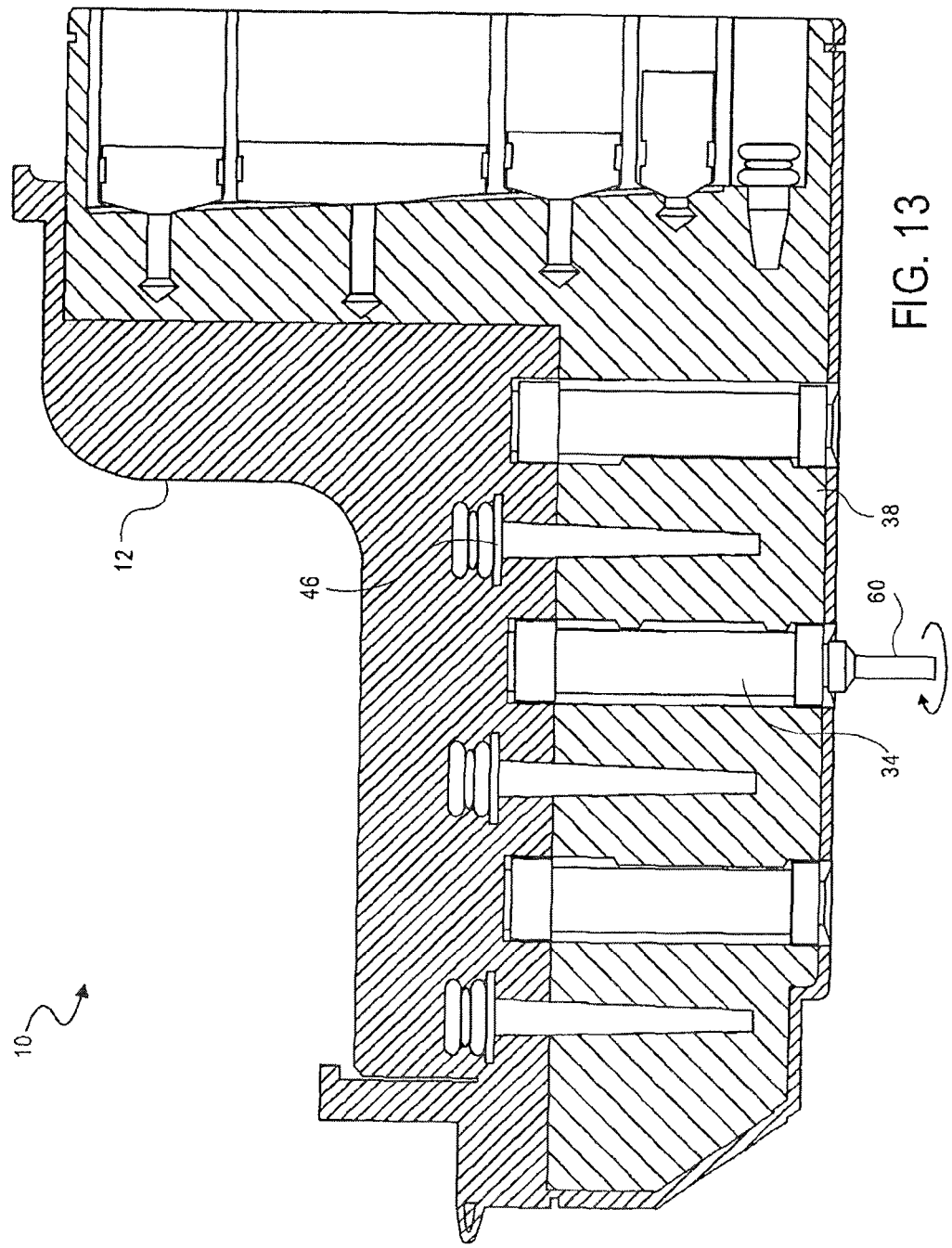
FIG. 13 is a cross-sectional side view of the cassette of FIG. 1, showing metallic beads bound to a second valve, according to an embodiment of the invention.

As shown in FIG. 13, the magnetic beads and nucleic acid are then washed with the washing solution by pumping the solution with the second pump 46. The magnetic beads, together with the nucleic acid, are then bound to the second valve 34 by inserting the magnet 60 into the second valve 34, as described above with reference to FIG. 12.

Figure 14:
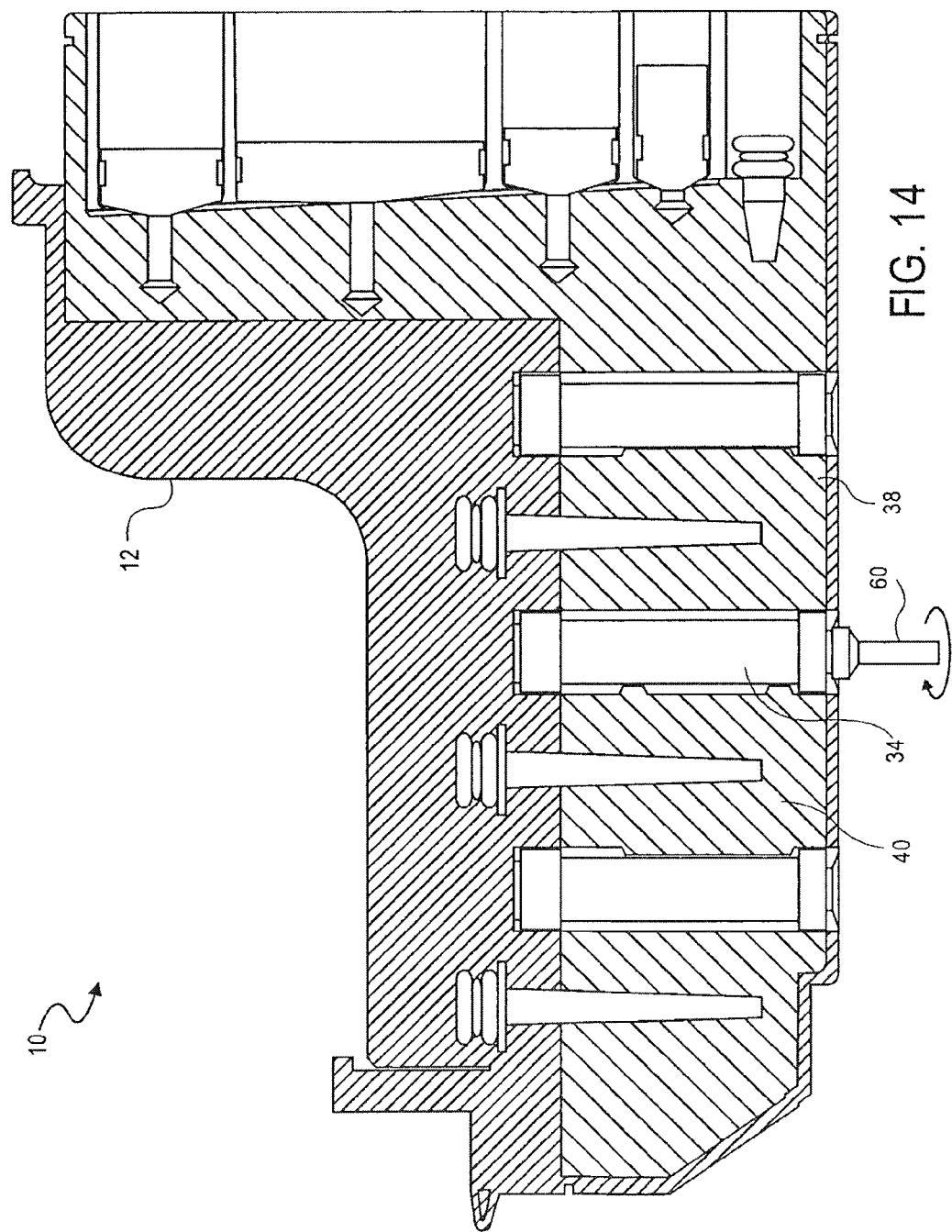
FIG. 14 is a cross-sectional side view of the cassette of FIG. 1, showing the transfer of metallic beads from a first washing chamber to a second washing chamber, according to an embodiment of the invention.

As shown in FIG. 14, the magnetic beads, together with the nucleic acid, are then moved from the first washing chamber 38 to the second washing chamber 40 using the second valve 34. The second valve 34 transfers the magnetic beads and nucleic acid from the first washing chamber 38 to the second washing chamber 40, as described above with reference to FIG. 12.

Figure 15:
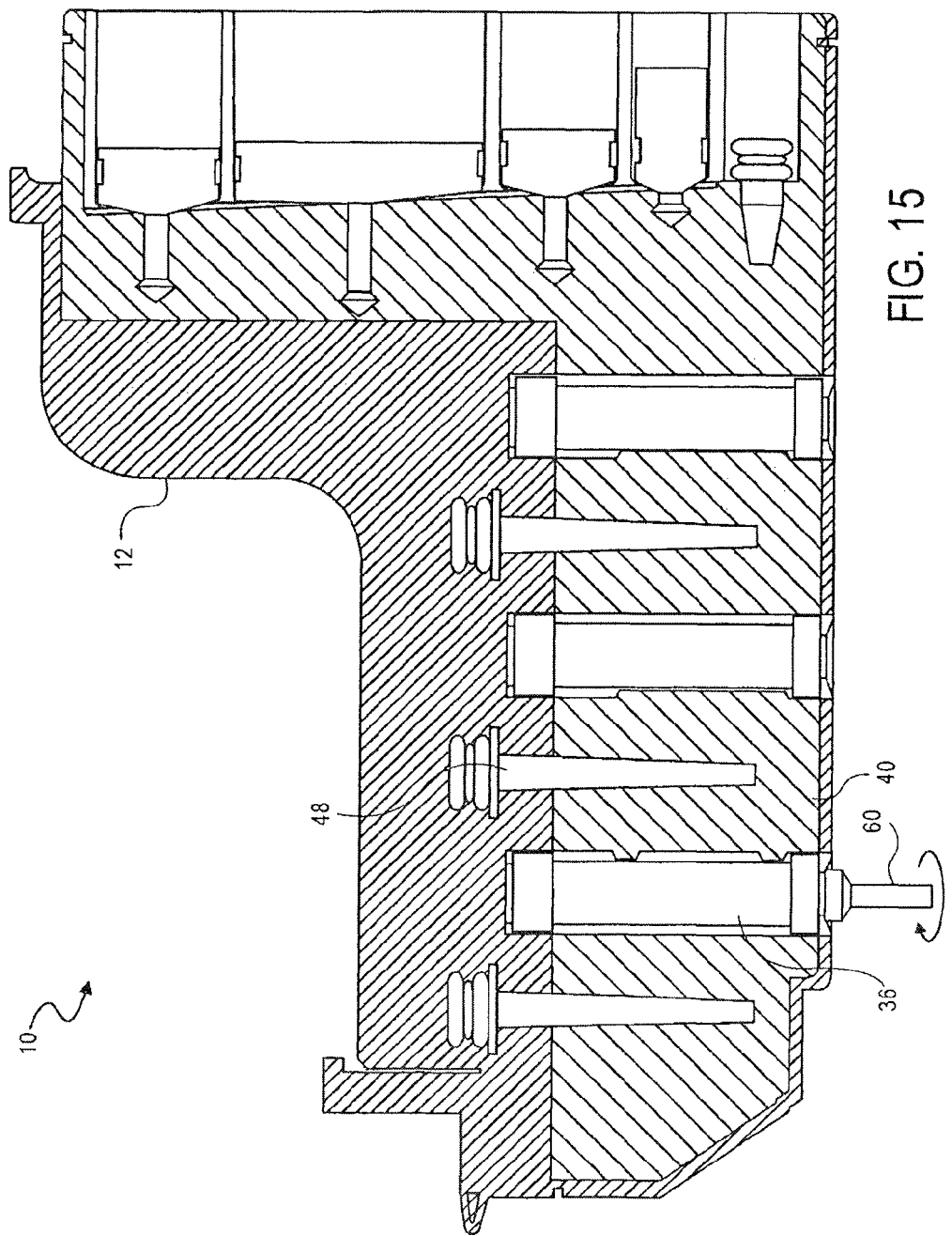
FIG. 15 is a cross-sectional side view of the cassette of FIG. 1, showing metallic beads bound to a third valve, according to an embodiment of the invention.

As shown in FIG. 15, the magnetic beads and nucleic acid are then washed with the washing solution a second time by pumping the solution with the third pump 48. The magnetic beads, together with the nucleic acid, are then bound to the third valve 36 by positioning the magnet 60 in the third valve 36, as described above with reference to FIG. 12.

Figure 16:
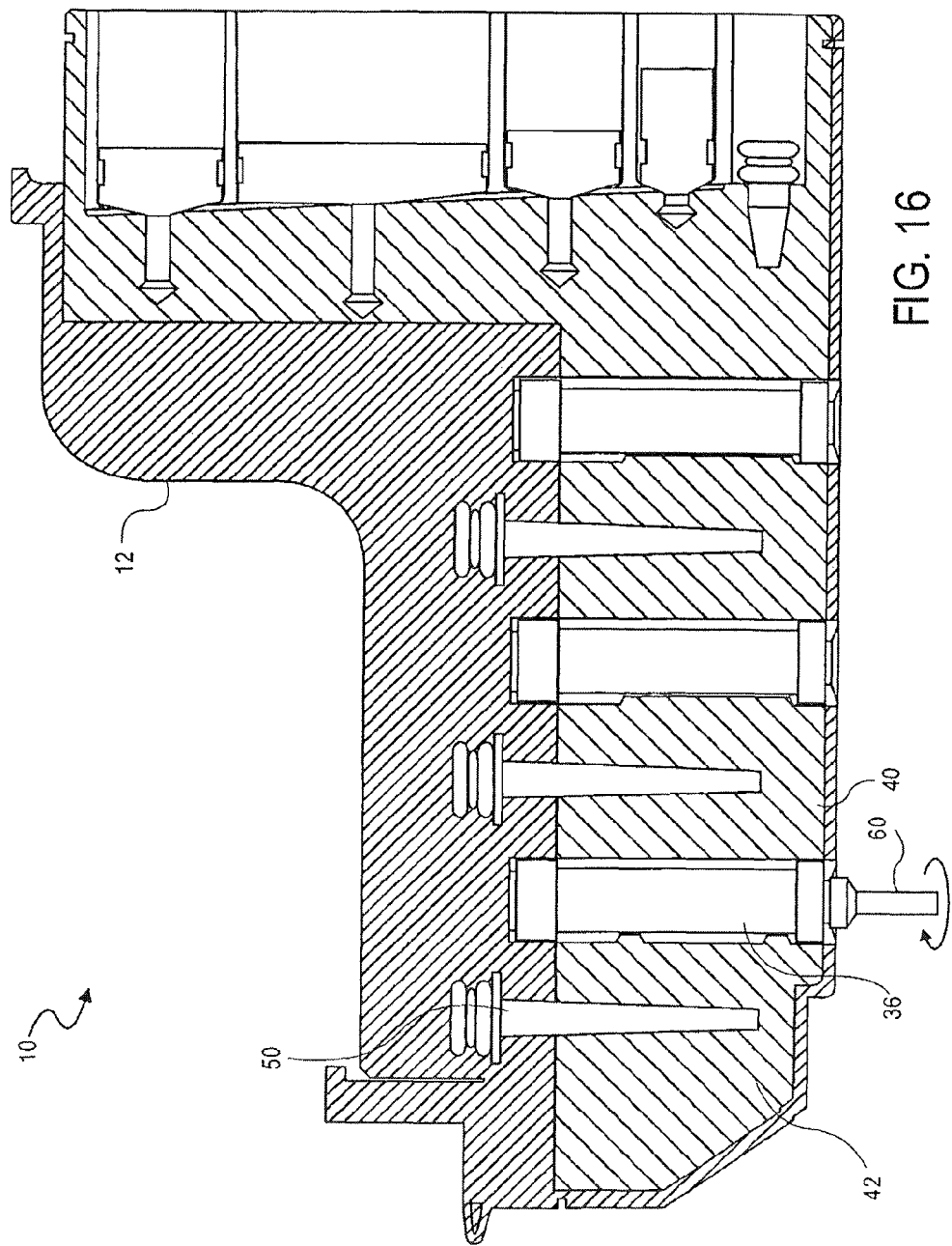
FIG. 16 is a cross-sectional side view of the cassette of FIG. 1, showing the transfer of metallic beads from a second washing chamber to an elution chamber, according to an embodiment of the invention.

As shown in FIG. 16, the magnetic beads and nucleic acid are then moved from the second washing chamber 40 to the elution chamber 42. The magnetic beads and nucleic acid are transferred from the second washing chamber 40 to the elution chamber 42 using the procedure described above with reference to FIG. 12.

An elution buffer solution is then mixed with the magnetic beads and nucleic acid by pumping the solution with the fourth pump 50. The heating element 58 may be used to heat the elution buffer, magnetic beads and nucleic acid. The heating element 58 may be controlled by the instrument 122. The temperature may be variable and may be selected to optimize release of the nucleic acid from the magnetic beads.

The magnetic beads alone are then bound again to the third valve 36 by positioning the magnet 60 in the third valve 36 as described above with reference to FIG. 12.

Figure 17:
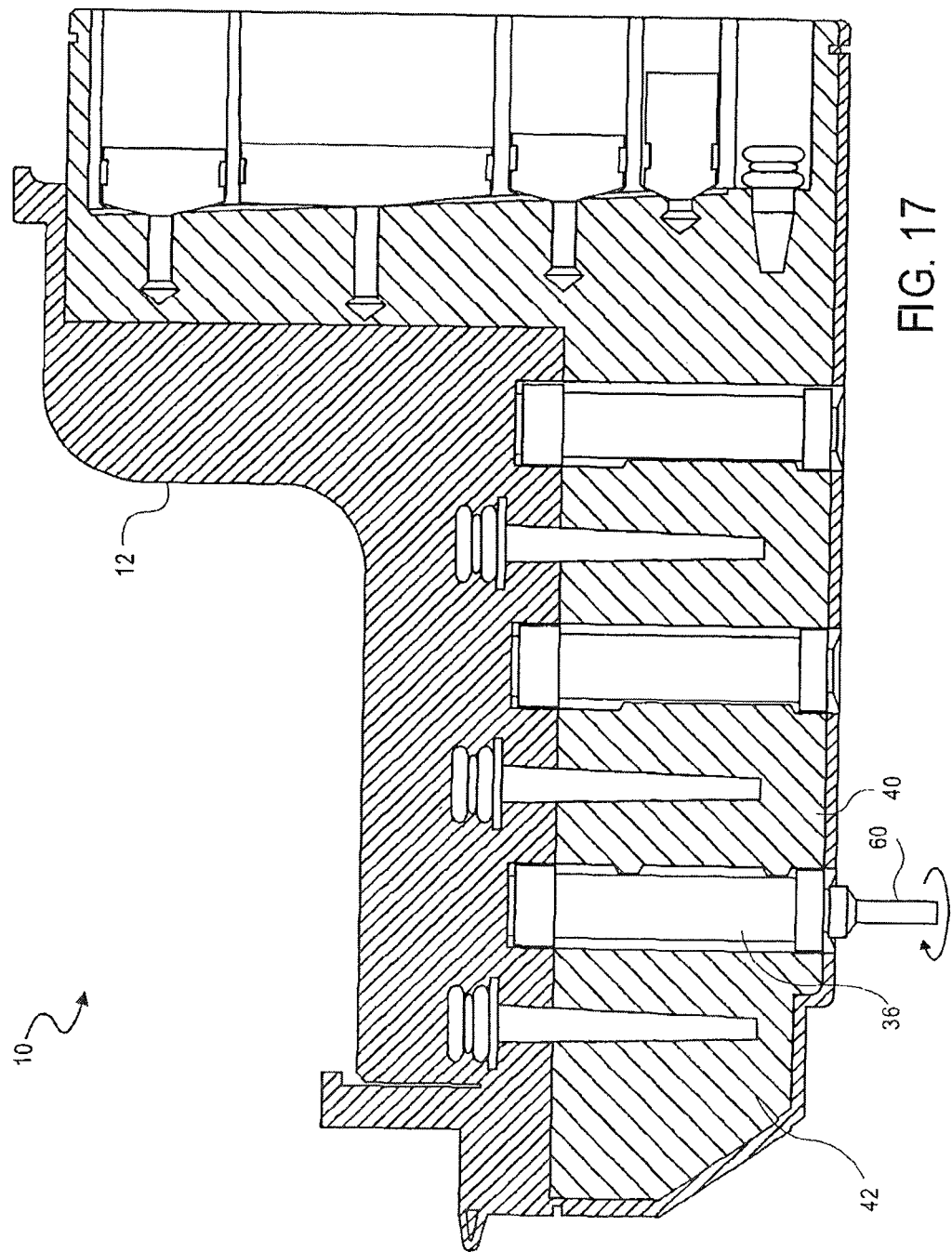
FIG. 17 is a cross-sectional side view of the cassette of FIG. 1, showing transfer of metallic beads from an elution chamber to a second washing chamber, according to an embodiment of the invention.

As shown in FIG. 17, the magnetic beads alone are then moved from the elution chamber 42 back into the second washing chamber 40, leaving the nucleic acid in the elution chamber 42. The magnetic beads are transferred from the elution chamber 42 to the second washing chamber 40 using the procedure described above with reference to FIG. 12.

Figure 18:
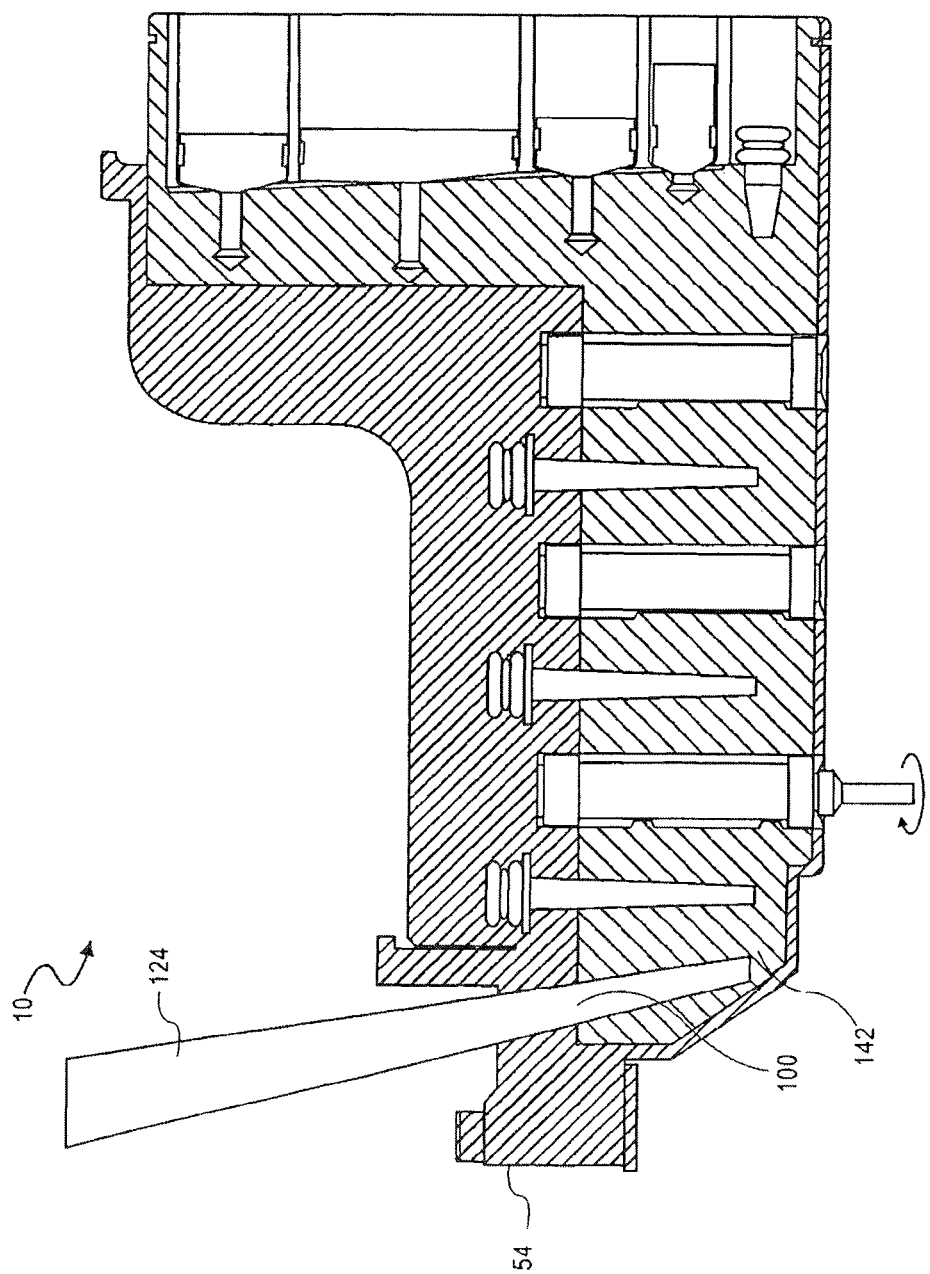
FIG. 18 is a cross-sectional side view of the cassette of FIG. 1, showing removal of a prepared sample from an elution chamber, according to an embodiment of the invention.

As shown in FIG. 18, the prepared sample of nucleic acid may be accessed using a second pipette 124. The second lid 54 is removed to provide access to the opening 100 in the elution chamber 42. The pipette 124 is inserted into the opening 100 and the prepared sample of nucleic acid is withdrawn.

Figure 19:
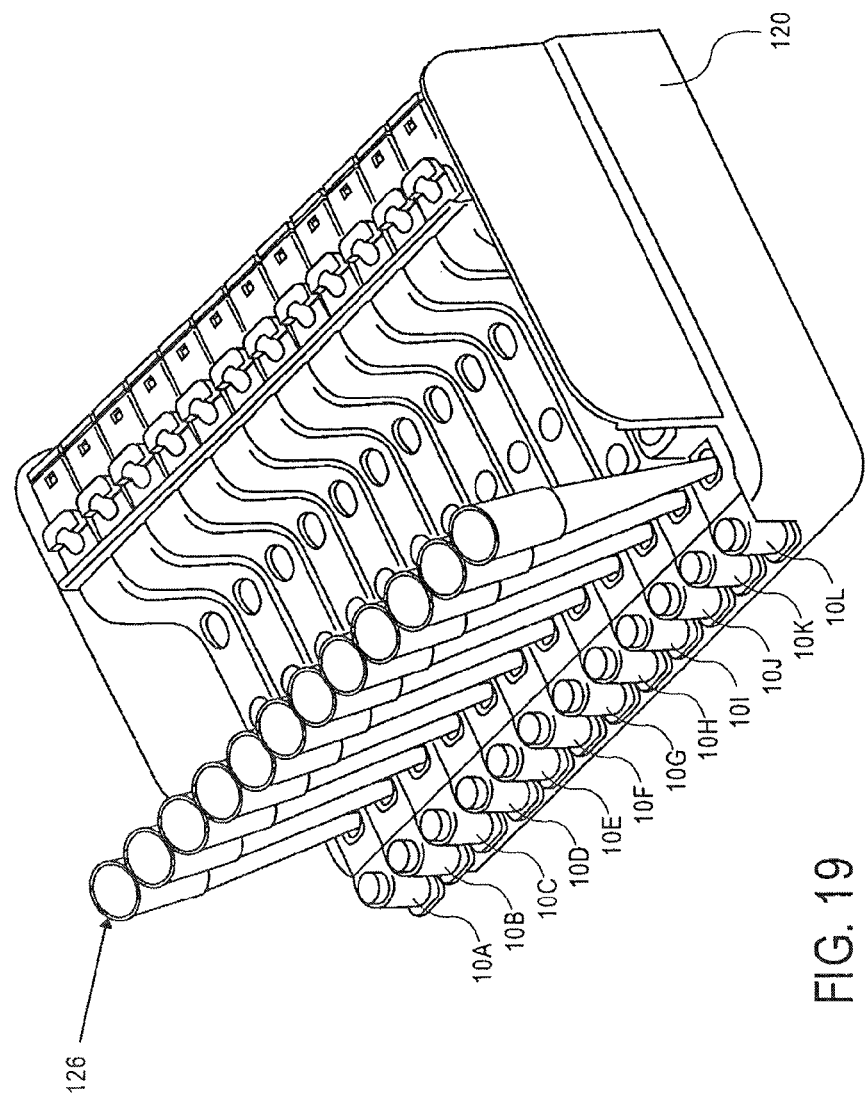
FIG. 19 is a perspective view of a magazine in which a multi-channel pipette is used to access a plurality of samples from a plurality of cassettes.

As shown in FIG. 19, a multi-channel pipette 126 may be used to access a plurality of samples from a plurality of cassettes 10.

Figure 20:
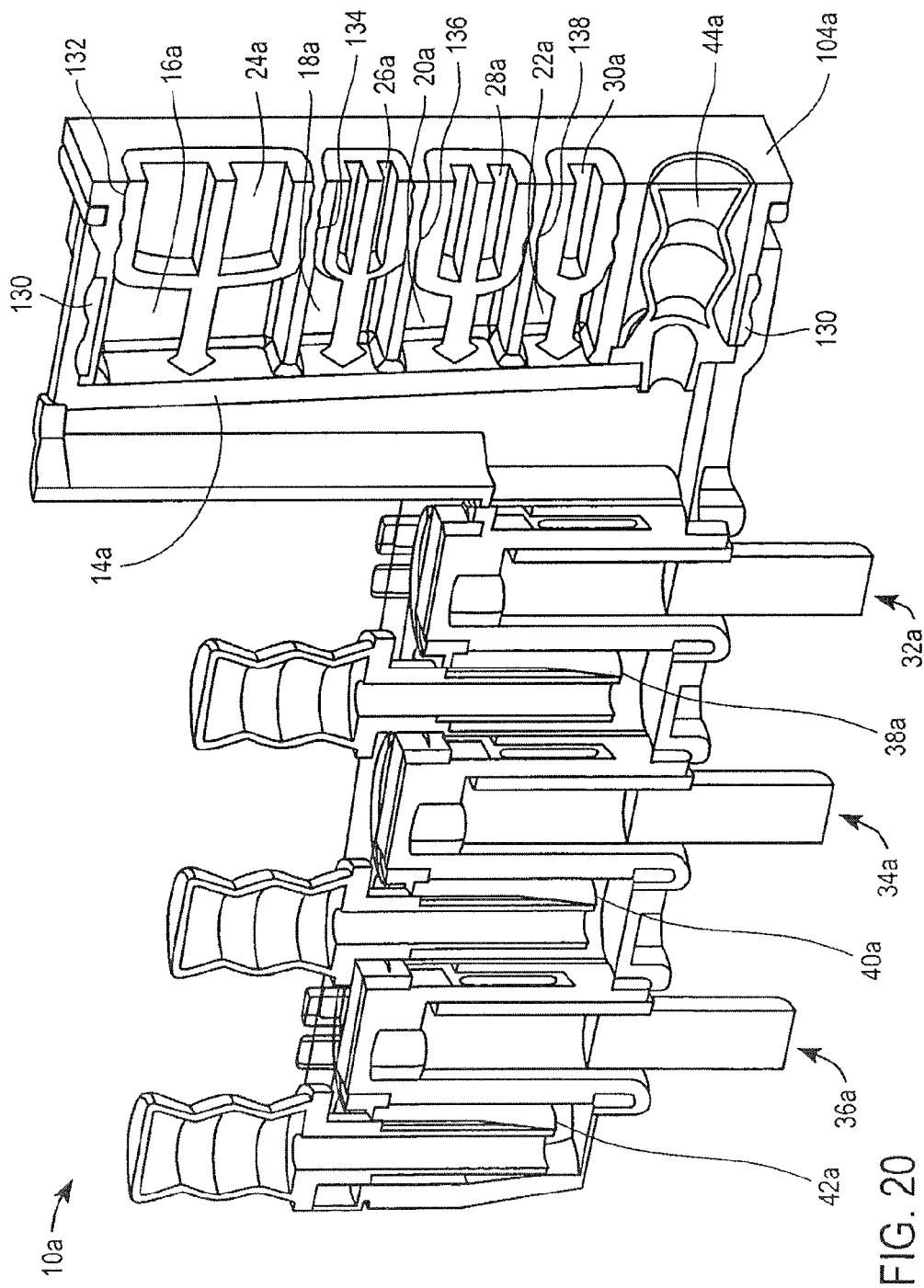
FIG. 20 is a cross-sectional perspective view of an alternative embodiment of the cassette of FIG. 1 according to an embodiment of the invention.

FIG. 20 illustrates an alternative embodiment of the cassette 10. The cassette 10a illustrated in FIG. 20 differs from the cassette 10 illustrated in FIG. 1 in that the assembly component 104a includes a seal 130, the plungers 24a, 26a, 28a and 30a each include seals 132, 134, 136 and 138, respectively, and the valves 32a, 34a and 36a have a different arrangement, as discussed hereinafter.

Figure 21:
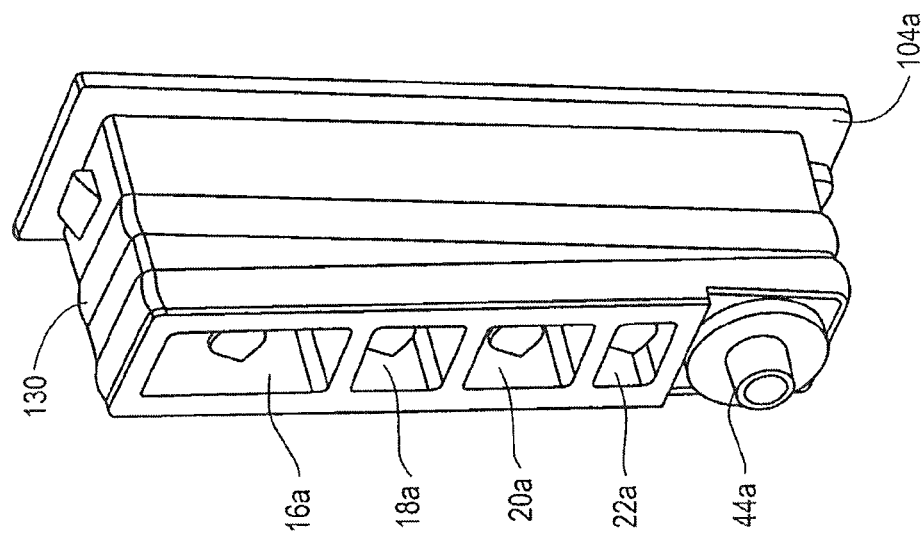
FIG. 21 is a detailed perspective view of an assembly component of the cassette of FIG. 20 according to an embodiment of the invention.

FIG. 21 illustrates the assembly component 104a in more detail. The assembly component 104a includes a seal 130. The illustrated seal 130 is a double elastomer, which extends along the circumference of the assembly component 104a.

Figure 22:
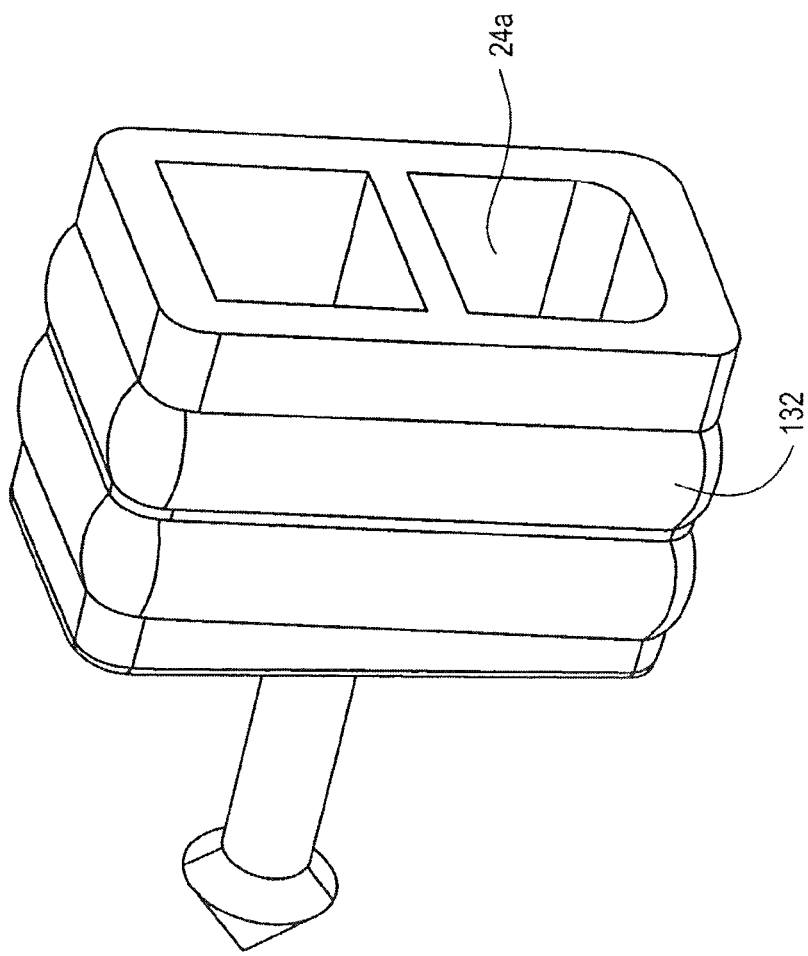
FIG. 22 is a detailed perspective view of a plunger of the cassette of FIG. 20 according to an embodiment of the invention.

FIG. 22 illustrates the plunger 24a in more detail. The plunger 24a includes a seal 132. The illustrated seal 132 is also a double elastomer, which extends along the circumference of the plunger 24a. It will be appreciated that each of plungers 26a, 28a and 30a may also have a similar arrangement.

Figure 23:
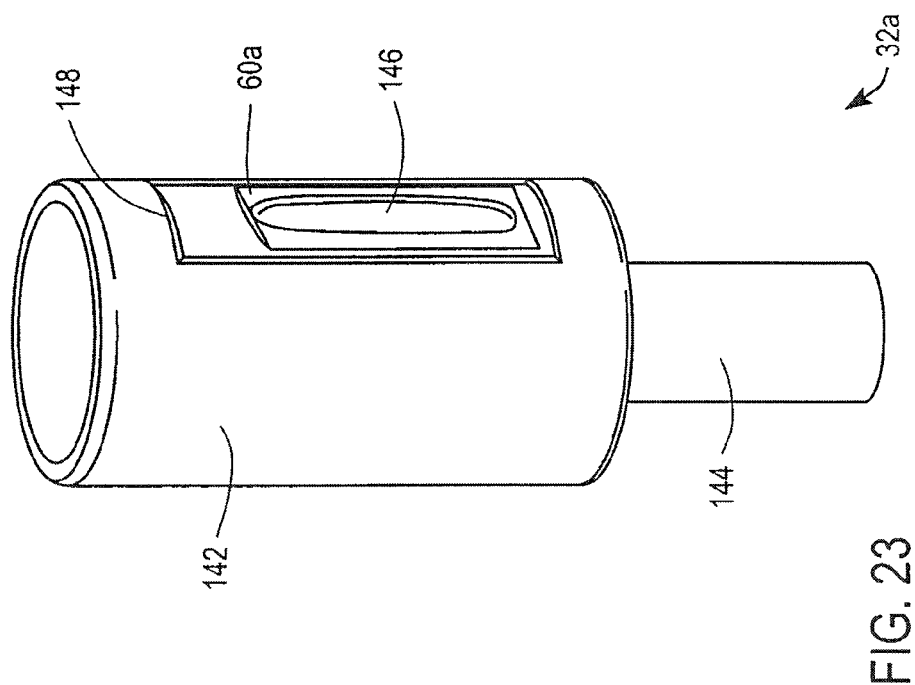
FIG. 23 is a detailed perspective view of a valve of the cassette according to an embodiment of the invention.
Figure 24:
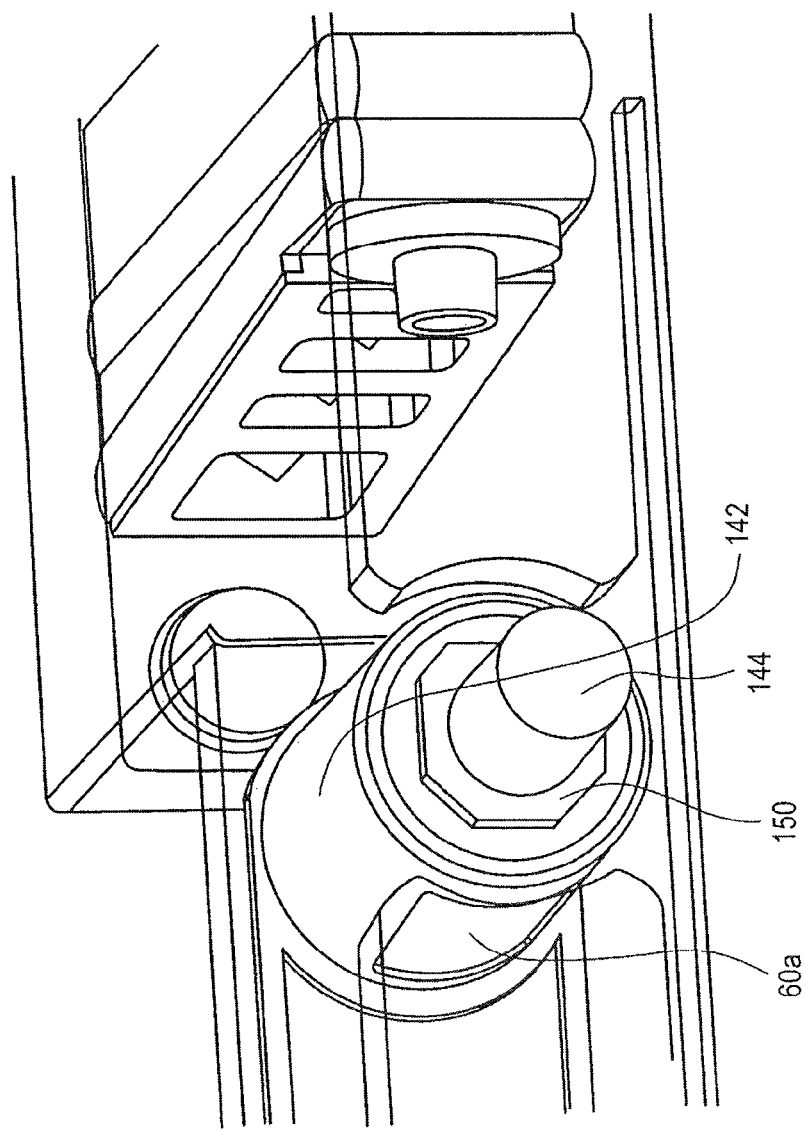
FIG. 24 is a detailed perspective view of the valve of FIG. 23 according to an embodiment of the invention.

FIGS. 23 and 24 illustrate the valve 32a in more detail. It will be appreciated that valves 34a and 36a also have a similar arrangement. The valve 32a includes a magnet 60a, a housing 142, and a shaft 144. The housing 142 includes a first opening (not shown) to receive the magnet 60a and a second opening 148 to expose the magnet 60a and receive the particles 146. The magnet 60a is shaped to correspond to the opening 148 and is selected to attract the particles 146. The housing 142 also includes a third opening (not shown) for receiving the shaft 144. As shown in FIG. 24, the shaft 144 may include a keyed element 150. The keyed element 150 is shaped to engage the cassette 10a. It will be appreciated that the shaft may be removable or an integrated element of the valve 32a. It will also be appreciated that the housing 142 may, alternatively, include the keyed element.

The shaft 144 is engageable with the housing 142 and magnet 60a to rotate the housing 142 and magnet 60a relative to the cassette 10a to move the particles 146 from the mixing chamber 14a to the washing chamber 38a. It will be appreciated that valves 34a and 36a operate in a similar manner to transfer the particles 146 from the washing chamber 38a to the washing chamber 40a and from the washing chamber 40a to the elution chamber 42a, respectively.

In one embodiment, a total of about 200 μL sample is placed into the cassette. The sample is mixed with a total of about 50 μL of the PK solution by pumping the mixture of the sample and PK solution for about one minute. A total of about 200 μL of the lysis solution is added to the sample and PK solution, and the solutions are pumped for about one minute to mix the solutions. The mixture is then heated at about 60° C. for about ten minutes, and the mixture is allowed to cool for about 5 minutes. The mixture is further pumped while it cools. A total of about 500 μL of binding solution is added to the mixture. The solutions are pumped for about one minute. The magnetic beads are added to the solution and pumped for about two minutes. The magnetic beads are transferred and washed as described above. A total of about 700 μL of washing solution is provided in each of the washing chambers. A total of about 200 μL of elution solution is provided in the elution chamber. The magnetic beads are mixed with the elution solution by pumping the mixture for about one minute. The mixture is then heated at about 90° C. for about two minutes. The process continues as previously described.

Although the cassette 10 has been described as having a mixing chamber 14, two washing chambers 38 and 40 and an elution chamber 42, it is envisioned that only one washing chamber or no washing chamber may alternatively be provided.

Although the cassette has been described as using a single removable magnet 60, it is envisioned that each valve may include a positionable magnet, such that the magnet does not need to be removed. The magnet 60 may be rotatable, and used to rotate the second piece of the valves. Alternatively, the magnet may only slide inside of each of the valves, and the second piece is rotated independent of the magnet.

It is envisioned that a cassette 10 that does not use valves as described herein may be used to transfer the magnetic particles from the mixing chamber to the elution chamber. In such an embodiment, a slideable magnet may be provided to transfer the magnetic particles from one chamber to the next.

Although the cassette 10 has been described as using a PK solution, lysis solution, binding solution and magnetic beads to release the nucleic acid and magnetic beads, it is envisioned that it may be possible to practice the invention without using each of the above solutions. In addition, although the solution was described as using a PK solution to break up the cells, it is envisioned that any enzyme which causes cells to break up to release nucleic acid may be used with the invention.

It is envisioned that the housing 12 may be transparent, such that the procedure can be viewed.

In one embodiment the thin film 74 is a lamination.

In one embodiment, the lids 52 and 54 may be screw-top lids. In one embodiment, the lids 52, 54 include a hydrophobic membrane, which allows gasses to vent through the lid, but does not allow the liquids to escape the cassette 100.

In one embodiment, pump 50 is insertable into opening 100. In one embodiment, pump 50 can also be used as a pipette to remove the sample from the cassette 10.

It is also envisioned that the mixing chamber 14 may be provided without a puncturable thin film 74. In such an embodiment, the plungers 24, 26, 28 and 30 would not need a piercing element 82. Instead, the plungers 24, 26, 28 and 30 would have a sealing element to prevent leakage of the contents of the holding chamber 16, 18, 20 and 22, associated with each plunger 24, 26, 28 and 30, respectively, until the plunger was moved.

Figure 25:
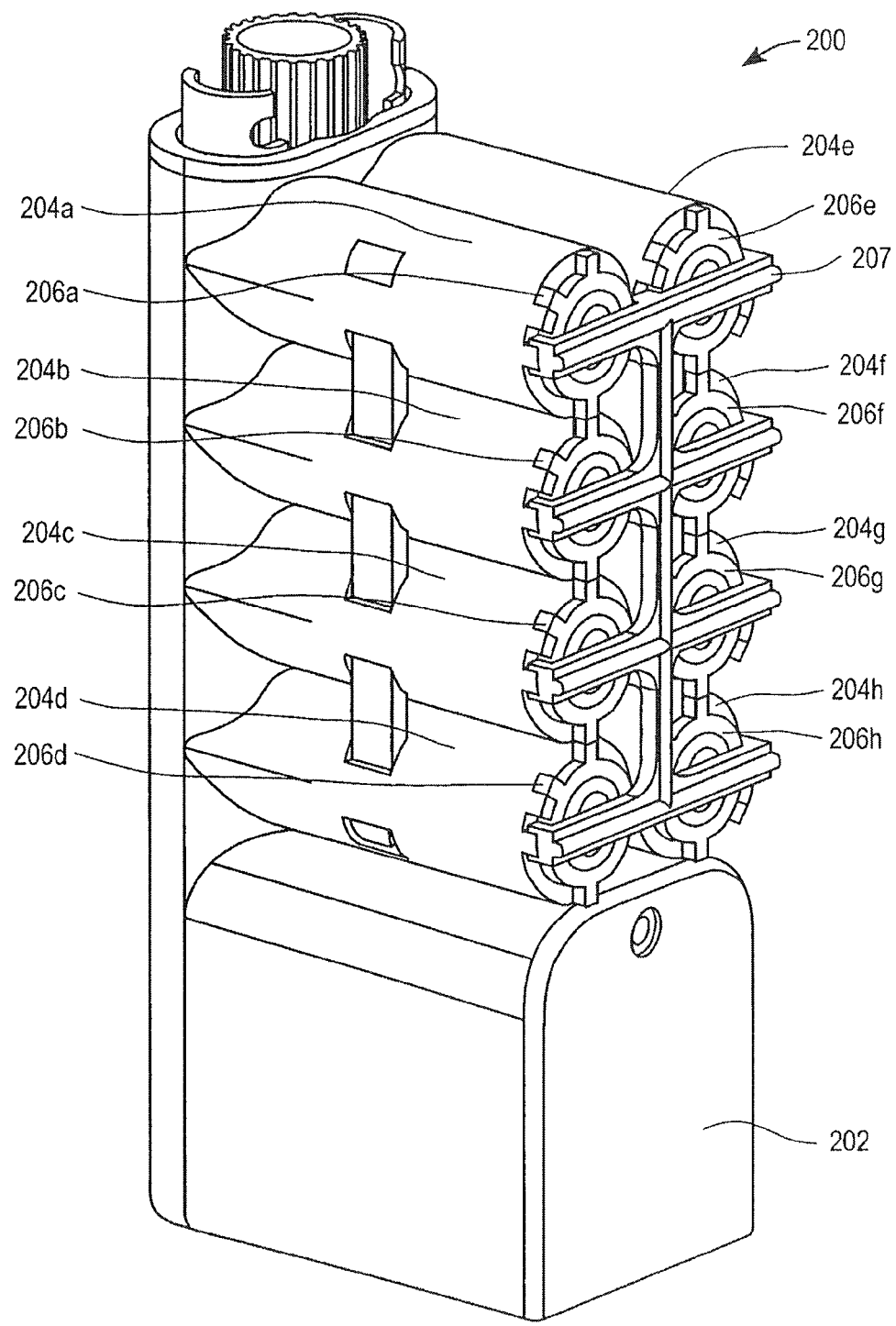
FIG. 25 is a perspective view of a cassette for preparing samples according to one embodiment of the invention.

FIG. 25 illustrates a cassette 200, which can be used to prepare cell samples. The cassette 200 includes a housing 202, first, second, third, fourth, fifth, sixth, seventh and eighth holding chambers 204a-h, respectively. Each of the holding chambers 204a-h includes a valve assembly 206a-h therein. A locking element 207 may also be provided.

Figure 26:
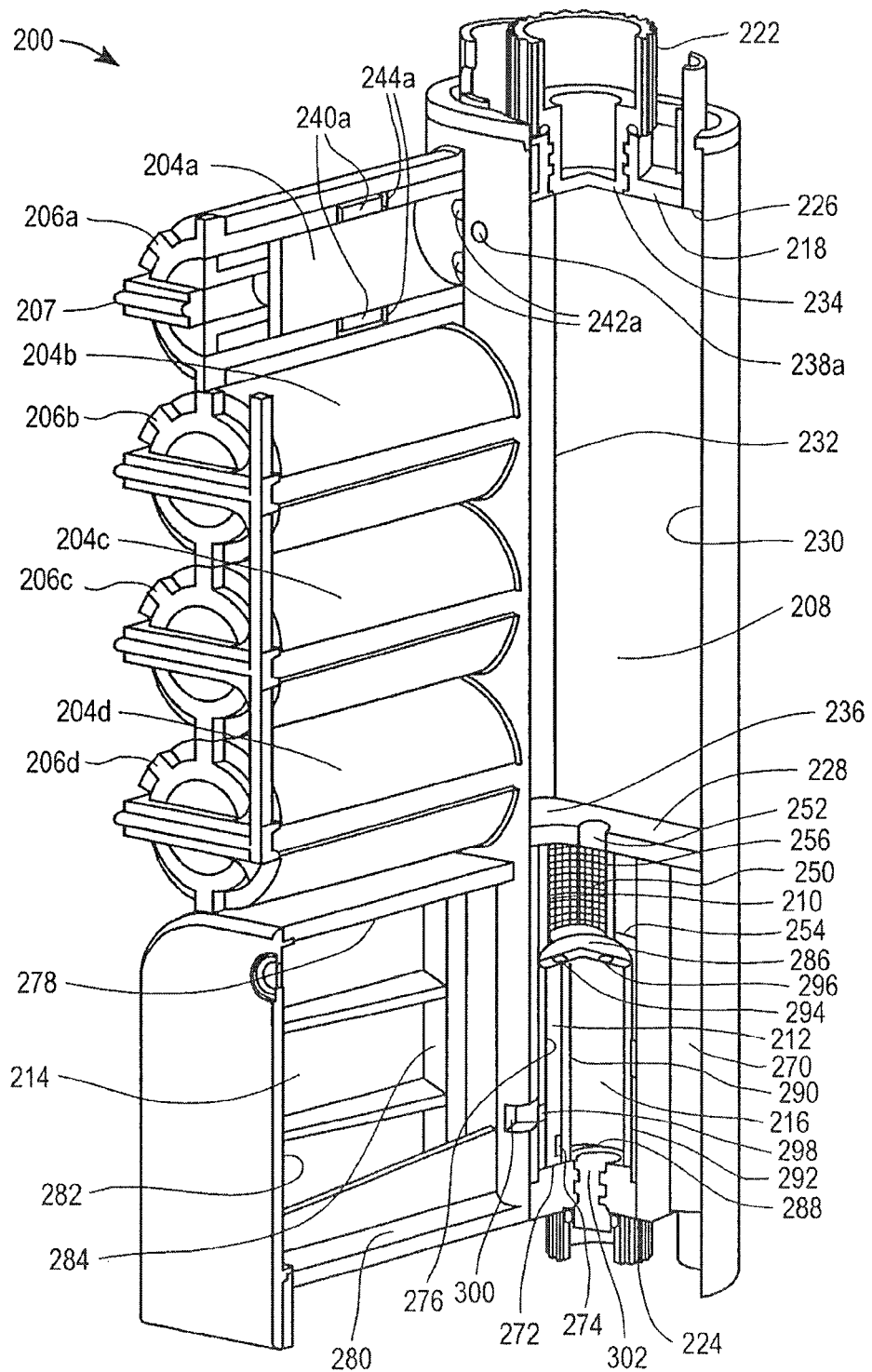
FIG. 26 is a partial cross-sectional view of the cassette of FIG. 25.

FIG. 26 illustrates the cassette 200 in more detail. The cassette 200 further includes a reaction chamber 208, a particle chamber 210, a waste chamber 212, a waste overflow chamber 214, an elution chamber 216, a plunger 218, and first and second lids 220 and 222, respectively. The cassette 200 may also include one or more heating elements (not shown).

Each of the holding chambers 204a-h, valve assemblies 206a-h, reaction chamber 208, particle chamber 210, waster chamber 212, waster overflow chamber 214, and plunger 218 are enclosed within the housing 202. The lids 222, 224 are movably or removably attached to the housing 202.

The reaction chamber 208 has a top surface 226, a bottom surface 228 and opposing side surfaces 230, 232.

The top surface 226 of the reaction chamber 208 includes an opening 234 therein. The first lid 222 is configured to provide access to the opening 234 in the top surface 226 of the reaction chamber 208. The illustrated lid 222 is a screw-top lid; however, any other lid which (removably) provides access to the opening 234.

The bottom surface 228 of the reaction chamber 208 includes an opening 236 therein. The opening 236 allows the reaction chamber 208 to be in fluid communication with the particle chamber 210.

The side surface 232 includes openings 238a-h therein. The openings 238ah allow the reaction chamber 208 to be in fluid communication with the holding chambers 204a-h, respectively.

The cassette 200 includes a binding solution in a holding chamber 204a. The cassette 200 further includes a lysis solution in a holding chamber 204b. The cassette 200 further includes a proteinase K (PK) solution in a holding chamber 204c. The cassette 200 further includes a washing solution in one or more of the holding chambers 204d-e. The cassette 200 further includes an elution solution in a holding chamber 204f.

The plunger 218 and the first lid 222 are shown attached to one another to form an integral plunging system. The plunger 218 is compressible to pump the contents of the reaction chamber 208. Alternatively, a separate pump may also be provided to pump the contents of the reaction chamber 208. The plunger 218 is also moveable within the reaction chamber 208 to push the contents of the reaction chamber 208 through the particle chamber 210.

The holding chambers 204a-h are formed in the housing 202 of the cassette 200. Each of the holding chambers 204a-h include a guide 240a-h engageable with a corresponding slot in the valve assembly 206. The holding chambers 204a-h also include at least one opening 242a-h, engageable with corresponding openings in the valve assembly 206a-h. The housing 202 also includes slots 244a-h, engageable with corresponding guides in the valve assembly 206a-h.

The particle chamber 210 includes a body 250, having a first opening 252, a second opening 254, and a plurality of particles 256 thereon. The particles may be magnetic or nonmagnetic, depending on the application of the cassette 200. The particles may be, for example, cellulose, plastic or iron. The particle chamber 210 is shown aligned with the reaction chamber 208.

The waste chamber 212 and the elution chamber 216 are integrated with one another and are rotatable relative to the housing 202. The waste overflow chamber 214 is positioned near the waste chamber 212 and is capable of being in fluid communication with the waste chamber 212. The waste chamber 212 and elution chamber 216 are alignable with the particle chamber and are capable of being in fluid communication with the particle chamber 210.

The waste chamber 212 has a top surface 270, a bottom surface 272, an inner surface 274 and an outer surface 276. The overflow waste chamber 214 has a top surface 278, a bottom surface 280 and opposing side surfaces 282, 284. The elution chamber 216 also has a top surface 286, a bottom surface 288, an inner surface 290 and an outer surface 292.

It will be appreciated that the outer surface 276 of the waste chamber 212 and the outer surface 292 of the elution chamber 216 are integrated with one another. It will also be appreciated that the inner surface 274 of the waste chamber 212 is the same as the inner surface 290 of the elution chamber 216.

The top surface 270 of the waste chamber 212 and the top surface 286 of the elution chamber 216 each have an opening 294, 296, respectively. These openings 294,296 are alignable with the opening 252 in the particle chamber 210 to provide a fluid communication route between the particle chamber 210 and the waste chamber 212 and the elution chamber 216.

The outer surface 276 of the waste chamber 212 includes an opening 298 therein. One of the side surfaces 282,284 of the overflow waste chamber 214 includes an opening 300 therein. The opening 298 and opening 300 are alignable, such that fluid flowing into the waste chamber 212 can flow from the waste chamber 212 and into the overflow waste chamber 214.

The bottom surface 288 of the elution chamber 216 includes an opening 302 therein. The second lid 224 is configured to provide access to the opening 302 in the bottom surface 288 of the elution chamber 216. The illustrated lid 224 is a screw-top lid; however, any other lid which (removably) provides access to the opening 302.

Figure 27:
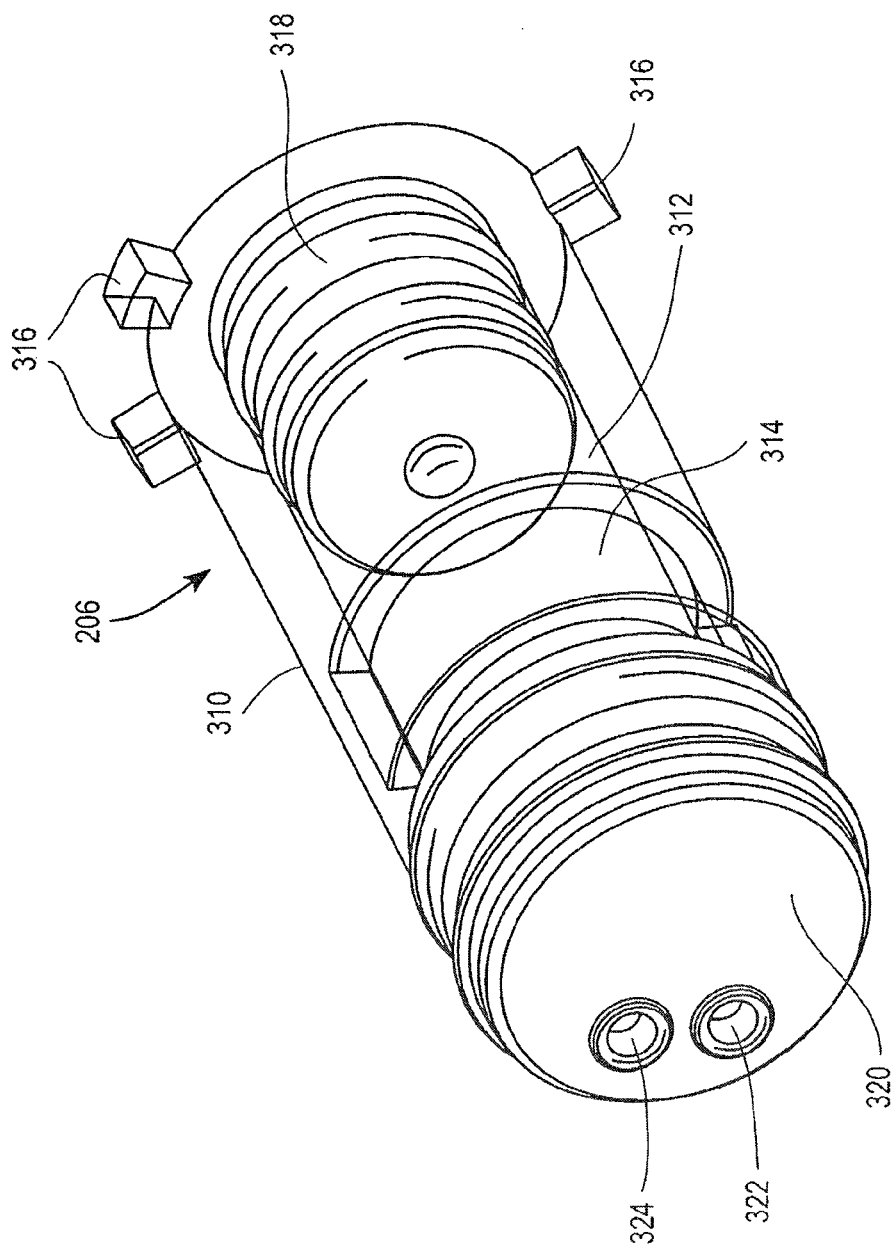
FIG. 27 is a partial cross-sectional perspective view of a valve for use in the cassette of FIG. 25.
Figure 28:
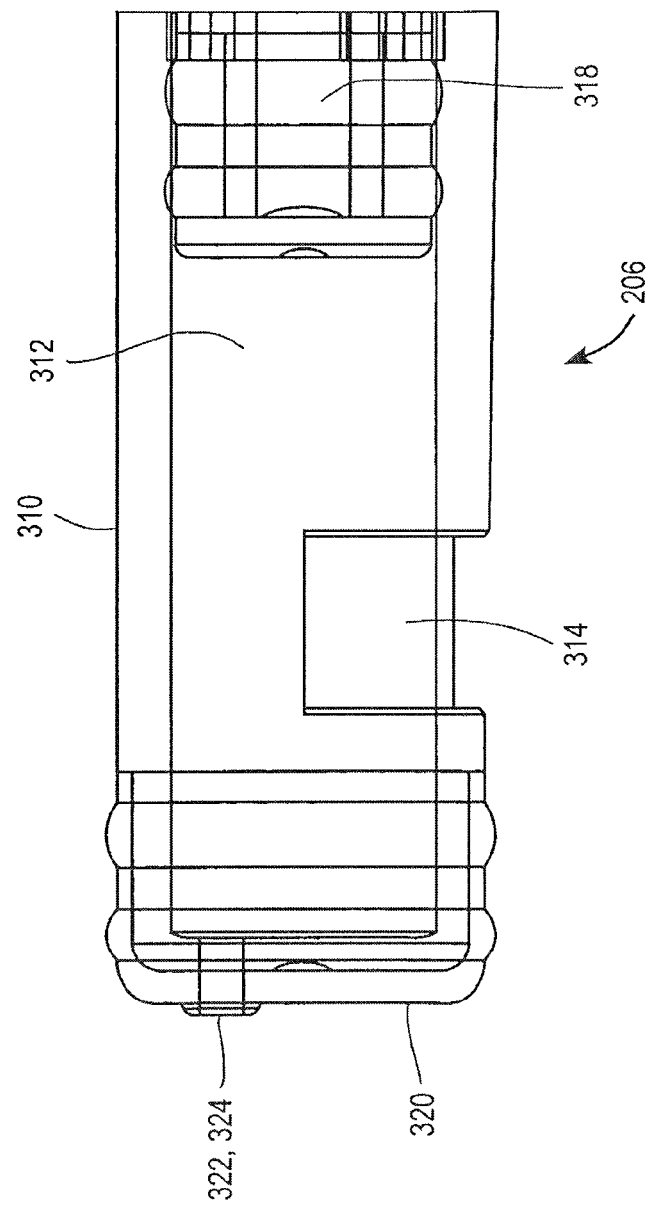
FIG. 28 is a partial cross-sectional side view of the valve of FIG. 25.

FIGS. 27 and 28 illustrate the valve assembly 206 in more detail. Valve assembly 206 includes a housing 310. The housing 310 includes a chamber 312 therein, a slot 314, and projections 316 extending therefrom. The chamber 312 includes a pump 318 therein. A lid 320 is provided at an end of the housing to seal the chamber 310. The lid includes first and second openings 322, 324, extending therethrough and providing fluid communication with the chamber 312.

When the openings 322, 324 are not aligned with openings 238*a-h*, the contents of the chamber 312 are sealed within the valve assembly; however, when the openings 322, 324 are aligned with openings 238*a-h*, the contents of the chamber 312 are releasable from the chamber 312. The slot 314 is used to guide the openings 322,324 to the location where the openings 322, 324 are aligned with the openings 238*a-h*. The pump 318 is used to transfer the contents from the chamber 312 and into the reaction chamber 214 through the openings 322, 324.

The cassette 200 is assembled by inserting the valve assemblies 206*a-h* into the holding chambers 204*a-h* of the housing. The locking element 207 may be connected to the housing to secure valve assemblies 206*a-h* in the holding chambers 204*a-h*. The waste chamber and elution chamber 216 assembly is inserted into the housing 202 and the lid 224 is secured to the housing 202. The plunger 218 is also inserted into the reaction chamber 208 and the lid 222 is secured to the housing.

Figure 29:
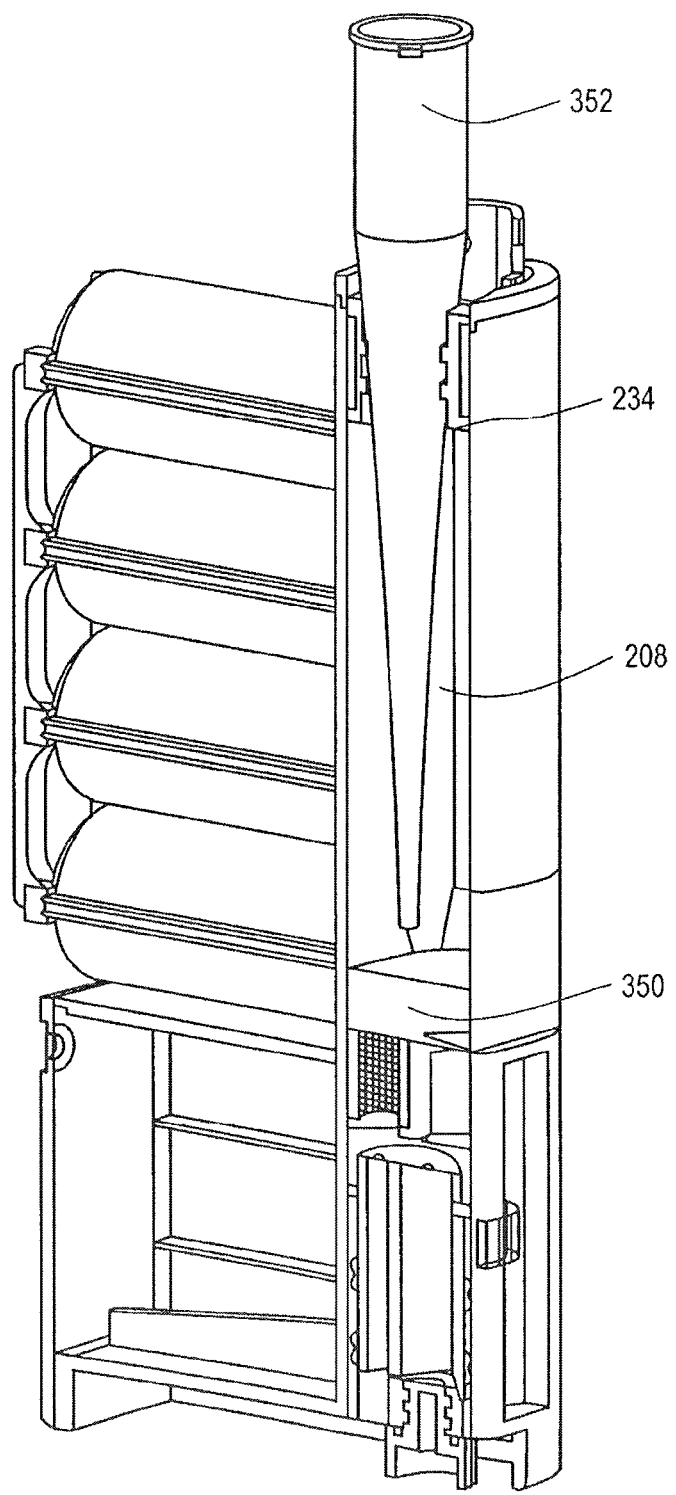
FIG. 29 is a cross-sectional perspective view of the cassette of FIG. 25, showing the addition of a sample into a mixing chamber, according to an embodiment of the invention.

In use, as shown in FIG. 29, the first lid 222 is removed to provide access to the opening 234 of the reaction chamber 208. A sample of cells 350 is placed into the cassette 200 using a pipette 352. The cells in the sample include nucleic acid. The pipette 352 having the sample therein is placed in the reaction chamber 208. The sample is released from the pipette 352.

Figure 30:
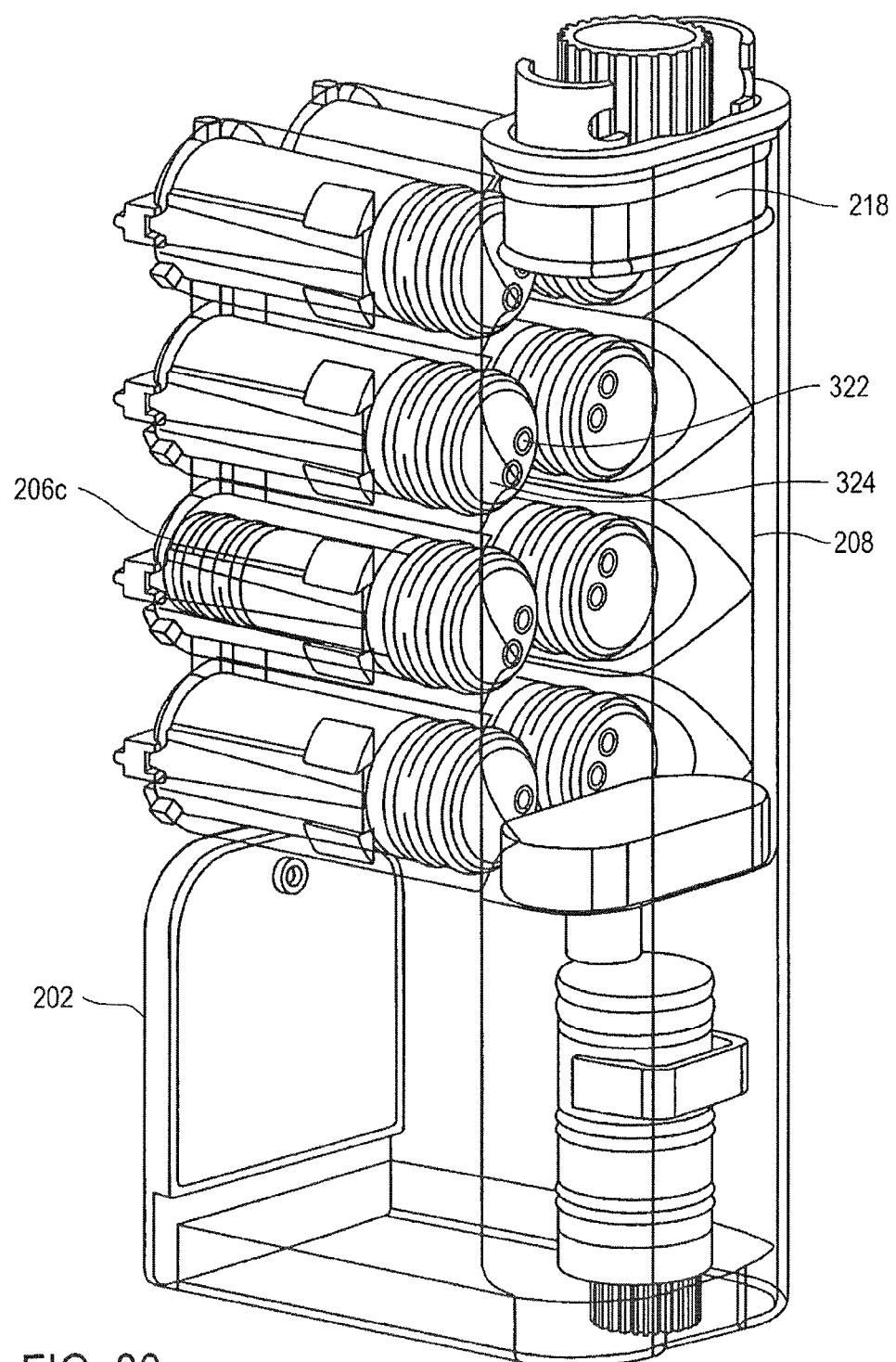
FIG. 30 is a cross-sectional perspective view of the cassette of FIG. 25, showing the transfer of a PK solution into a mixing chamber, according to an embodiment of the invention.

As shown in FIG. 30, the PK solution is added to the sample. The PK solution is added by rotating the valve assembly 206*c* relative to the housing 202. At least one of the openings 322, 324 of the valve assembly 206*c* is aligned with the opening 242*c* in the holding chamber 204*c* to release the PK solution from the holding chamber 204*c* and into the reaction chamber 208 through the opening 238*c* in the housing 202.

The PK Solution is mixed with the sample by pumping the mixture with the plunger 218. As described hereinabove, the PK solution destroys the wall so the cells of the sample, creating bulk material and nucleic acid in the bulk material.

Figure 31:
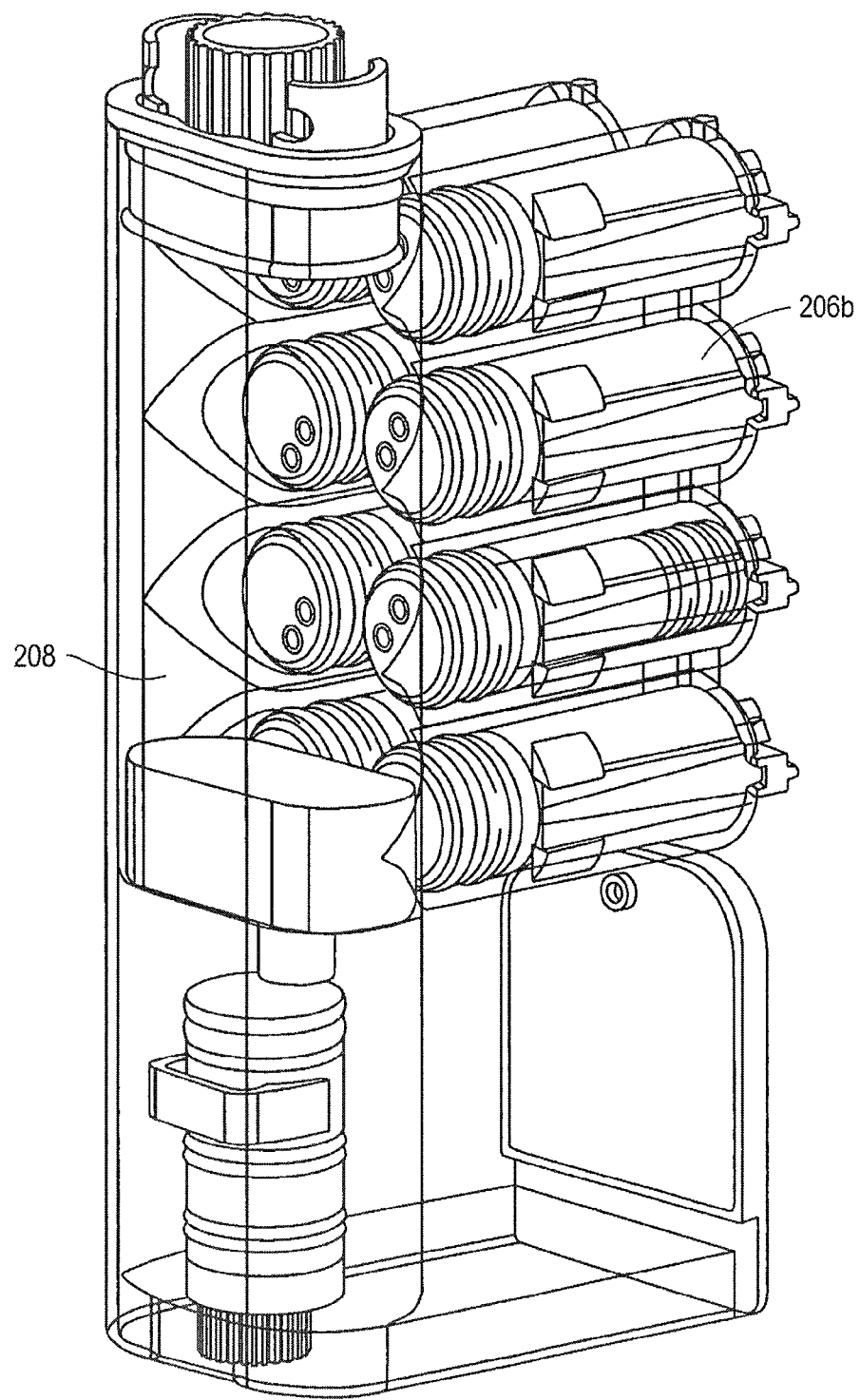
FIG. 31 is a cross-sectional perspective view of the cassette of FIG. 25, showing the transfer of a lysis solution into a mixing chamber, according to an embodiment of the invention.

As shown in FIG. 31, the lysis solution is added to the sample. The valve assembly 206*b* operates in the same manner as valve assembly 206*c* to transfer the lysis solution in the holding chamber 204*b* into the reaction chamber 208. The sample is typically pumped to mix the lysis solution with the mixed PK solution and sample. The lysis solution is typically a salt or detergent, and is used to solulibize the bulk material, as discussed hereinabove.

Figure 32:
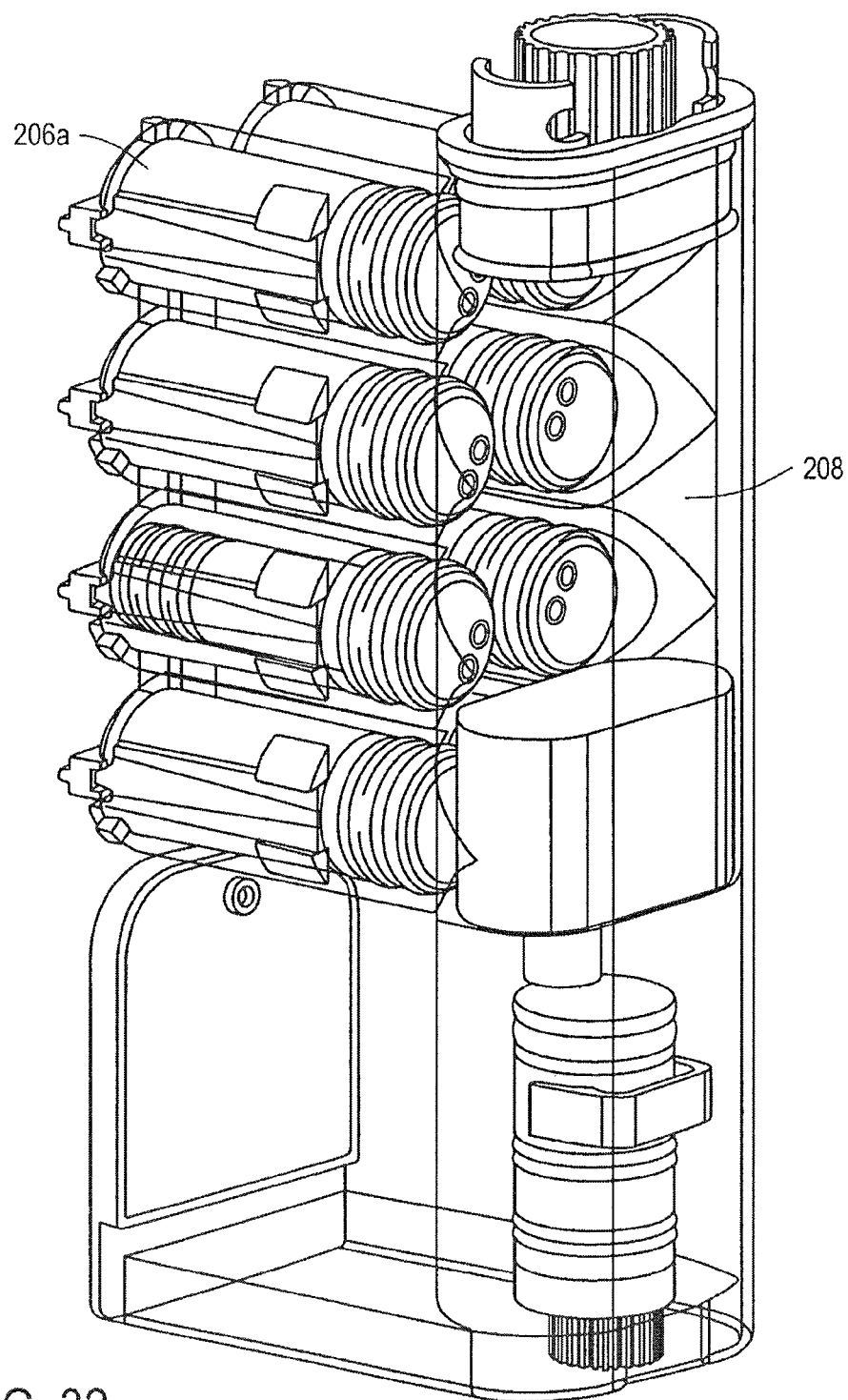
FIG. 32 is a cross-sectional perspective view of the cassette of FIG. 25, showing the transfer of a binding solution into a mixing chamber, according to an embodiment of the invention.

As shown in FIG. 32, a binding solution is added to the sample, PK solution and lysis solution. Valve assembly 206*a* operates in the same manner as valve assembly 206*c* to transfer the binding solution in the holding chamber 204*a* into the reaction chamber 208. The solution is pumped to mix the binding solution with the PK solution, lysis solution and sample. The binding solution is typically hydrophobic and increases sale in the solution.

Figure 33:
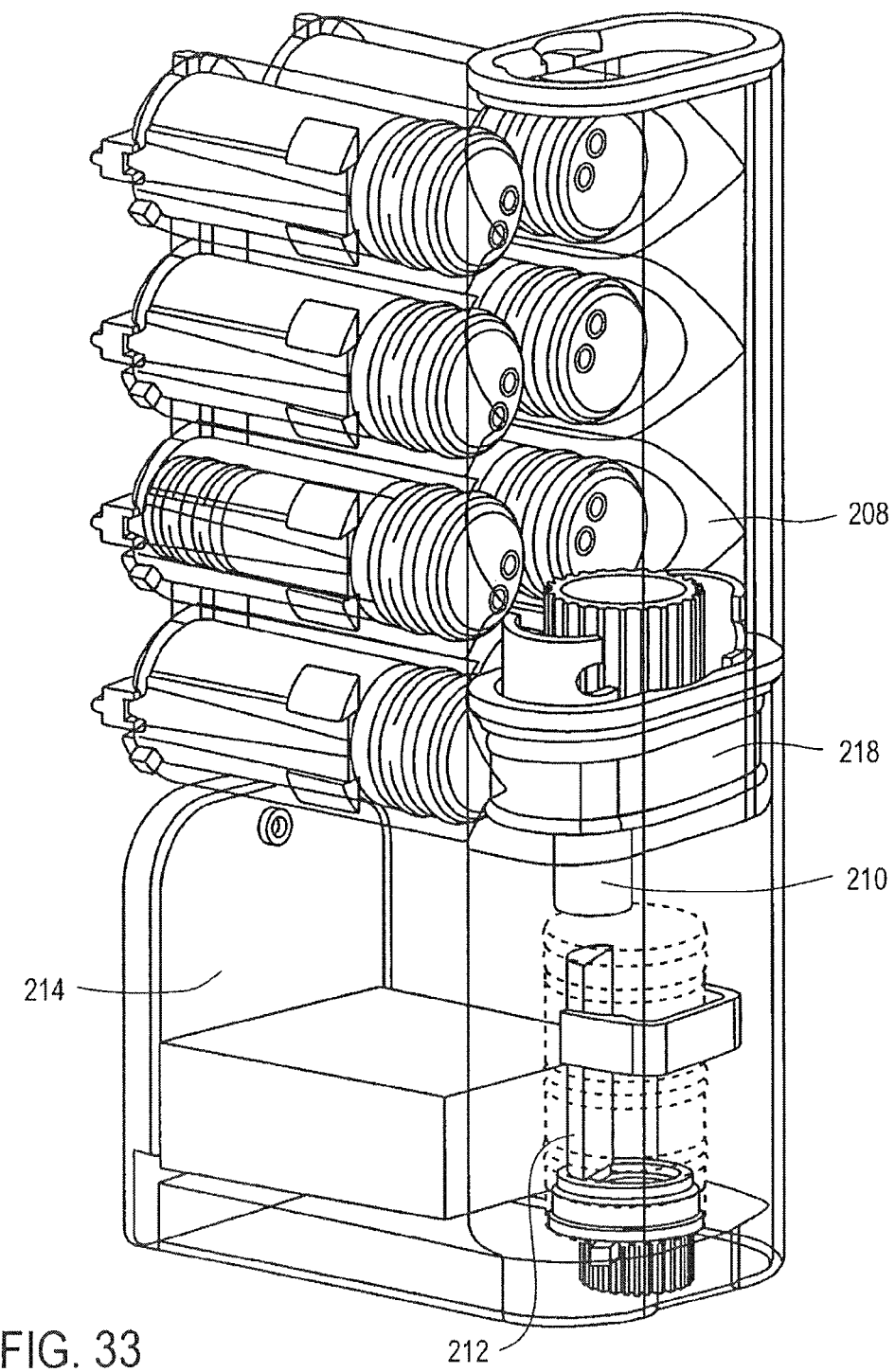
FIG. 33 is a cross-sectional perspective view of the cassette of FIG. 25, showing transfer of a sample through particles and into a waste chamber, according to an embodiment of the invention.

As shown in FIG. 33, the solution is pumped through the particles in the particle chamber 210. The nucleic acid binds to the particles in the particle chamber, while the remaining solution flows into the waste chamber 212, and, if needed, the waste overflow chamber 214. As described above, when the opening 298 in the waste chamber 212 is aligned with the opening 300 in the waste overflow chamber 214, the solution can flow into the waste overflow chamber 214 from the waste chamber 212.

Figure 34:
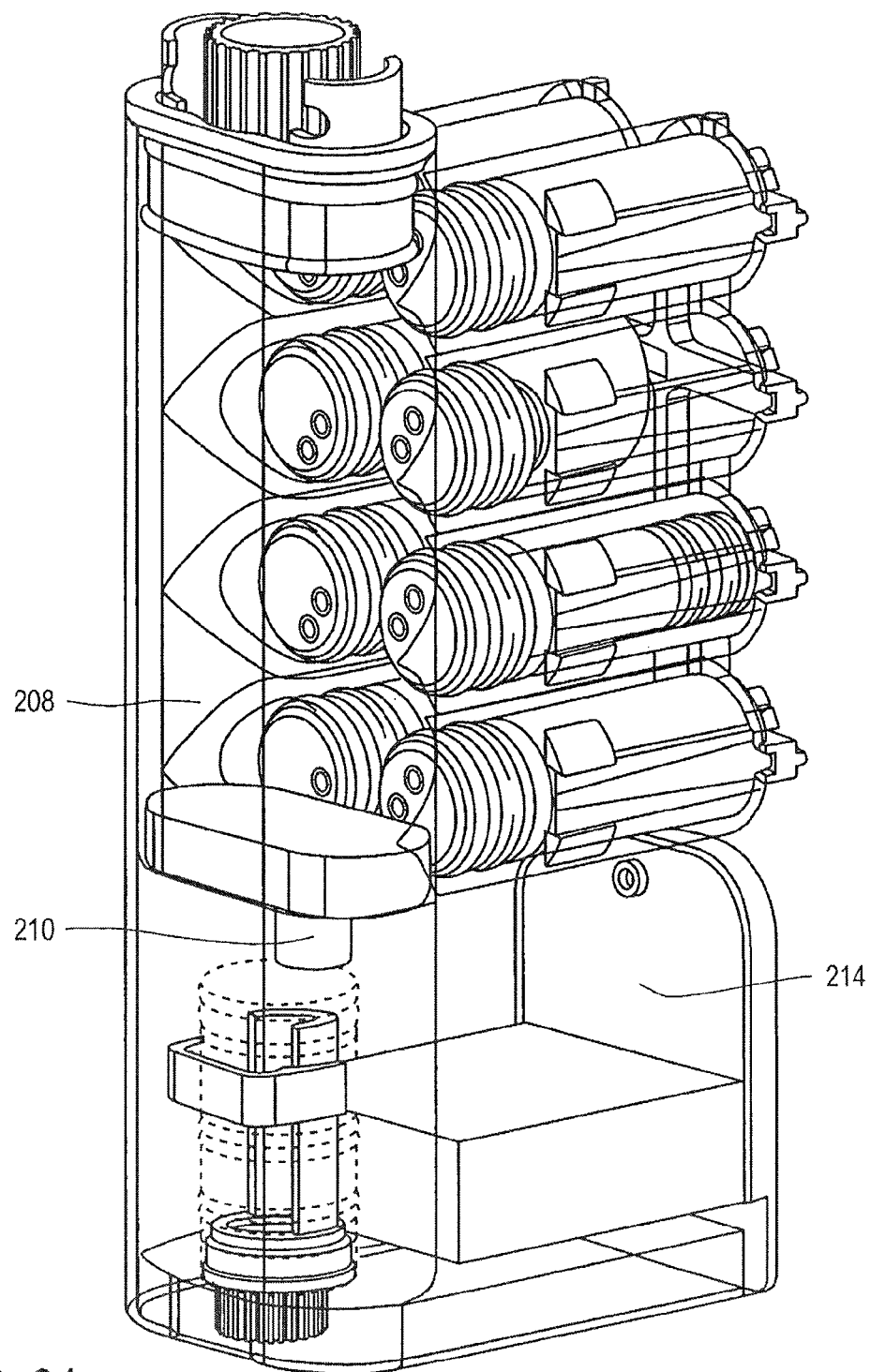
FIG. 34 is a cross-sectional perspective view of the cassette of FIG. 25, showing the pumping of a wash buffer into the mixing chamber, according to an embodiment of the invention.

As shown in FIG. 34, the washing solution is added to the reaction chamber 208 by operating the valve assembly 206*d* in the same manner as valve assembly 206*c* to transfer the washing solution from the holding chamber 204*d* into the reaction chamber 208.

Figure 35:
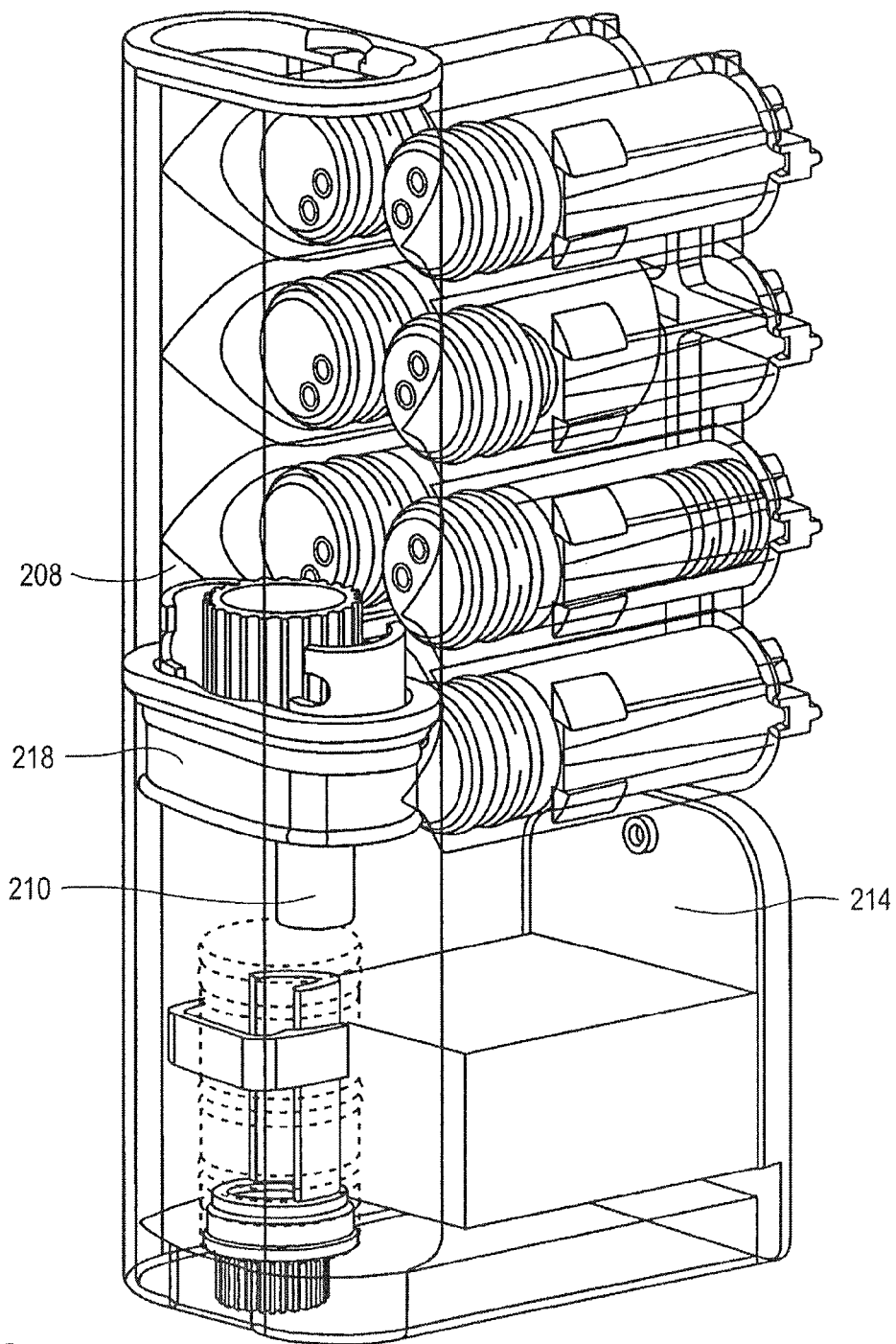
FIG. 35 is a cross-sectional perspective view of the cassette of FIG. 25, showing the pumping of the wash buffer through the particles, according to an embodiment of the invention.

As shown in FIG. 35, the first washing solution is pumped through the particle chamber 210 and into the waste chamber 212, and, if needed, the waste overflow chamber 214.

Figure 36:
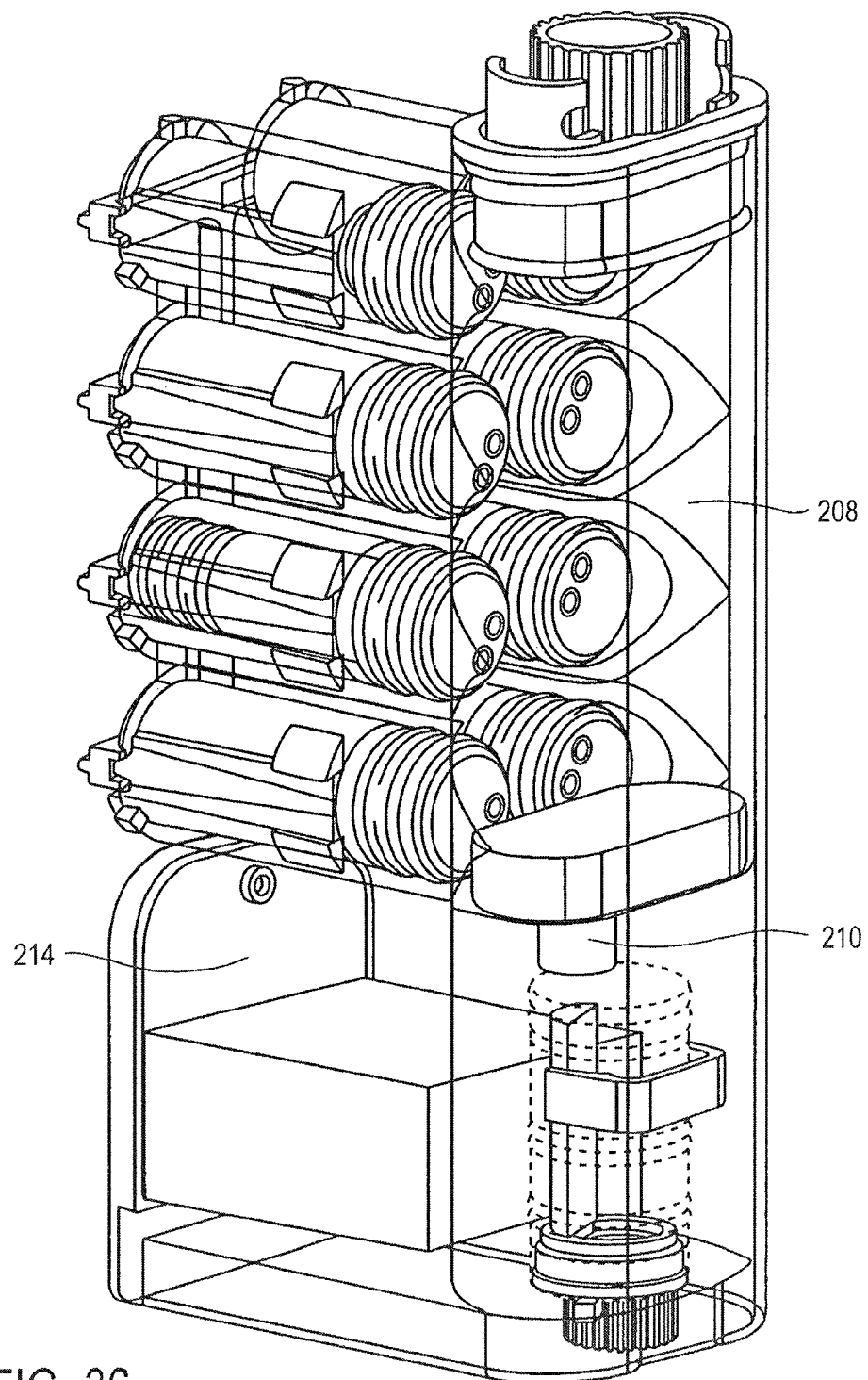
FIG. 36 is a cross-sectional perspective view of the cassette of FIG. 25, showing the pumping of a second wash buffer into the mixing chamber, according to an embodiment of the invention.

As shown in FIG. 36, a second washing solution is added to the reaction chamber 208 by operating the valve assembly 206*e* in the same manner as valve assembly 206*c* to transfer the washing solution from the holding chamber 204*e* into the reaction chamber 208.

Figure 37:
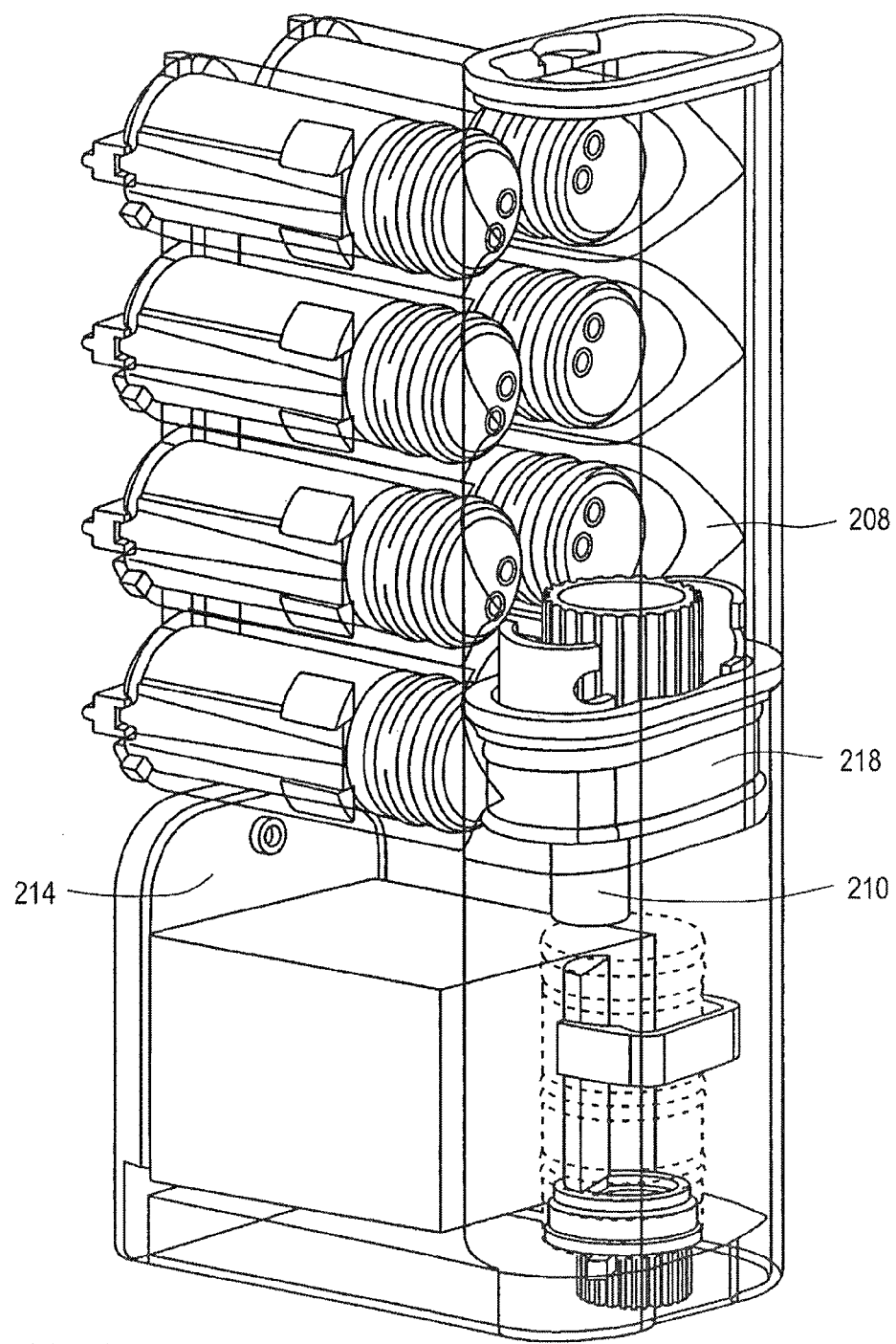
FIG. 37 is a cross-sectional perspective view of the cassette of FIG. 25, showing the pumping of the second wash buffer through the particles, according to an embodiment of the invention.

As shown in FIG. 37, the second washing solution is pumped through the particle chamber 210 and into the waste chamber 212, and, if needed, the waste overflow chamber 214.

Figure 38:
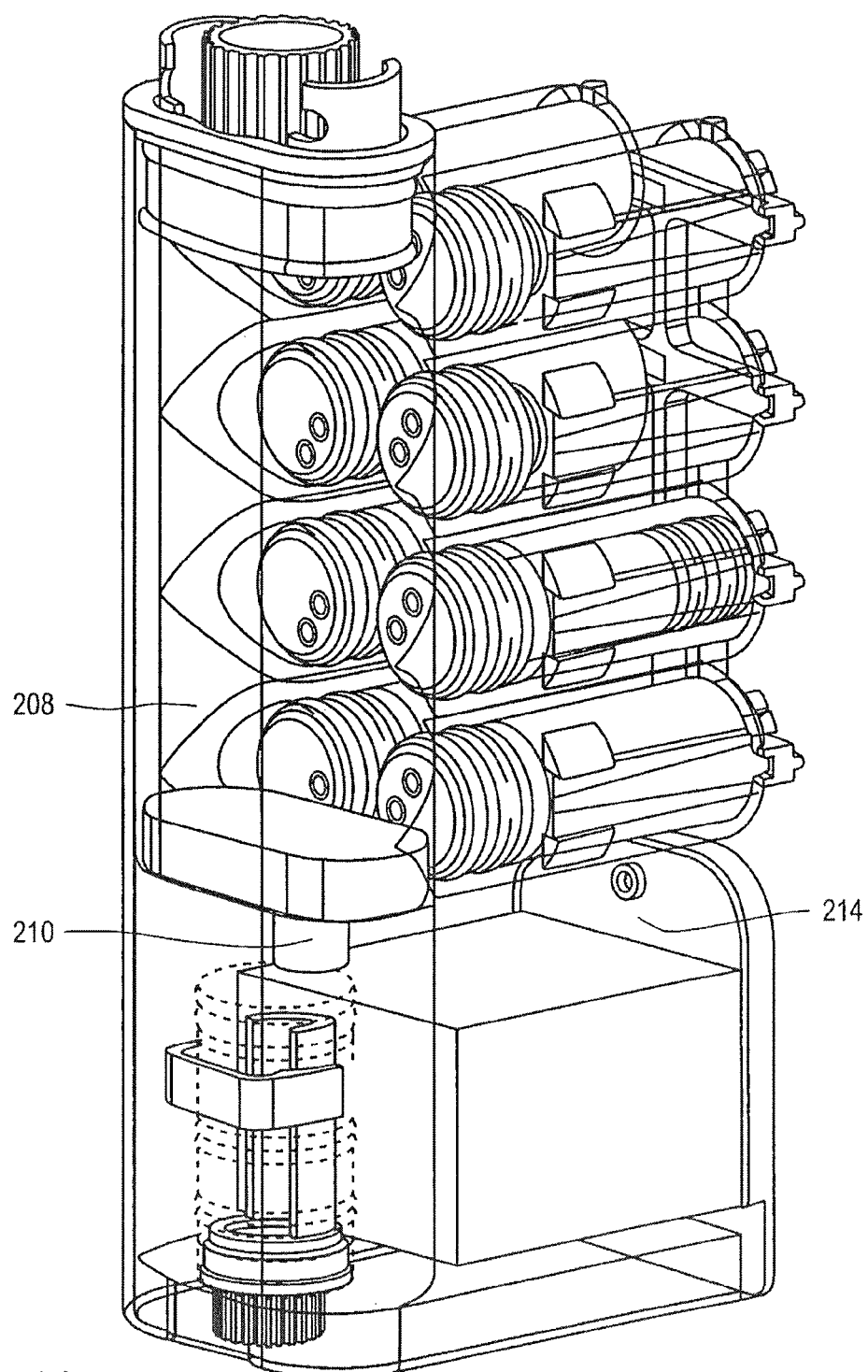
FIG. 38 is a cross-sectional perspective view of the cassette of FIG. 25, showing the pumping of an elution buffer into the mixing chamber, according to an embodiment of the invention.

As shown in FIG. 38, an elution solution is added to the reaction chamber 208 by operating the valve assembly 206*f* in the same manner as valve assembly 206*c* to transfer the elution solution from the holding chamber 204*f* into the reaction chamber 208.

The waste chamber and elution chamber assembly is rotated to align the opening 296 of the elution chamber 216 with the opening 252 of the particle chamber 210 such that the elution solution is transferable into the elution chamber 216. It will be appreciated that the opening 296 can be aligned with the opening 252 before or after the elution solution is added to the reaction chamber 208.

Figure 39:
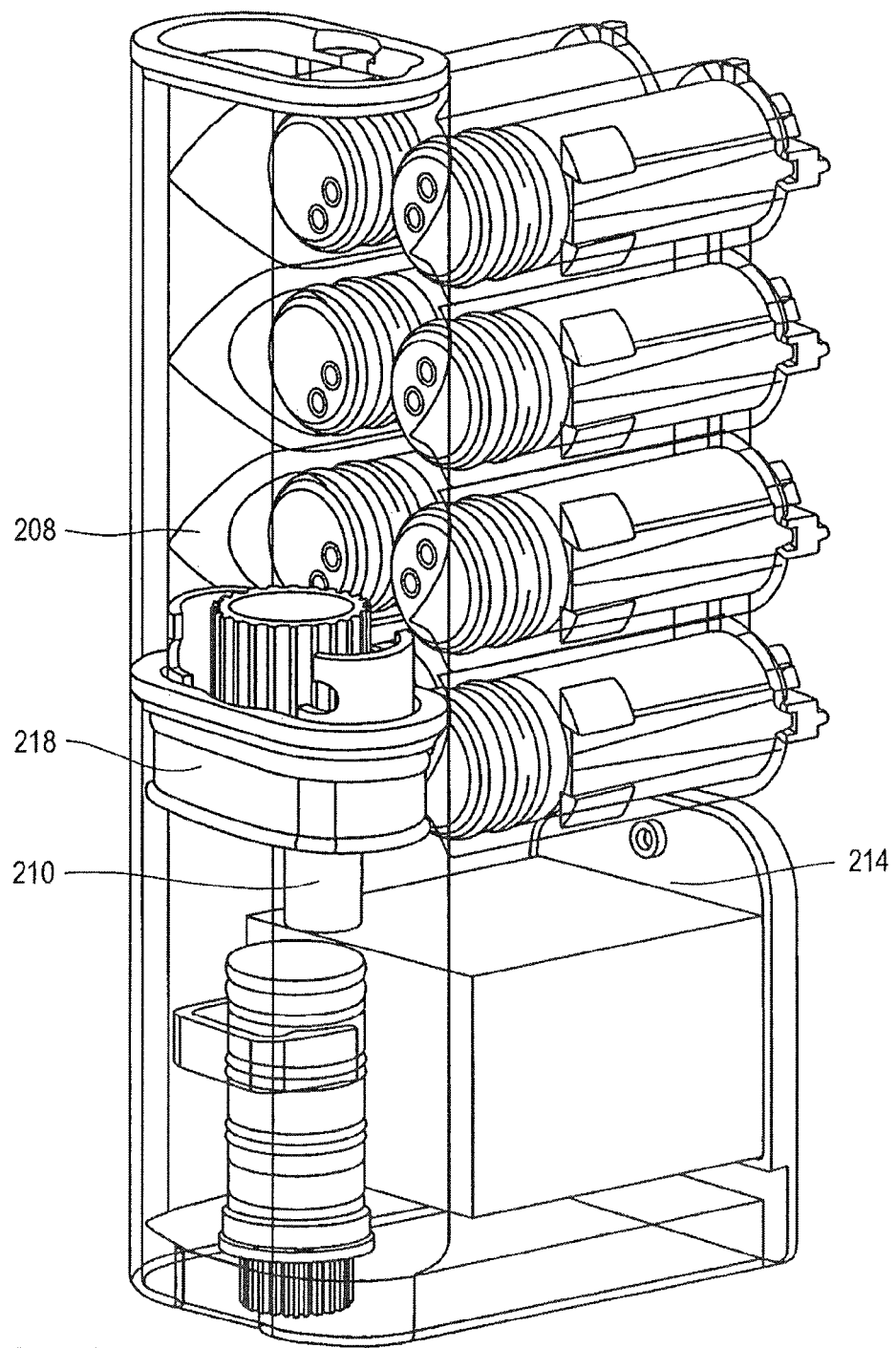
FIG. 39 is a cross-sectional perspective view of the cassette of FIG. 25, showing the pumping of the elution buffer through the particles and into the elution chamber, according to an embodiment of the invention.

As shown in FIG. 39, the elution solution is pumped through the particle chamber 210 to elute the bound nucleic acid. The nucleic acid and elution solution flow into the elution chamber 216.

Figure 40:
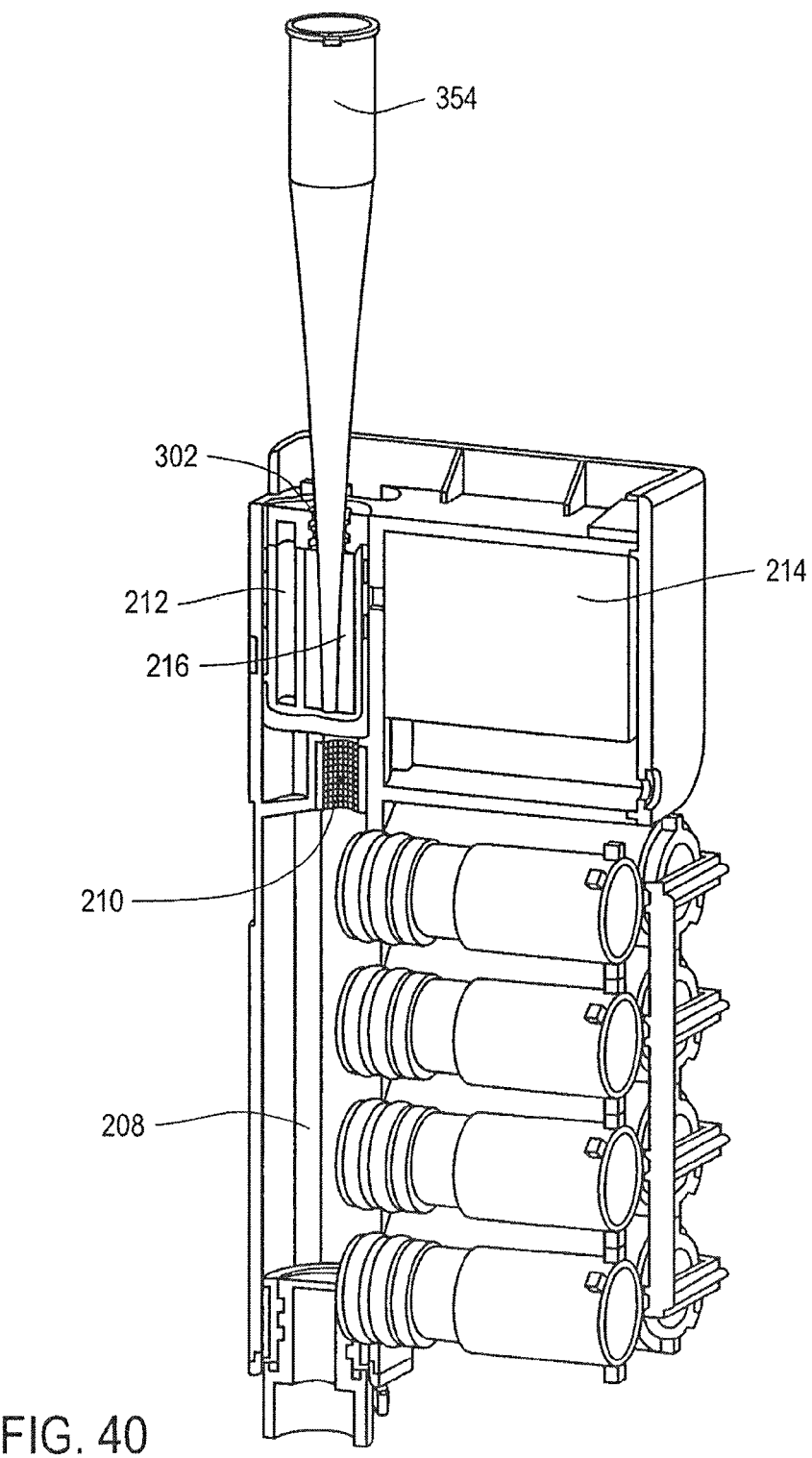
FIG. 40 is a cross-sectional perspective view of the cassette of FIG. 25, showing the removal of the sample from the elution chamber, according to an embodiment of the invention.

As shown in FIG. 40, the prepared sample of nucleic acid may be accessed using a pipette 354. The second lid 224 is removed to provide access to the opening 302 in the elution chamber 216. The pipette 354 is inserted into the opening 302 and the prepared sample of nucleic acid is withdrawn.

It will be appreciated that the cassette 200 can be placed with similar cassettes into a magazine or rack for containing a series of cassettes. The magazine or rack can be placed into an instrument, and a protocol may be selected for preparing the sample in the cassette 200 in the instrument.

Cassette 200 may include one or more heating elements as described hereinabove with respect to cassette 100.

The cassettes 100, 200 may be disposable.

It will be appreciated that although the cassettes 100, 200 have been described with respect to breaking cells to extract nucleic acid, the cassettes 100, 200 can be used to break cells to extract other cell components, such as, for example, protein. Also, although a lysis solution has been described as being used to break up cells, it will be appreciated that any substance that can break up cells, such as, for example, reagents, enzymes, catatropic salts, other lysis solutions and the like.

The cassettes described herein are advantageous because it is closed. There is no contamination of the sample during the process. In addition, a fewer number of samples, including as few as one sample, may be prepared.

The foregoing description with attached drawings is only illustrative of possible embodiments of the described method and should only be construed as such. Other persons of ordinary skill in the art will realize that many other specific embodiments are possible that fall within the scope and spirit of the present idea. The scope of the invention is indicated by the following claims rather than by the foregoing description. Any and all modifications which come within the meaning and range of equivalency of the following claims are to be considered within their scope.

What is claimed is:

1. A system comprising:
   a plurality of cassettes, each cassette of the plurality of cassettes comprising:
   a first chamber comprising an opening configured for receiving a sample into the first chamber, and a removable lid configured to provide access to the opening;
   a second chamber;
   a third chamber;
   a first valve comprising a valve housing defining a first valve opening in fluid communication with the first chamber and a second valve opening in fluid communication with the second chamber;
   a second valve comprising a valve housing defining a first valve opening in fluid communication with the second chamber and a second valve opening in fluid communication with the third chamber; and
   a plurality of reagent chambers, wherein each of the plurality of reagent chambers comprises a puncturable or sealable member defining at least a portion of a boundary between the plurality of reagent chambers and the first chamber; and
   a magazine configured to receive the plurality of cassettes.

2. The system of claim 1, wherein each of the plurality of reagent chambers comprises a puncturable member, and each cassette of the plurality of cassettes further comprises a plunger at least partially disposed in each of the plurality of reagent chambers and configured to puncture the puncturable member when the plunger is moved.

3. The system of claim 1, wherein each cassette of the plurality of cassettes further comprises a plunger at least partially disposed in each of the plurality of reagent chambers, the plungers comprising a sealable member configured to prevent leakage between the reagent chambers and the first chamber until the plungers are moved.

4. The system of claim 1, wherein each cassette of the plurality of cassettes further comprises a pump comprising an actuator and a nozzle, wherein the actuator is disposed outside of the second chamber and the nozzle is disposed at least partially inside the second chamber.

5. The system of claim 4, wherein the pump is a first pump, and each cassette of the plurality of cassettes further comprises a second pump comprising an actuator and a nozzle, wherein the actuator is disposed outside of the third chamber and the nozzle is disposed at least partially inside the third chamber.

6. The system of claim 1, further comprising a fourth chamber and a third valve comprising a valve housing defining a first valve opening in fluid communication with the third chamber and a second valve opening in fluid communication with the fourth chamber.

7. The system of claim 1, further comprising a positionable magnet configured to be inserted into each of the first and second valves.

8. A system for preparing a plurality of samples of cells, the system comprising:
   a plurality of cassettes, each cassette of the plurality of cassettes comprising:
   a mixing chamber comprising an opening configured for receiving a sample of cells into the mixing chamber, and a removable lid configured to provide access to the opening;
   a first washing chamber;
   a first valve comprising a valve housing defining a first, valve opening in fluid communication with the mixing chamber and a second valve opening in fluid communication with the first washing chamber;
   a second valve comprising a valve housing defining a first valve opening in fluid communication with the first washing chamber and a second valve opening in fluid communication with a second washing chamber or an elution chamber; and
   a plurality of reagent chambers, wherein each of the plurality of reagent chambers comprises a puncturable or sealable member defining at least a portion of a boundary between the plurality of reagent chambers and the mixing chamber, wherein the plurality of reagent chambers contain one or more of a lysis buffer, enzyme, magnetic particles, or chaotropic salt; and
   a magazine configured to receive the plurality of cassettes.

9. The system of claim 8, wherein each of the plurality of reagent chambers comprises a puncturable member, and each cassette of the plurality of cassettes further comprises a plunger at least partially disposed in each of the plurality of reagent chambers and configured to puncture the puncturable member when the plunger is moved.

10. The system of claim 8, wherein each cassette of the plurality of cassettes further comprises a plunger at least partially disposed in each of the plurality of reagent chambers, the plungers comprising a sealable member configured to prevent leakage between the reagent chambers and the second chamber until the plungers are moved.

11. The system of claim 8, wherein each cassette of the plurality of cassettes further comprises an actuator and a nozzle, wherein the actuator is disposed outside of the first washing chamber and the nozzle is disposed at least partially inside the first washing chamber.

12. The system of claim 11, wherein the pump is a first pump, and each cassette of the plurality of cassettes further comprises a second pump comprising an actuator and a nozzle, wherein the actuator is disposed outside of the second washing chamber or the elution chamber and, the nozzle is disposed at least partially inside the second washing chamber or the elution chamber.

13. The system of claim 8, wherein each cassette of the plurality of cassettes further comprises a pump coupled to the mixing chamber, the pump configured to mix a sample of cells and one or more reagents in the mixing chamber.

14. The system of claim 8, wherein the second valve opening of the second valve is in fluid communication with the second washing chamber, and each cassette of the plurality of cassettes further comprises a third valve comprising a valve housing defining a first valve opening in fluid communication with the second wash chamber and a second valve opening in fluid communication with the elution chamber.

15. The system of claim 8, further comprising a positionable magnet configured to be inserted into each of the first and second valves.

* * * * *

UNITED STATES PATENT AND TRADEMARK OFFICE
CERTIFICATE OF CORRECTION

PATENT NO.        : 9,624,531 B2
APPLICATION NO.   : 14/666573
DATED             : April 18, 2017
INVENTOR(S)       : Jesus Ching et al.

Page 1 of 1

It is certified that error appears in the above-identified patent and that said Letters Patent is hereby corrected as shown below:

In the Claims

In Claim 8, Column 18, Line 35, delete "defining a first," and insert --defining a first-- therefor.

In Claim 12, Column 19, Line 7, delete "chamber and," and insert --chamber and-- therefor.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*